US007071377B2

(12) United States Patent
Gonsalves et al.

(10) Patent No.: US 7,071,377 B2
(45) Date of Patent: Jul. 4, 2006

(54) METHOD TO CONTROL THE RIPENING OF PAPAYA FRUIT AND CONFER DISEASE RESISTANCE TO PAPAYA PLANTS

(75) Inventors: Dennis Gonsalves, Hilo, HI (US); Aladje Baldé, Monte-Abrao (PT); Maria Salomé Soares Pais, Lisboa (PT); Chu-Hui Chiang, Tainan (TW)

(73) Assignees: Cornell Research Foundation, Inc., Ithaca, NY (US); Institute of Applied Science and Technology (ICAT)-Laboratory for Plant Biotechnology, Lisboa (PT)

( * ) Notice: Subject to any disclaimer, the term of this patent is extended or adjusted under 35 U.S.C. 154(b) by 147 days.

(21) Appl. No.: 10/121,539

(22) Filed: Apr. 11, 2002

(65) Prior Publication Data

US 2003/0204869 A1 Oct. 30, 2003

Related U.S. Application Data

(60) Provisional application No. 60/283,022, filed on Apr. 11, 2001.

(51) Int. Cl.

| | |
|---|---|
| ***C12N 15/82*** | (2006.01) |
| ***C12N 15/90*** | (2006.01) |
| ***C12N 5/10*** | (2006.01) |
| ***A01H 5/00*** | (2006.01) |

(52) U.S. Cl. .................... 800/286; 435/320.1; 435/419; 435/468; 800/278; 800/280; 800/283; 800/301

(58) Field of Classification Search .............. 435/320.1, 435/419, 468, 471, 254.2; 800/278, 279, 800/230, 283, 285, 286, 301

See application file for complete search history.

(56) References Cited

U.S. PATENT DOCUMENTS

| | | | | |
|---|---|---|---|---|
| 5,583,021 A | * 12/1996 | Dougherty et al. | 435/468 |
| 5,767,376 A | 6/1998 | Stiles et al. | 435/468 |
| 5,998,699 A | 12/1999 | Slightom et al. | 435/468 |
| 6,002,072 A | 12/1999 | McMaster et al. | 435/468 |
| 6,046,384 A | 4/2000 | McMaster et al. | 800/279 |
| 6,069,000 A | 5/2000 | Andersen et al. | 435/197 |
| 6,124,525 A | 9/2000 | Botella | 800/298 |
| 6,750,382 B1 | 6/2005 | Pang et al. | |
| 6,903,248 B1 | 6/2005 | Pang et al. | |
| 2003/0115633 A1 | 6/2003 | Pais et al. | |
| 2003/0172397 A1 | 9/2003 | Gonsalves et al. | |

FOREIGN PATENT DOCUMENTS

WO WO 96/21019 * 7/1996

OTHER PUBLICATIONS

Silva-Rosales et al., Arch. Virol., 2000, vol. 145, pp. 835-843.*

Voinnet, O., Trends in Genetics, Aug. 2001, vol. 17, pp. 449-459.*

Gouveia et al., "C. Papaya mRNA for Pectinesterase," Accession No. Y07899, 1996.

Gouveia et al., "C. Papaya spgl Gene," Accession No. Y07900, 1996.

D'Innocinzo et al., "Carcia Papaya Beta-Galactosidase mRNA, Partial Cds.," Accession No. AF079874, 1998.

Othman et al., "Carcia Papaya Beta-Galactosidase Precursor, mRNA, , Complete Cds.," Accession No. AF064786, 1998.

Lam et al., "Carcia Papaya mRNA for Beta Galactosidase, Partial," Accession No. AJ012578, 1998.

Balde et al., "Carica Papaya B-Galactosidase mRNA," Accession No, AF136187, 1999.

Lim et al., "Isolation and Characterization of Pectin Methylesterase from Papaya," *Archives of Biochemistry and Biophysics* 307(1):15-20 (1993).

Steele et al., "Pectin Modification in Cell Walls of Ripening Tomatoes Occurs in Distinct Domains," *Plant Physiol.* 114:373-381 (1997).

Kagan-Zur et al., "Differential Regulation of Polygalacturonase and Pectin Methylesterase Gene Expression During And After Heat Stress in Ripening Tomato (*Lycopersicon esculentum* Mill.) Fruits," *Plant Molecular Biology* 29:1101-1110 (1995).

Tieman et al., "Reduction in Pectin Methylesterase Activity Modifies Tissue Integrity and Cation Levels in ripening Tomato (*Lycopersicon esculenium* Mill.) Fruits," *Plant Physiol.* 106:429-436 (1994).

Gaffe et al., "Pectin Methylesterase Isoforms in Tomato (*Lycopersicon esculentum*) Tissues. Effects of Expression of a Pectin Methylesterase Antisense Gene," *Plant Physiol*, 105:199-203 (1994).

Harriman et al., "Moleuclar Cloning of Tomato Pectin Methylesterase Gene and its Expression in Rutgers, Ripening Inhibitor, Nonripening, and Never Ripe Tomato Fruit," *Plant Physiol.* 97:80-87 (1991).

(Continued)

*Primary Examiner*—Aswin Mehta
(74) *Attorney, Agent, or Firm*—Nixon Peabody LLP

(57) ABSTRACT

The present invention relates to DNA constructs which include DNA molecules which affect papaya fruit ripening and DNA molecules which encode papaya ringspot virus coat protein. The present invention further relates to a method of controlling papaya fruit ripening while conferring resistance to Papaya Ringspot Virus by transforming plants with the DNA construct. The present invention also relates to expression systems, host cells, and transgenic plants containing the DNA constructs of the invention.

22 Claims, 5 Drawing Sheets

OTHER PUBLICATIONS

Fitch et al., "Virus Resistant Papaya Plants Derived from Tissues Bombarded with the Coat Protein Gene of Papaya Ringspot Virus," *Biotechnology* 10: 1466–1472 (1992).

Tieman et al., "An Antisense Pectin Methylesterase Gene Alters Pectin Chemistry and Soluble Solids in Tomato Fruit," *The Plant Cell* 4:667–679 (1992).

Lazan et al., "β–Galactosidase, Polygalacluronase and Pectinesterase in Differential Softening and Cell Wall Modificatio n During Papaya Fruit Ripenening," *Physiologica Plantarum* 95:106–112 (1995).

Paull et al., "Postharvest Variation in Cell–Wall–Degrading Enzymes of Papaya (*Carica papaya* L.) During Fruit Ripening," *Plant Physiol.* 72:382–385 (1983).

Purcifull et al., "Papaya Ringspot Virus," *CMI/AAB Descriptions of Plant Viruses* vol. 292 (No. 84 revised) 8 pp. (1984).

Clark et al., "Characteristics of the Microplate Method of Enzyme–Linked Immunosorbent Assay for the Detection of Plant Viruses," *J. Gen. Virol*, 34:475–483 (1977).

Sanford et al., "The Concept of Parasite–Derived Resistance—Deriving Resistance Genes from the Parasite's Own Genome," *J. Theor. Biol*, 113:395–405 (1985).

Powell Abel et al., "Delay of Disease Development in Transgenic Plants That Express the Tobacco Mosaic Virus Coat Protein Gene," *Science* 232:738–743 (1986).

Golemboski et al., "Plants Transformed with a Tobacco Mosaic Virus Nonstructural Gene Sequence are Resistant to the Virus," *Proc. Natl. Acad. Sci*, 87:6311–6315 (1990).

Beck et al., "Disruption of Virus Movement Confers Broad–Spectrum Resistance Against Systemic Infection by Plant Viruses with a Triple Gene Block," *Proc. Natl. Acad. Sci.* 91:10310–10314 (1994).

Nelson et al., "Virus Tolerance, Plant Growth, and Field Performance of Transgenic tomato Plants Expressing Coat Protein from Tobacco Mosaic Virus," *Biotechnology* 6:403–409 (1988).

Stark et al., "Protection Against Potyvirus Infection in Transgenic Plants: Evidence for Broad Spectrum Resistance," *Biotechnology* 7:1257–1262 (1989).

Waterhouse et al., "Virus Resistance and Gene Silencing in Plants Can Be Induced by Simultaneous Expression of Sense and Antisense RNA," *Proc. Natl. Acad. Sci. USA* 95:13959–13964 (1998).

Ali et al., "The Biochemical Basis of Accelerated Softening in Papaya Following Storage at Low Temperature," *Acta Horticulture* 343:230–232 (1993).

Chan et al., "Papaya Poligalacturonase and its Role in Thermally Injured Ripening Fruit," *J. Food Sci*, 46:190–192 & 197 (3 pages total) (1981).

Manshardt, "Papaya," in *Papaya in Biotechnology of Perennial Fruit Crops*, Hammerschlag, ed., Wallingford, UK: CAB Int., Chapter 21:489–511 (1992).

Maiti et al., "Plants that Express a Polyvirus Proteinase Gene are Resistant to Virus Infection," *Proc. Natl. Acad. Sci. USA*, 90:6110–6114 (1993).

Grumet, "Development of Virus Resistant Plants via Genetic Engineering," *Plant Breeding Reviews* 12:47–79 (1994).

Tennant et al., "Differential Protection Against Papaya Ringspot Virus Isolates in Coat Protein Gene Transgenic Papaya and Classically Cross–Protected Papaya," *Phytopathology* 84(11):1359–1366 (1994).

Dougherty et al., "Transgenes and Gene Suppression: Telling us Something New?," *Current Opinion in Cell Biology* 7:399–405 (1995).

Lomonossoff, "Pathogen–Derived Resistance to Plant Viruses," *Ann. Rev. Phytopathol.* 33:323–343 (1995).

Baulcombe, "Mechanisms of Pathogen–Derived Resistance to Viruses in Transgenic Plants," *Plant Cell* 8:1833–1844 (1996).

Lius et al., "Pathogen–Derived Resistance Provides Papaya with Effective Protection Against Papaya Ringspot Virus," *Molecular Breeding* 3:161–168 (1997).

Gonsalves, "Control of Papaya Ringspot Virus in Papaya: A Case Study," *Annu. Rev. Pytopathol*, 36:415–437 (1998).

Fuchs et al., "Resistance of Transgenic Hybrid Squash ZW–20 Expressing the Coat Protein Genes of Zucchini Yellow Masaic Virus and Watermelon Mosaic Virus to Mixed Infections by Both Polyviruses," *Bio/Technology* 13:1466–1473 (1995).

Tricoli et al., "Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus," *Bio/Technology* 13:1458–1465 (1995).

Wang et al., "Comparison of the Nuclear Inclusion b Protein and Coat Protein Genes of Five Papaya Ringspot Virus Strains Distinct in Geographic Origin and Pathogenicity," *Phytopathology* 84(10):1205–1210 (1994).

Bateson et al., "The Nucleotide Sequence of the Coat Protein Gene and 3' Untranslated Region of Papaya Ringspot Virus Type W (Aust)," *Arch. Virol.* 123:101–109 (1992).

Jan et al., "A Minimum Length of N Gene Sequence in Transgenic Plant Is Required for RNA–Mediated Tospovirus Resistance," *Journal of General Virology* 81: 235–242 (2000).

Bateson et al., "Papaya Ringspot Potvirus: Isolate Variability and the Origin of PRSV Type P (Australia)," *Journal of General Virology* 75:3547–3553 (1994).

Ling et al., "Protection Against Detrimental Effects of Polyvirus Infection in Transgenic Tobacco Plants Expressing the Papaya Ringspot Virus Coat Protein Gene," *Bio/Technology* 9:752–758 (1991).

Quemada et al., "The Nucleotide Sequences of the 3'–Terminal Regions of Papaya Ringspot Virus Strains W and P," *Journal of General Virology* 71:203–210 (1990).

Junjun et al., "Study on Replicase (Subunit) Gene of Papaya Ringspot Virus Cloning, Sequencing and Construction of Higher Plant Expression Vector," *Chinese Journal of Biotechnology* 10(3): 219–224 (1994).

Yeh et al., "Complete Nucleotide Sequence and Genetic Organization of Papaya Ringspot Virus RNA," *Journal of General Virology* 73:2531–2541 (1992).

Nagel et al., "Complementary DNA Cloning and Expression of the Papaya Ringspot Potyvirus Sequences Encoding Capsid Protein and a Nuclear Inclusion–Like Protein in *Escherichia coli,*" *Virology* 143: 435–441 (1985).

Martin, D., "Papaya Production Statistics," *Proc. Annu. Hawaii Papaya Ind. Assoc. Conf., 39th, Kihei*, pp. 31–36, Sep. 23–24 (1994).

Galinsky, "World Market for Papaya," *Reg. Agribus. Proj. Mark. Inf. Bull.*, Feb. No. 12, 5 pp. (1996).

Cai et al., "A Protocol for Efficient Transformation and Regeneration of *Carica Papaya* L.," *In Vitro Cell Dev Biol–Plant* 35:61–69 (1999).

Napoli et al., "Introduction of a Chimeric Chalcone Synthase Gene into Petunia Results in Reversible Co–Suppression of Homologous Genes *in trans,*" *The Plant Cell* 2:279–289 (1991).

Pilling et al., "Expression of a *Petunia inflata* Pectin Methyl Esterase in *Solanum tuberosum* L. Enhances Stem Elongation and Modifies Cation Distribution," *Planta* 210:391–399 (2000).

Carey et al., "Down–Regulation of a Ripening–Related β–Galactosidase Gene (TBGI) in Transgenic Tomato Fruits," *J Experimental Botany* 52(357):663–668 (2001).

Tennant et al., "Papaya Ringspot Virus Resistance of Transgenic Rainbow and SunUp Is Affected by Gene Dosage, Plant Development, and Coat Protein Homology," *Eur. J. Plant Pathol* 107:645–653 (2001).

Pang et al., "Non–target DNA Sequences Reduce the Transgene Length Necessary for RNA–Mediated Tospovirus Resistance in Transgenic Plants," *Proc Natl Acad Sci USA* 94:8261–8266 (1977).

GenBank Accession No. X67673, Wang et al.; "Papaya Ringspot Virus Isolate HA Genomic RNA," (1992).

GenBank Accession No. X67672 S49774, Yeh et al.; "Papaya Ringspot Virus Genomic RNA for Nuclear Inclusion protein b and Coat Protein," (1993).

Cheng et al., "Efficient Transformation of Papaya by Coat Protein Gene of Papaya Ringspot Virus Mediated by *Agrobacterium* Following Liquid–Phase Wounding of Embryogenic Tissue and S with Carborundum," *Plant Cell Reports* 16:127–132 (1996).

Maoka et al., "Nucleotide Sequence of the Capsid Protein Gene of Papaya Leaf–Distortion Mosaic Potyvirus," *Arch Virol* 141:197–204 (1996).

Anandalakshmi et al., "A Viral Suppressor of Gene Silencing in Plants," *Proc Natl Acad Sci USA* 95:13079–13084 (1998).

Kasschau et al., "A Counterdefensive Strategy of Plant Viruses: Suppression of Posttranscriptional Gene Silencing," *Cell* 95(4):461–470 (1998) (Abstract).

Llave et al., "Virus–Encoded Suppressor of Posttranscriptional Gene Silencing Targets a Maintence Step in the Silencing Pathway," *Proc Natl Acad Sci USA* 97(24):13401–13406 (2000).

Voinnet et al., "Suppression of Gene Silencing: A General Strategy Used by Diverse DNA and RNA Viruses of Plants," PNAS 96(24):14147–14152 (1999).

Voinnet & Baulcombe, "Systemic Signalling in Gene Silencing," *Nature* 389:553 (1997).

* cited by examiner

METHOD TO CONTROL THE RIPENING OF PAPAYA FRUIT AND CONFER DISEASE RESISTANCE TO PAPAYA PLANTS

This application claims the benefit of U.S. Provisional Patent Application Ser. No. 60/283,022, filed Apr. 11, 2001.

FIELD OF THE INVENTION

The present invention relates to nucleic acid constructs containing nucleic acid molecules encoding papaya proteins or polypeptides which control papaya fruit ripening and nucleic acids encoding papaya ringspot virus coat proteins, and methods of controlling papaya fruit ripening and conferring resistance to ringspot virus coat in transgenic plants transformed with such constructs.

BACKGROUND OF THE INVENTION

Papaya (*Carica papaya L.*) is an important fruit crop grown widely in tropical and subtropical lowland regions (Manshardt, "Papaya in Biotechnology of Perennial Fruit Crops," ed. *Hammerschlag,* 21:489–511, CAB Int., Wallingford, UK (1992)). Worldwide, Brazil, India, and Mexico are the largest producers of papaya. Hawaii, the largest producer of papaya in the United States, exporting about 66% of the total fresh production, primarily to the US mainland and Japan (Martin, "Papaya Production Statistics," *Proc. Annu. Hawaii Papaya Ind. Assoc. Conf.,* 39*th, Kihei*, pp. 31–36, Sept. 23–24 (1994)). The FAO estimated that about 5.7 million metric tons of fruit were harvested in 1995, almost double the 1980 harvest (Galinsky, "World Market for Papaya," *Reg. Agribus. Proj. Mark. Inf. Bull.* Feb. No. 12, 5 pp. (1996)).

Papaya ringspot virus ("PRSV") is a member of the potyvirus group of plant viruses, which are pathogenic to several crop plants, and which exhibit cross-infectivity between members of different plant families. Generally, a potyvirus is a single-stranded (+) RNA plant virus. The viral genome is approximately 10,000 bases in length. The expression strategy of potyviruses includes translation of a complete polyprotein from the positive sense viral genomic RNA. PRSV is by far the most widespread and damaging virus that infects papaya, occurring worldwide wherever papaya is grown (Purcifull, "Papaya Ringspot Virus," CMI/AAB Descr. Plant Viruses, No. 292 (No. 84 Revis., July 1984) 8 pp. (1984)). PRSV infections have resulted in the devastation of the papaya industry in Brazil, Taiwan, and Hawaii in recent years (Gonsalves, D., "Control of Papaya Ringspot Virus in Papaya: A Case Study," *Annu. Rev. Phytopathol.* 36:415–37 (1998)). Various attempts have been made to control or prevent infection of crops by PRSV, but these have been largely unsuccessful.

The concept of parasite-derived resistance ("PDR"), conceived in the middle 1980s, offered a new approach for controlling PRSV (Sanford et al., "The Concept of Parasite-Derived Resistance—Deriving Resistance Genes from the Parasite's Own Genome," *J. Theor. Biol.* 113:395–405 (1985)). Parasite-derived resistance is a phenomenon whereby transgenic plants containing genes or sequences of a parasite are protected against detrimental effects of the same or related pathogens. (Powell-Abel et al., "Delay of Disease Development in Transgenic Plants that Express the Tobacco Mosaic Virus Coat Protein Gene," *Science,* 232:738–43 (1986); (Lomonossoff, G. P., "Pathogen-Derived Resistance to Plant Viruses," *Ann. Rev. Phytopathol.* 33:323–43 (1995)).

The vast majority of reports regarding PDR have utilized the coat protein ("CP") genes of the viruses that are targeted for control (Powell-Abel et al., "Delay of Disease Development in Transgenic Plants that Express the Tobacco Mosaic Virus Coat Protein Gene," *Science,* 232:738–43 (1986)); however, a growing number of reports have shown that viral replicase (Golemboski et al., "Plants Transformed with a Tobacco Mosaic Virus Nonstructural Gene Sequence are Resistant to the Virus," *Proc. Natl. Acad. Sci. USA* 87:6311–15 (1990)), movement protein (Beck et al., "Disruption of Virus Movement Confers Broad-Spectrum Resistance Against Systemic Infection by Plant Viruses with a Triple Gene Block," *Proc. Natl. Acad. Sci. USA* 91:10310–14 (1994)), nuclear inclusion a-proteases ("NIa proteases") of potyviruses (Maiti et al., "Plants that Express a Potyvirus Proteinase Gene are Resistant to Virus Infection," *Proc. Natl. Acad. Sci. USA* 90:6110–14 (1993)), and other viral genes are also effective in conferring resistance. Furthermore, viral genes can be effective in the translatable and non-translatable sense forms, and, less frequently, antisense forms (Baulcombe, D. C., "Mechanisms of Pathogen-Derived Resistance to Viruses in Transgenic Plants," *Plant Cell* 8:1833–44 (1996); Dougherty et al., "Transgenes and Gene Suppression: Telling us Something New?" *Current Opinion in Cell Biology* 7:399–05 (1995); Lomonossoff, G. P., "Pathogen-Derived Resistance to Plant Viruses," *Ann. Rev. Phytopathol.* 33:323–43 (1995)).

Although the testing of transgenic plants have been largely confined to laboratory and greenhouse experiments, a growing number of reports showed that resistance is effective under field conditions (Grumet, R., "Development of Virus Resistant Plants via Genetic Engineering," *Plant Breeding Reviews* 12:47–49 (1994)). Two virus resistant crops have been deregulated by APHIS/USDA and, thus, are approved for unrestricted release into the environment in the U.S.A. Squash that are resistant to watermelon mosaic virus 2 and zucchini yellow mosaic potyviruses have been commercialized (Fuchs et al., "Resistance of Transgenic Hybrid Squash ZW-20 Expressing the Coat Protein Genes of Zucchini Yellow Mosaic Virus and Watermelon Mosaic Virus 2 to Mixed Infections by Both Potyviruses," *Bio/Technology* 13:1466–73 (1995); Tricoli, et al., "Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus," *Bio/Technology* 13:1458–65 (1995)). A transgenic Hawaiian papaya that is resistant to PRSV has also been developed (Fitch et al., "Virus Resistant Papaya Derived from Tissues Bombarded with the Coat Protein Gene of Papaya Ringspot Virus," *Bio/Technology* 10:1466–72 (1992); Tennant et al., "Differential Protection Against Papaya Ringspot Virus Isolates in Coat Protein Gene Transgenic Papaya and Classically Cross-Protected Papaya," *Phytopathology* 84:1359–66 (1994)). This resistant transgenic papaya was recently deregulated by the Animal and Plant Health Information Service of the United states Department of Agriculture ("USDA/APHIS"). Deregulation of the transgenic papaya is timely, because Hawaii's papaya industry is being devastated by PRSV. Remarkable progress has been made in developing virus resistant transgenic plants despite a poor understanding of the mechanisms involved in the various forms of pathogen-derived resistance (Lomonossoff, G. P., "Pathogen-Derived Resistance to Plant Viruses," *Ann. Rev. Phytopathol.* 33:323–43 (1995)).

Unfortunately, the papaya grower faces a second natural challenge that threatens to limit the growth of the industry: the fragility of the papaya fruit. The characteristic fragility of ripe papaya fruit limits the large-scale exportation of mature papaya to countries in temperate regions. To minimize this problem, the current practice is to collect fruits for exportation in very precocious phases of maturation with the consequence of adulteration of the organoleptic characteristics of this fruit. This early harvest of fruit, designed to avoid damage in subsequent handling, can result in a failure to develop optimum fruit flavor and color. Another tactic is employed to slow the ripening process in-transit by shipping and storing papaya at cold temperatures. This practice ultimately results in significant fruit damage also, as papaya fruit is susceptible to chilling injury, with critical temperatures ranging between 10–15° C. In papaya, the symptoms of chilling injury are more evident upon returning the fruit to higher ripening temperatures, which results in excessive softening and the associated enhancement of pathogen susceptibility (Chan et al., "Electrolyte Leakage and Ethylene Production Induced by Chilling Injury of Papayas," *Hort. Science* 20:1070–1072 (1985); Lyons et al., "Chilling Injury," in Weichmann, ed., *Postharvest Physiology of Vegetables, New York: Marcell Dekker Inc., pp.* 305–326, (1987)).

In an effort to solve the problems associated with long-distance shipping of fruit generally, researchers have concentrated on unraveling the role of enzymes involved in the ripening process. Three enzymes that have surfaced as vital for fruit ripening are pectinmethylesterase ("PME"), β-glucuronidase ("β-Gal"), and the polygalacturonase ("PG") family.

PME is a pectolytic enzyme which has been implicated in fruit ripening (Bacic et al., "Structure and Function of Plant Cell Walls," in *The Biochemistry of Plant: A Comprehensive Treatise*, ed. *J. Preiss,* 14:297–371, New York: Academic (1988)). This cell wall metabolizing enzyme is responsible for the demethylation of galacturonic acid residues in high molecular weight pectin, each methyl group being converted to a proton and methanol (Hall et al., "Molecular Characterization of cDNA Clones Representing Pectin Esterase Isozymes from Tomato," *Plant Mol. Biol.* 25(2):313–318 (1994)). PME activity has been reported to increase during the development of banana (Brady, "The Pectinesterase of Pulp Banana Fruit," *Aust. J. Plant Physiol.* 3:163–172 (1976)), apple (Knee, "Metabolism of Polygalacturonase in Apple Fruit Cortical Tissue During Ripening," *Phytochemistry* 17:1262–1264 (1979)), avocado (Awad et al., "Postharvest Variation in Cellulase, Polygalacturonase and Pectin Methylesterase in Avocado (*Persea americana*) Fruit in Relation to Respiration and Ethylene Production," *Plant Physiol.* 64:306–308 (1979)), and papaya (Paul et al., "Postharvest Variation in Cell Wall Degrading Enzymes of Papaya (*Carica papaya*) During Ripening," *Plant Physiol.* 72:382–385 (1983)). The exact role of PME in fruit development and ripening is yet to be determined. However, it has been hypothesized that de-esterification of pectin by PME and further depolymerization by PG are involved in fruit softening. This hypothesis is based on the observation that demethylation of pectin by PME causes a several-fold increase in cell wall solubilization by PG (Pressey et al., "Solubilization of Cell Wall by Tomato Polygalacturonase Effects of Pectinesterase," *J. Food Biochem.* 6:57–74 (1982)).

A wide range of enzymes is known to catalyze aspects of pectin modification and disassembly. Among those best characterized are exo- and endo-polygalacturonases ("PGs"), which are implicated in the disassembly of pectin that accompanies many stages of plant development, in particular those requiring cell separation. Although being clear that PG participates in a wide range of developmental processes, the majority of research has been focused on its role in fruit ripening.

PG-dependent disassembly has been most extensively studied in ripening tomatoes. Following the experiences of suppression of PG gene expression in wild type tomato and on the ectopic expression of PG in the ripening impaired pleiotropic mutant ripening inhibitor ("rin"), it has been considered that PG-mediated pectin depolymerization is not necessary for normal ripening and softening (Sheehy et al., "Reduction of Polygalacturonase Activity in Tomato Fruit by Antisense RNA," *Proc. Natl. Acad. Sci. USA* 85:8805–8809 (1988); Smith et al., "Antisense RNA Inhibition of Polygalacturonase Gene Expression in Transgenic Tomatoes," *Nature* 334:724–726 (1988); Giovannoni et al., "Expression of a Chimeric Polygalacturonase Gene in Transgenic Rin (Ripening Inhibitor) Tomato Fruit Results in Polyuronide Degradation But Not Fruit Softening," *Plant Cell* 1:53–63 (1989)). Research performed with transgenic sense and antisense tomatoes suggests that PG-mediated pectin disassembly does not contribute to early fruit ripening but contributes to tissue deterioration in the late stages of fruit ripening (Hadfield et al., "Polygalacturonase Gene Expression in Ripe Melon Fruit Supports a Role for Polygalacturonase in Ripening-Associated Pectin Disassembly," *Plant Physiol.* 117: 363–373 (1998)). Analysis of cell walls from transgenic fruits with altered levels of PG activity led to the conclusion that pectin depolymerization and pectin solubilization are due to distinct enzymatic determinants (Hadfield et al., "Polygalacturonase: Many Genes in Search of a Function," *Plant Physiol.* 117:337–343 (1998)). According to the same authors, pectin solubilization is primarily due to the action of PG. The fact that pectins in PG-complemented rin fruit are both solubilized and depolymerized accounts for the conclusion that PG activity is necessary and sufficient for pectin depolymerization, but it may be one of multiple, redundant pectin-solubilizing activities (Hadfield et al., "Polygalacturonase: Many Genes in Search of a Function," *Plant Physiol.* 117:337–343 (1998)).

In papaya, the gradual firmness loss of fruit is associated with a discernible, although very limited, increased in PG activity (Ali et al., "The Biochemical Basis of Accelerated Softening in Papaya Following Storage at Low Temperature," *Acta Horticulture* 343 (1993)). In contrast, other fruits such as strawberry (*Fragaria ananassa*) (Huber, "Strawberry Fruit Softening: The Potential Roles of Polyuronides and Hemicelluloses," *J. Food Sci.* 49:1310–1315 (1984)), melon (*Cucumis melo*) (McCollum et al., "Modification of Polyuronides and Hemicelluloses During Muslanelon Fruit Softening," *Physiol. P*1. 76:303–308 (1989)), and persimmon (*Diospyrus kaki*) (Cutillas-Iturralde et al., "Metabolism of Cell Wall Polysaccharides from Persimmon Fruit: Solubilization During Fruit Ripening Occurs in Apparent Absence of Polygalacturonase Activity," *Physiol. Plant.* 89:369–375 (1993)) have been reported as lacking endo-PG activity. Recently, it was demonstrated that PG mRNA accumulation can occur at late stages of ripening at levels much lower than those observed in ripening tomato, only detectable by using very accurate methods (Wu et al., "Endopolygalacturonase in Apples (*Malus domestica*) and its Expression During Fruit Ripening," *Plant Physiol.* 102:219–225 (1993)). It has also been reported that of three genes encoding melon PGs, one of those (MPG1) encodes an endo-PG with the potential to depolymerize melon fruit cell wall pectin (Hadfield et al., "Polygalacturonase Gene Expression in Ripe Melon Fruit Supports a Role for Polygalacturonase in Ripening-Associated Pectin Disassembly,"

*Plant Physiol.* 117:363–373 (1998)). It is therefore possible that in some fruits the disassembly of pectins in late stages of ripening is PG dependent, even in fruits with very low levels of PG activity (Hadfield et al., "Polygalacturonase: Many Genes in Search of a Function," *Plant Physiol.* 117:337–343 (1998)).

Another enzyme that has been implicated in fruit ripening is β-Gal, an enzyme involved in cell wall softening and known to exist in three isoforms (β-Gal I, β-Gal II, and β-Gal III). In "β-Galactosidases in Ripening Tomatoes," *Plant Physiol.* 71:132–135 (1983), Pressey et al., reported on the increase of activity of one of the three β-galactosidases isozymes during tomato ripening, suggesting that these isozymes may play a role on degradation of cell wall galactan, which may account for the involvement of β-Gal in fruit softening. The involvement of β-Gal in tomato fruit ripening has been confirmed (Watkins et al., "Activities of Polygalacturonase α-D Mannosidase and α-D and β-D Galactosidases in Ripening Tomato," *Hortscience* 23: 192–94 (1988)). More recently, the increase of β-Gal during ripening of kiwi fruit (Wegrzyn et al., "Pectinesterase, Polygalacturonase and β-Galactosidase During Softening of Ethylene-Treated Kiwi Fruit," *HortScience* 27:900–902 (1992)), mango and papaya (Lazan et al., "Cell Wall Hydrolases and Their Potential in the Manipulation of Ripening of Tropical Fruits," *Asean Food J.* 8:47–53 (1993)), avocado (De Veau et al., "Degradation and Solubilization of Pectin by β-Galactosidases Purified from Avocado Mesocarp," *Physio. Plant* 87:279–285 (1993)), and coffee (Golden et al., "β-Galactosidase from *Coffea arabica* and its Role in Fruit Ripening," *Phytochemistry* 34:355–360 (1993)) have been reported. In apples, the loss of fruit firmness during ripening has been associated with increased activity of β-galactosidase and a decrease in the Gal content of the cell wall (Bartley, "β-Galactosidase Activity in Ripening Apples," *Phytochemistry* 13:2107–2111 (1974); Wallner, "Apple Fruit β-Galactosidase and Softening in Storage," *J. Am. Soc. Hort. Sci.* 103:364 (1978)). Furthermore, Kang et al., "N-Terminal Amino Acid Sequence of Persimmon Fruit β-galactosidase," *Plant Physiol.* 105:975–979 (1994) purified two isozymes (one 34 kD and the other 44 kD) from persimmon fruit. A characteristic feature during the ripening of papaya fruit is softening. β-galactosidase might contribute significantly to pectin and hemicellulose modification and, hence, to softening of the fruit (Lazan et al., "β-galactosidase, Polygalacturonase and Pectinesterase in Differential Softening and Cell Wall Modification During Papaya Fruit Ripening," *Physiol. Plant* 95:106–112 (1995)).

According to Ali et al., "The Biochemical Basis of Accelerated Softening in Papaya Following Storage at Low Temperature," *Acta Horticulture* 343 (1993), PME, PG, and the β-Gal isoforms may collectively play a significant role in the development of the chilling injury symptom of increased-susceptibility-to-disease commonly observed in papaya upon returning chill-stored fruits to warmer environments. Attempts to deliver mature, full-flavored, and unadulterated papaya fruits to the consumer by long-distance transport have concentrated thus far on largely unsuccessful measures such as early harvest and low temperature storage. Given the complexity of the ripening process in papaya, it not surprising that delivering mature, full-flavored, and unadulterated papaya fruits using such measures as early harvest and low temperature storage have been largely unsuccessful.

The papaya industry is doubly vulnerable: first, to the potential for wholesale destruction from PRSV infection and, second, to unremediable damage to the fruit in long-distance transport to consumers. What is needed is a solution which utilizes and adapts the natural maturation process of the papaya such that the fruit can tolerate the stresses of long-distance exportation, carried out in combination with a method to confer PRSV resistance to papaya plants.

The present invention is directed to overcoming these and other deficiencies in the art.

SUMMARY OF THE INVENTION

The present invention relates to a DNA construct which contains a first DNA molecule encoding a protein or polypeptide which controls papaya fruit ripening and a second DNA molecule encoding a papaya ringspot virus coat protein.

The present invention also relates to methods of controlling the ripening of papaya fruit and conferring disease resistance to a plant. This involves transforming a plant cell with the DNA construct of the present invention and regenerating a plant from the transformed cell under conditions effective to control ripening and confer disease resistance.

The present invention also relates to host cells, plant cells and transgenic plants containing the nucleic acid construct of the present invention.

BRIEF DESCRIPTION OF THE DRAWINGS

FIG. 1A shows the plant expression cassette vector pEPJ86. FIG. 1B shows the transformation vector pGA482G.

FIG. 2A shows Construct 7, with a KE-CP nucleotide sequence inserted upstream from a nontranslatable β-Gal.41 nucleotide sequence. FIG. 2B shows Construct 8, with a KE-CP nucleotide sequence inserted upstream of a nontranslatable β-Gal.45 nucleotide sequence. FIG. 2C shows Construct 9, which has a nontranslatable β-Gal.41 nucleotide sequence upstream (5') of the KE-CP nucleotide. FIG. 2D shows Construct 10, which has the nontranslatable β-Gal.45 nucleotide sequence upstream (5') of the KE-CP nucleotide.

FIG. 3A shows Construct 11, containing a KE-CP nucleotide sequence inserted upstream from a nucleotide sequence derived from the conserved region ("CON") of β-Gal.41. FIG. 3B shows Construct 12, containing a KE-CP nucleotide sequence inserted upstream from a nucleotide sequence derived from the conserved region ("CON") of β-Gal.45. FIG. 3C shows Construct 13, containing KE-CP nucleotide sequence inserted upstream from a nucleotide sequence derived from the conserved region ("CON") of β-Gal.64 nucleotide sequence.

FIG. 4A shows Construct 14, which contains sequences derived from the conserved regions of β-Gal.41, β-Gal.45 and β-Gal. 64, in that order (5'→3), downstream from the KE-CP sequence. FIG. 4B shows Construct 15, which contains sequences derived from the conserved regions of β-Gal.45, β-Gal.64 and , β-Gal.41, in that order (5'→3), downstream from the KE-CP sequence. FIG. 4C shows Construct 16, which contains sequences derived from the conserved regions of β-Gal.64, β-Gal.41 and β-Gal.45, in that order (5'→3), downstream from the KE-CP sequence.

FIG. 5A shows Construct 17, which contains the nucleotide sequence encompassing one-fourth of the ORF of β-Gal.41. FIG. 5B shows Construct 18, which contains the nucleotide sequence encompassing one-half of the ORF of β-Gal.41. FIG. 5C shows Construct 19, which contains the nucleotide sequence encompassing three-fourths of the ORF of β-Gal.41. FIG. 5D shows Construct 20, which contains the nucleotide sequence encompassing the complete ORF of β-Gal.41.

DETAILED DESCRIPTION OF THE INVENTION

Figure 1:
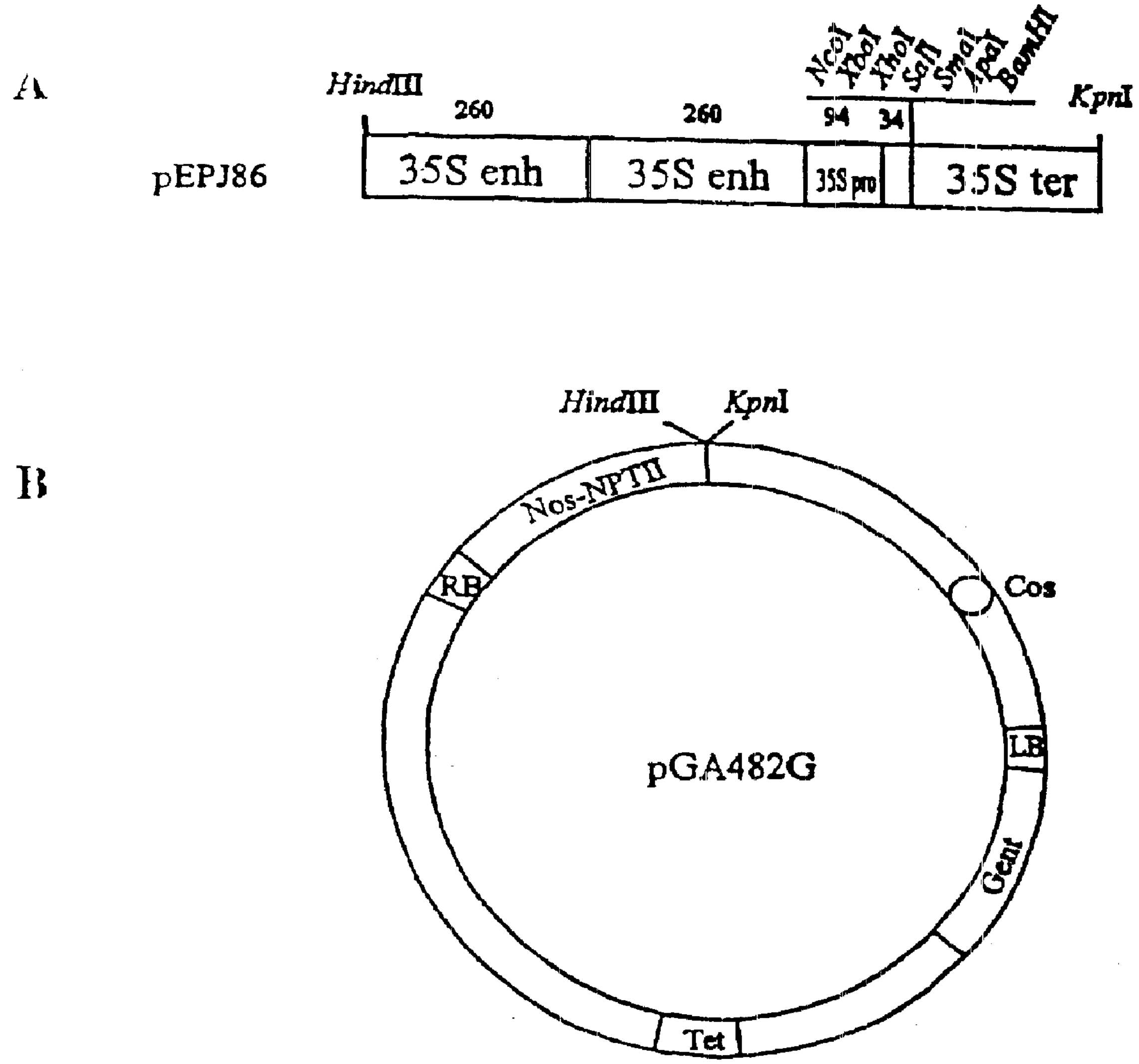
FIGS. 1A–B show the cloning vectors used for the DNA constructs of the present invention.
Figure 2:
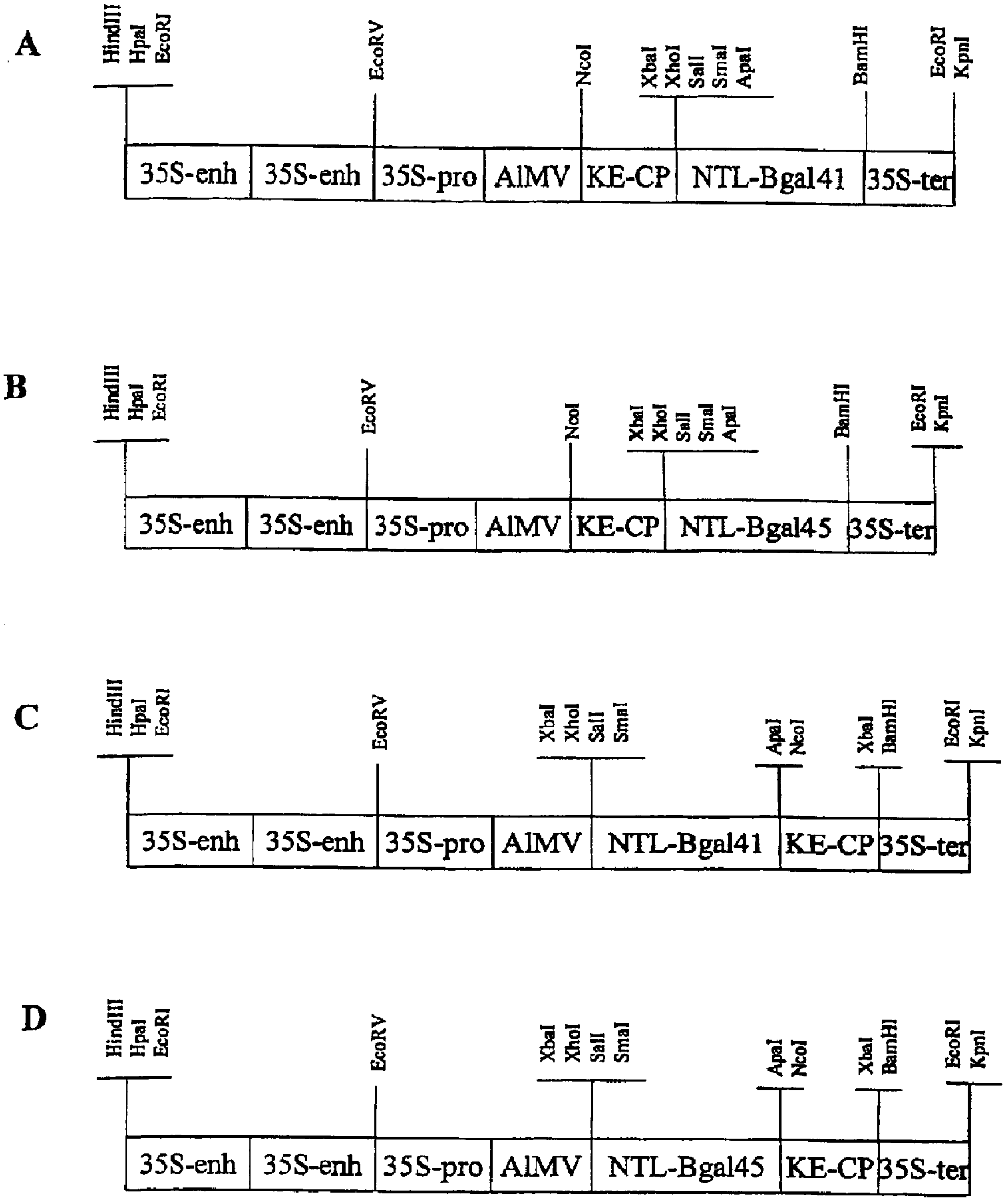
FIGS. 2A–D show the configuration of Constructs 7–10, each containing both a PRSV-CP nucleotide sequence derived from the Keaau ("KE") strain of PRSV, and a papaya fruit ripening isozyme nucleotide sequence.

The present invention relates to a DNA construct which contains a first DNA molecule encoding a protein or polypeptide which controls papaya fruit ripening and a second molecule encoding a papaya ringspot virus coat protein. The "first" and "second" DNA molecules in the DNA construct of the present invention is not meant to limit the order of the DNA molecules in the construct.

As to the first DNA molecule, this protein or polypeptide is a galactosidase, a pectinmethylesterase or a polygalacturonase.

One form of the nucleic acid molecule of the present invention is β-Gal.45, which has a nucleotide sequence corresponding to SEQ ID NO: 1, as follows:

```
agacgtacgt gttttggaat gggcatgagc cttcacctgg caaatactac tttggaggaa   60
actatgatct ggttagattc attaagctgg tgaagcaagc aggcctctat gttcatctca  120
ggattggtcc atatgtttgt gccgagtgga actttggggg ttttcctgcc cggcttaagt  180
acattccagg catcgctttc agaacgaaca atggaccttt caaggcatac atgcaaagat  240
ttacaaagaa aattgttgat atgatgaaag ctgaagggtt gtttgaatct cagggtggtc  300
caataatttt atcccagatt gaaaatgaat atggacccat ggagtacgaa cttggtgcag  360
ccgggcgtgc ttacgctcaa tgggcagctc agatggctgt gggattcggt actggtgtcc  420
cgtgggtcat gtgcaagcaa gatgatgcac ctgatcctat tattaacact tgcaatggtt  480
tctactgtga ttacttttct ccaaacaaag catacaagcc caagatgtgg actgaagctt  540
ggactggttg gtttactgga tttggaggtg cagttcctta ccgaccagtg gaagacttgg  600
cattttcagt tgcaaggttt atacagaatg gagggtcgtt cattaactat tatatgtgnc  660
atggaggaac aaattttggc cgcactgctg gtggcccctt cattgccact agctatgatt  720
atgatgctcc tcttgatgaa tatggactgg tgaggcaacc taaatggggt catttgaaag  780
atttacatcg agcaataaaa ctgtgtgaac cagcactggt gtctggtgat ccttctgtca  840
tgccacttgg acgctttcaa gaggctcatg tcttcaaatc aaaatatggg cattgtgctg  900
cattccttgc aaattacaat ccaagatctt ttgctaaagt tgcctttggg aatatgcatt  960
acaacctgcc tccttggtct atcagcattc ttcccgactg taaaaacact gtttataaca 1020
ctgcaagggt tggtgctcaa agtgctagga tgaagatggt tcctgttcct attcatggag 1080
cattctcttg gcaggcttat aatgaagagg caccttcctc aaatggtgaa aggtcattca 1140
cgacggtagg attggtggaa cagataaata caactagaga tgtctctgac tatttatggt 1200
actcaacgga tgttaagatt gatcctgatg aaggattctt gaagactgga aagtacccca 1260
cactcactgt tttatctgct ggtcatgctt tacatgtatt tgtcaacgac caactatcag 1320
gaactgccta tggaagctta gaatttccaa agataacttt cagtaaaggt gtaaatctga 1380
gagctggcat caacaagatt tcaattctaa gaattgctgt tggtcttccg aacgtcggtc 1440
ctcattttga gacatggaat gctggagttc ttggtcctgt aacattgaat ggtcttaacg 1500
agggaagaag ggacttatca tggcagaaat ggtcttacaa ggttggtgtt gaaggagaag 1560
caatgagtct tcattcaatc agtgggagtt cctcagttga gtggactgca gggtcttttg 1620
tagcaagaag gcagcccctt acttggttca aaactacttt caatgctccg gctggaaatt 1680
```

-continued

```
ctccattggc tctggatatg aatagtatgg gtaaaggaca aatatggata aatggaaaga  1740

gtatcgggcg gcactggcct gcatataaag catctggttc ttgtggttgg tgtgattatg  1800

ctggaacatt taatgagaag aagtgcttaa gtaattgtgg agaggcttct caaagatggt  1860

atcacgttcc tcgctcatgg ctcaacccaa cagggaattt gttggttgtt tttgaagaat  1920

ggggtggaga tcctaatgga atatccttgg ttagaagaga agtagacagt gtttgtgctg  1980

atatttatga gtggcaacca actctgatga attatcaaat gcaagcatct ggaaaggtaa  2040

acaaaccact gcggcctaat aaagctcatt tacagtgtgg ccctgggcag aagttctcat  2100

cagtcaagtt tgccagtttt ggcactccag aaggggcttg tggaagctac cggagggaag  2160

ctgccatgca catcattctt atgatgcttt tgagaggctc tgtgttgggc agaactggtg  2220

ctcagtaaca gtagcacccg aaatgttcgg tggagatccc tgccccagtg tcatgaagaa  2280

actcgcggtg gaggttgttt gcagctgaag aactgtaaca tcagaaaagt gatggaagtg  2340

aaggaaattg tggactgatt cttttttta caagtcatca gttatattat ttcttggata  2400

aattaagtct acacatcgaa gtttgcagcc attctgttcc agctttcaaa tggtgaagtt  2460

gtacaaatat acagcacaca ccatggatgg ctggcatctc ttacaagcat tgtcaaagtg  2520

tttgtccatt ggaaaaatgt acataaagca atgattcgtt gcctgcatgt tatatggaag  2580

tttaaggatg gaatctgtcg aagcacagtg agacggcggt aacccagtcc atgtgccaga  2640

tattttagct tttatagggt atggaaatcc tctgatttct agtcatttta agtggtacat  2700

tctctttcaa gtttcttgag aagcaaaatt gtttacactg ctttgttctt gcaagaaaaa  2760

aggaacaaag gcctcaaatg gccataatat atttactctt tttagttcaa agaaaaaaaa  2820

aaaaaaa                                                            2827
```

β-Gal.45, isolated from *Carica papaya* ("papaya"), has an open reading frame ("ORF") of 1998 bp, extending between nucleotides 231–2228. The starting codon "ATG" is identified at 231–234 bp, with the stop codon "TAA" found between nucleotides 2225–2228.

The nucleic acid sequence corresponding to SEQ ID NO: 1 encodes an isoform of β-galactosidase isolated from *Carica papaya*, identified herein as β-Gal.45, which has a deduced amino acid sequence corresponding to SEQ ID NO: 2, as follows:

```
Met Gln Arg Phe Thr Lys Lys Ile Val Asp Met Met Lys Ala Glu Gly
 1               5                  10                  15

Leu Phe Glu Ser Gln Gly Gly Pro Ile Ile Leu Ser Gln Ile Glu Asn
            20                  25                  30

Glu Tyr Gly Pro Met Glu Tyr Glu Leu Gly Ala Ala Gly Arg Ala Tyr
        35                  40                  45

Ala Gln Trp Ala Ala Gln Met Ala Val Gly Phe Gly Thr Gly Val Pro
    50                  55                  60

Trp Val Met Cys Lys Gln Asp Asp Ala Pro Asp Pro Ile Ile Asn Thr
65                  70                  75                  80

Cys Asn Gly Phe Tyr Cys Asp Tyr Phe Ser Pro Asn Lys Ala Tyr Lys
                85                  90                  95

Pro Lys Met Trp Thr Glu Ala Trp Thr Gly Trp Phe Thr Gly Phe Gly
            100                 105                 110

Gly Ala Val Pro Tyr Arg Pro Val Glu Asp Leu Ala Phe Ser Val Ala
        115                 120                 125

Arg Phe Ile Gln Asn Gly Gly Ser Phe Ile Asn Tyr Tyr Met Xaa His
    130                 135                 140

Gly Gly Thr Asn Phe Gly Arg Thr Ala Gly Gly Pro Phe Ile Ala Thr
145                 150                 155                 160
```

-continued

```
Ser Tyr Asp Tyr Asp Ala Pro Leu Asp Glu Tyr Gly Leu Val Arg Gln
                165                 170                 175

Pro Lys Trp Gly His Leu Lys Asp Leu His Arg Ala Ile Lys Leu Cys
            180                 185                 190

Glu Pro Ala Leu Val Ser Gly Asp Pro Ser Val Met Pro Leu Gly Arg
        195                 200                 205

Phe Gln Glu Ala His Val Phe Lys Ser Lys Tyr Gly His Cys Ala Ala
    210                 215                 220

Phe Leu Ala Asn Tyr Asn Pro Arg Ser Phe Ala Lys Val Ala Phe Gly
225                 230                 235                 240

Asn Met His Tyr Asn Leu Pro Pro Trp Ser Ile Ser Ile Leu Pro Asp
                245                 250                 255

Cys Lys Asn Thr Val Tyr Asn Thr Ala Arg Val Gly Ala Gln Ser Ala
            260                 265                 270

Arg Met Lys Met Val Pro Val Pro Ile His Gly Ala Phe Ser Trp Gln
        275                 280                 285

Ala Tyr Asn Glu Glu Ala Pro Ser Ser Asn Gly Glu Arg Ser Phe Thr
    290                 295                 300

Thr Val Gly Leu Val Glu Gln Ile Asn Thr Thr Arg Asp Val Ser Asp
305                 310                 315                 320

Tyr Leu Trp Tyr Ser Thr Asp Val Lys Ile Asp Pro Asp Glu Gly Phe
                325                 330                 335

Leu Lys Thr Gly Lys Tyr Pro Thr Leu Thr Val Leu Ser Ala Gly His
            340                 345                 350

Ala Leu His Val Phe Val Asn Asp Gln Leu Ser Gly Thr Ala Tyr Gly
        355                 360                 365

Ser Leu Glu Phe Pro Lys Ile Thr Phe Ser Lys Gly Val Asn Leu Arg
    370                 375                 380

Ala Gly Ile Asn Lys Ile Ser Ile Leu Ser Ile Ala Val Gly Leu Pro
385                 390                 395                 400

Asn Val Gly Pro His Phe Glu Thr Trp Asn Ala Gly Val Leu Gly Pro
                405                 410                 415

Val Thr Leu Asn Gly Leu Asn Glu Gly Arg Arg Asp Leu Ser Trp Gln
            420                 425                 430

Lys Trp Ser Tyr Lys Val Gly Val Glu Gly Glu Ala Met Ser Leu His
        435                 440                 445

Ser Leu Ser Gly Ser Ser Ser Val Glu Trp Thr Ala Gly Ser Phe Val
    450                 455                 460

Ala Arg Arg Gln Pro Leu Thr Trp Phe Lys Thr Thr Phe Asn Ala Pro
465                 470                 475                 480

Ala Gly Asn Ser Pro Leu Ala Leu Asp Met Asn Ser Met Gly Lys Gly
                485                 490                 495

Gln Ile Trp Ile Asn Gly Lys Ser Ile Gly Arg His Trp Pro Ala Tyr
            500                 505                 510

Lys Ala Ser Gly Ser Cys Gly Trp Cys Asp Tyr Ala Gly Thr Phe Asn
        515                 520                 525

Glu Lys Lys Cys Leu Ser Asn Cys Gly Glu Ala Ser Gln Arg Trp Tyr
    530                 535                 540

His Val Pro Arg Ser Trp Leu Asn Pro Thr Gly Asn Leu Leu Val Val
545                 550                 555                 560

Phe Glu Glu Trp Gly Gly Asp Pro Asn Gly Ile Ser Leu Val Arg Arg
                565                 570                 575

Glu Val Asp Ser Val Cys Ala Asp Ile Tyr Glu Trp Gln Pro Thr Leu
```

-continued

```
            580                 585                 590

Met Asn Tyr Gln Met Gln Ala Ser Gly Lys Val Asn Lys Pro Leu Arg
        595                 600                 605

Pro Asn Lys Ala His Leu Gln Cys Gly Pro Gly Gln Lys Phe Ser Ser
    610                 615                 620

Val Lys Phe Ala Ser Phe Gly Thr Pro Glu Gly Ala Cys Gly Ser Tyr
625                 630                 635                 640

Arg Arg Glu Ala Ala Met His Ile Ile Leu Met Met Leu Leu Arg Gly
                645                 650                 655

Ser Val Leu Gly Arg Thr Gly Ala Gln
            660                 665
```

Another nucleic acid molecule in accordance with the present invention isolated from *Carica papaya* is identified herein as β-Gal.64, and has a nucleic acid sequence corresponding to SEQ ID NO: 3, as follows:

```
gaatggaatt atggggggtt ccggtttggc tgaagtatgt ccctggaatc agctttagaa  60

cagacaatga gcctttcaag agagctatgc aagggttcac agagaagatt gtgggactat  120

naagagtgaa aacttgtttg agtcccaggg tggccccatt atcctctctc agattgagaa  180

tgagtacggg aaacagagca agttattngg cgccgatgga tataattata tnagttgggc  240

agcaaaaatg gctgttgaaa caggaacagg tgtcccctgg gtcatgtgca aagaagacga  300

tgcaccagat ccggtnatan acacgtgcaa atggttttac tgtgaagcat tctctcctaa  360

caaaccttac aagcccaaga tctggacgga ggcatggagt ggctggttca cagactttgg  420

tggccccatc caccagcggc cagttcagga tcttgcattt gcagttgcta agttcataca  480

aaaaggaggg tcctttgtca actattacat gtatcatggc ggcaccaact ttgg        534
```

The nucleic acid sequence corresponding to SEQ ID NO: 3 encodes an isoform of β-galactosidase isolated from *Carica papaya* identified herein as β-Gal.64, which has a deduced amino acid sequence corresponding to SEQ ID NO: 4, as follows:

```
Met Glu Leu Trp Gly Val Pro Val Trp Leu Lys Tyr Val Pro Gly Ile
  1               5                  10                  15

Ser Phe Arg Thr Asp Asn Glu Pro Phe Lys Arg Ala Met Gln Gly Phe
            20                  25                  30

Thr Glu Lys Ile Val Gly Leu Xaa Arg Val Lys Thr Cys Leu Ser Pro
        35                  40                  45

Arg Val Ala Pro Leu Ser Ser Leu Arg Leu Arg Met Ser Thr Gly Asn
    50                  55                  60

Arg Ala Ser Tyr Xaa Ala Pro Met Asp Ile Ile Ile Xaa Val Gly Gln
65                  70                  75                  80

Gln Lys Trp Leu Leu Lys Gln Glu Gln Val Ser Pro Gly Ser Cys Ala
                85                  90                  95

Lys Lys Thr Met His Gln Ile Arg Xaa Xaa Thr Arg Ala Asn Gly Phe
            100                 105                 110

Thr Val Lys His Ser Leu Leu Thr Asn Leu Thr Ser Pro Arg Ser Gly
        115                 120                 125

Arg Arg His Gly Val Ala Gly Ser Gln Thr Leu Val Ala Pro Ser Thr
```

-continued

```
    130                 135                 140

Ser Gly Gln Phe Arg Ile Leu His Leu Gln Leu Leu Ser Ser Tyr Lys
145                 150                 155                 160

Lys Glu Gly Pro Leu Ser Thr Ile Thr Cys Ile Met Ala Ala Pro Thr
                165                 170                 175

Leu
```

Another nucleic acid molecule in accordance with the present invention isolated from *Carica papaya* is identified herein as β-Gal.41, which has a nucleotide sequence corresponding to SEQ ID NO: 5, as follows:

```
ggcacgagaa acacactcaa ctcctccatt aatgtcctct ttaacaaaaa tctaaatttc  60
cttccttctc ttctactaaa cagcattgaa ggagtaaaca attatttgat attttcattt  120
gctatcatgt tgaagacaaa cctggtcttg ttcttgttgt tttgttcatg gctttggtct  180
gttgaagcta ctgtgtctta cgaccataaa gctataatca ttaatggccg cagaaggatt  240
cttatttctg gctccattca ttatcccaga agcactcctc agatgtggcc tgatcttata  300
caaaatgcta aagaaggagg gttagatgtc atacagactt atgttttttg gaacggacat  360
gagccctctc ctggaaatta ttattttgaa gacaggtatg atcttgtaaa gttcatcaag  420
ttggtgcatc aagctggtct gtatgttcat ctcagaataa gtccttatat ttgtggtgaa  480
tggaattttg gggttttcc tgtttggctc aaatacgttc ctggtattca attcagaaca  540
gacaatggac ctttcaaggc acaaatgcaa aaatttacag agaaaatagt caacatgatg  600
aaggcagaaa agttatttga acctcaaggg ggtccaataa ttatgtcaca gatagagaat  660
gagtatggac ctattgagtg ggaaattgga gcaccgggga aagcttatac aaaatgggca  720
gcacaaatgg cagtgggtct tggcactgga gtcccatgga ttatgtgcaa gcaagaggat  780
gctcctgacc caattattga cacttgcaat ggtttctatt gtgaaaattt catgccaaac  840
gccaactaca aaccaaaaat gtttacagag gcctggactg gctggtacac ggaatttggc  900
ggtccagttc cttatagacc tgcagaagac atggcttact ccgttgcaag gttcattcag  960
aataggggat cattcattaa ttattatatg taccatggag gaacaaattt tggcagaact  1020
gctggaggtc ctttcattgc tactagctat gattacgatg cccctcttga tgagtatgga  1080
ctaaggaggg agccaaaatg gggcacttg agggatttgc ataaaaccat caaattatgt  1140
gaaccatctt tagtttctgt tgatcctaaa gtgacatcgt taggaagtaa ccaagaggct  1200
catgtgtttt ggacaaaaac ctcttgtgct gcattccttg ctaactacga tctgaagtac  1260
tcagttagag tcacctttca aaacctgcct tatgacctac ctccttggtc tgtcagcatt  1320
cttcctgact gcaaaactgt agttttcaac actgcaaagg ttgtttcaca aggctcgcta  1380
gcaaagatga ttgctgtcaa cagtgcattc tcttggcagt cgtacaacga agaaacacct  1440
tccgcaaatt atgatgctgt atttaccaaa gatgggctgt gggaacagat aagtgtcacc  1500
agagatgcta cagattactt gtggtatatg acagatgtga caataggtcc tgatgaagca  1560
ttcttgaaga atgggcaaga tcccattttg acagtcatgt cagcaggcca tgctttgcat  1620
gtttttgtga atggtcaact atcaggaact gtatatggac aattggaaaa tcccaaacta  1680
gcctttagtg gcaaggtgaa actgagagca ggagtcaaca aggtttcttt actaagtatc  1740
gctgttggcc ttccgaatgt tggcttacac tttgaaacat ggaatgctgg ggttctgggt  1800
ccagtgacat tgaaaggggt gaattcagga acatgggata tgtcaaaatg gaaatggtct  1860
tacaagattg gtctgaaagg cgaagccttg agccttcata cagttagtgg cagttcgtct  1920
```

-continued

```
gttgagtggg ttgaaggatc attactagct caaagacaac ccctcatttg gtacaagact  1980
acttttaacg caccagtagg taatgatcca ttagctttag atatgaacag tatgggaaaa  2040
ggtcagatat ggataaatgg tcaaagtatt ggacgccact ggcctggata taaagctcgt  2100
ggaagttgtg gtgcttgcaa ctatgctgga atatatgatg agaaaaaatg tcatagtaac  2160
tgtggaaagg cttctcagag atggtaccat gttcctcgct cgtggctcaa cccaactgcg  2220
aacctattag ttgtttttga agaatggggt ggtgatccaa caaagatttc tttggtgaaa  2280
agagttgtgt agttagtttt cagaaagcta aaatgggtaa aggtttatag tttaacccta  2340
ataaatgaag tccccagtta ggtcaaattt agcacagaaa atagtttgga agaatccaag  2400
tgactttttg tccttagggg tgatacaagc ttaaacgaag cagattgccc agaattgcca  2460
aagggaatgg atatggtaga atatcacaac atttttatgt gcagagacaa gctattgcta  2520
cacctccata cctcatacat taggccaact agaagagtat agttttaata tatatacaca  2580
cgcacacaca cacacacagt atatcttgat aattattaag gatatacata cctctagcta  2640
gctggggttc caatctaagt attcagggaa aataaacctc atgccttctt atttgtaaga  2700
acaaatcagg aagtattatt aataaaaaaa aaaaaaaaaa aaaaaa                 2746
```

The open reading frame ("ORF") of *Carica papaya* β-Gal.41 is 2166 bp, extending between nucleotides 127–2292. The starting codon "ATG" is identified at 127–130 bp, with the stop codon "TAG" found between nucleotides 2289–2292. The nucleic acid sequence corresponding to SEQ ID NO: 5 encodes a third isoform of β-galactosidase identified herein as β-Gal.41, isolated from *Carica papaya*, which has an amino acid sequence corresponding to SEQ ID NO: 6, as follows:

```
Met Leu Lys Thr Asn Leu Val Leu Phe Leu Leu Phe Cys Ser Trp Leu
  1               5                  10                  15

Trp Ser Val Glu Ala Thr Val Ser Tyr Asp His Lys Ala Ile Ile Ile
             20                  25                  30

Asn Gly Arg Arg Arg Ile Leu Ile Ser Gly Ser Ile His Tyr Pro Arg
         35                  40                  45

Ser Thr Pro Gln Met Trp Pro Asp Leu Ile Gln Asn Ala Lys Glu Gly
     50                  55                  60

Gly Leu Asp Val Ile Gln Thr Tyr Val Phe Trp Asn Gly His Glu Pro
65                  70                  75                  80

Ser Pro Gly Asn Tyr Tyr Phe Glu Asp Arg Tyr Asp Leu Val Lys Phe
                 85                  90                  95

Ile Lys Leu Val His Gln Ala Gly Leu Tyr Val His Leu Arg Ile Ser
            100                 105                 110

Pro Tyr Ile Cys Gly Glu Trp Asn Phe Gly Gly Phe Pro Val Trp Leu
        115                 120                 125

Lys Tyr Val Pro Gly Ile Gln Phe Arg Thr Asp Asn Gly Pro Phe Lys
    130                 135                 140

Ala Gln Met Gln Lys Phe Thr Glu Lys Ile Val Asn Met Met Lys Ala
145                 150                 155                 160

Glu Lys Leu Phe Glu Pro Gln Gly Gly Pro Ile Ile Met Ser Gln Ile
                165                 170                 175

Glu Asn Glu Tyr Gly Pro Ile Glu Trp Glu Ile Gly Ala Pro Gly Lys
            180                 185                 190

Ala Tyr Thr Lys Trp Ala Ala Gln Met Ala Val Gly Leu Gly Thr Gly
        195                 200                 205

Val Pro Trp Ile Met Cys Lys Gln Glu Asp Ala Pro Asp Pro Ile Ile
```

-continued

```
    210                 215                 220

Asp Thr Cys Asn Gly Phe Tyr Cys Glu Asn Phe Met Pro Asn Ala Asn
225                 230                 235                 240

Tyr Lys Pro Lys Met Phe Thr Glu Ala Trp Thr Gly Trp Tyr Thr Glu
                245                 250                 255

Phe Gly Gly Pro Val Pro Tyr Arg Pro Ala Glu Asp Met Ala Tyr Ser
            260                 265                 270

Val Ala Arg Phe Ile Gln Asn Arg Gly Ser Phe Ile Asn Tyr Tyr Met
        275                 280                 285

Tyr His Gly Gly Thr Asn Phe Gly Arg Thr Ala Gly Gly Pro Phe Ile
    290                 295                 300

Ala Thr Ser Tyr Asp Tyr Asp Ala Pro Leu Asp Glu Tyr Gly Leu Arg
305                 310                 315                 320

Arg Glu Pro Lys Trp Gly His Leu Arg Asp Leu His Lys Thr Ile Lys
                325                 330                 335

Leu Cys Glu Pro Ser Leu Val Ser Val Asp Pro Lys Val Thr Ser Leu
            340                 345                 350

Gly Ser Asn Gln Glu Ala His Val Phe Trp Thr Lys Thr Ser Cys Ala
        355                 360                 365

Ala Phe Leu Ala Asn Tyr Asp Leu Lys Tyr Ser Val Arg Val Thr Phe
    370                 275                 380

Gln Asn Leu Pro Tyr Asp Leu Pro Pro Trp Ser Val Ser Ile Leu Pro
385                 390                 395                 400

Asp Cys Lys Thr Val Val Phe Asn Thr Ala Lys Val Val Ser Gln Gly
                405                 410                 415

Ser Leu Ala Lys Met Ile Ala Val Asn Ser Ala Phe Ser Trp Gln Ser
            420                 425                 430

Tyr Asn Glu Glu Thr Pro Ser Ala Asn Tyr Asp Ala Val Phe Thr Lys
        435                 440                 445

Asp Gly Leu Trp Glu Gln Ile Ser Val Thr Arg Asp Ala Thr Asp Tyr
    450                 455                 460

Leu Trp Tyr Met Thr Asp Val Thr Ile Gly Pro Asp Glu Ala Phe Leu
465                 470                 475                 480

Lys Asn Gly Gln Asp Pro Ile Leu Thr Val Met Ser Ala Gly His Ala
                485                 490                 495

Leu His Val Phe Val Asn Gly Gln Leu Ser Gly Thr Val Tyr Gly Gln
            500                 505                 510

Leu Glu Asn Pro Lys Leu Ala Phe Ser Gly Lys Val Lys Leu Arg Ala
        515                 520                 525

Gly Val Asn Lys Val Ser Leu Leu Ser Ile Ala Val Gly Leu Pro Asn
    530                 535                 540

Val Gly Leu His Phe Glu Thr Trp Asn Ala Gly Val Leu Gly Pro Val
545                 550                 555                 560

Thr Leu Lys Gly Val Asn Ser Gly Thr Trp Asp Met Ser Lys Trp Lys
                565                 570                 575

Trp Ser Tyr Lys Ile Gly Leu Lys Gly Glu Ala Leu Ser Leu His Thr
            580                 585                 590

Val Ser Gly Ser Ser Ser Val Glu Trp Val Glu Gly Ser Leu Leu Ala
        595                 600                 605

Gln Arg Gln Pro Leu Ile Trp Tyr Lys Thr Thr Phe Asn Ala Pro Val
    610                 615                 620

Gly Asn Asp Pro Leu Ala Leu Asp Met Asn Ser Met Gly Lys Gly Gln
625                 630                 635                 640
```

-continued

```
Ile Trp Ile Asn Gly Gln Ser Ile Gly Arg His Trp Pro Gly Tyr Lys
                645                 650                 655

Ala Arg Gly Ser Cys Gly Ala Cys Asn Tyr Ala Gly Ile Tyr Asp Glu
            660                 665                 670

Lys Lys Cys His Ser Asn Cys Gly Lys Ala Ser Gln Arg Trp Tyr His
        675                 680                 685

Val Pro Arg Ser Trp Leu Asn Pro Thr Ala Asn Leu Leu Val Val Phe
    690                 695                 700

Glu Glu Trp Gly Gly Asp Pro Thr Lys Ile Ser Leu Val Lys Arg Val
705                 710                 715                 720

Val
```

Another suitable nucleic acid molecule in accordance with the present invention encodes for a protein or polypeptide having activity as a pectinmethylesterase (PME) isolated from *Carica papaya*, which has a nucleotide sequence corresponding to SEQ ID NO: 7, as follows:

```
gcagtggtgg caaaagatgg aacgggaaac tttcagacgg tgaaagaggc catggatgcg  60

gctgatggga aaaaaaggtt tgtgatttac gtgaaagcag gagtttataa ggagaaaatt  120

cacagtaata aagacgggat tactttgatc ggagatggta aatattccac catcattgtc  180

ggtgatgata gtgttgctgg aggttccacc atgccaggct ctgcaactat tacaatgaca  240

ggggatggat tcatagcccg cgacattggg tttcagaaca cagcagggcc acaaggagag  300

caagctttag ctctaaacat agcttctgat cactctgttc tttacaggtg cagcattgcg  360

ggttaccagg atactctcta cgcacacgct ctccgtcaat tctacagaga atgcgacatc  420

tacggcaccg tcgatttcat tttcggaaac gccgccgcgg ttttccaaaa ctgctacttg  480

gttcttcgtc ttcctcggaa aaaaggctac aacgttattc tagcaaacgg aagatccgac  540

ccgggacaga acacgggttt ctctgttcac aactgcagaa tcgtacccag ctccgaattt  600

tctccggtaa aacataaata cgaatcgtat cttggtaggc catggaaaa             649
```

The nucleic acid sequence corresponding to SEQ ID NO: 7 (PME) encodes an pectinmethylesterase isolated from *Carica papaya*, identified herein as PME which has a deduced amino acid sequence corresponding to SEQ ID NO: 8, as follows:

```
Ala Val Val Ala Lys Asp Gly Thr Gly Asn Phe Gln Thr Val Lys Glu
  1               5                  10                  15

Ala Met Asp Ala Ala Asp Gly Lys Lys Arg Phe Val Ile Tyr Val Lys
            20                  25                  30

Ala Gly Val Tyr Lys Glu Lys Ile His Ser Asn Lys Asp Gly Ile Thr
        35                  40                  45

Leu Ile Gly Asp Gly Lys Tyr Ser Thr Ile Ile Val Gly Asp Asp Ser
    50                  55                  60

Val Ala Gly Gly Ser Thr Met Pro Gly Ser Ala Thr Ile Thr Met Thr
 65                  70                  75                  80

Gly Asp Gly Phe Ile Ala Arg Asp Ile Gly Phe Gln Asn Thr Ala Gly
                85                  90                  95

Pro Gln Gly Glu Gln Ala Leu Ala Leu Asn Ile Ala Ser Asp His Ser
            100                 105                 110
```

-continued

```
Val Leu Tyr Arg Cys Ser Ile Ala Gly Tyr Gln Asp Thr Leu Tyr Ala
        115                 120                 125

His Ala Leu Arg Gln Phe Tyr Arg Glu Cys Asp Ile Tyr Gly Thr Val
    130                 135                 140

Asp Phe Ile Phe Gly Asn Ala Ala Ala Val Phe Gln Asn Cys Tyr Leu
145                 150                 155                 160

Val Leu Arg Leu Pro Arg Lys Lys Gly Tyr Asn Val Ile Leu Ala Asn
                165                 170                 175

Gly Arg Ser Asp Pro Gly Gln Asn Thr Gly Phe Ser Val His Asn Cys
            180                 185                 190

Arg Ile Val Pro Ser Ser Glu Phe Ser Pro Val Lys His Lys Tyr Glu
        195                 200                 205

Ser Tyr Leu Gly Arg Pro Trp Lys
    210                 215
```

Another suitable nucleic acid molecule in accordance with the present invention encodes for a protein or polypeptide having activity as a polygalacturonase (PG), isolated from *Carica papaya*, which has a nucleotide sequence corresponding to SEQ ID NO: 9, as follows:

```
gggacggggg atgattgtat ctcgttgagt ggtggctctg gaaatatcaa tgtcacaggt  60

gtccagtgtg gccccggtca cggcattagt atcggtagtc ttggaaagtt gaggaatgag  120

gaaaatgtgg ctgggatttt ggtccaaaat tgcgtgtttg aaggtaccac taacggcgtc  180

agcatcaaaa cctgg                                                   195
```

The nucleic acid sequence corresponding to SEQ ID NO: 9 encodes an polygalacturonase isolated from *Carica papaya*, identified herein as PG which has a deduced amino acid sequence corresponding to SEQ ID NO: 10, as follows:

```
Gly Thr Gly Asp Asp Cys Ile Ser Leu Ser Gly Gly Ser Gly Asn Ile
  1               5                  10                  15

Asn Val Thr Gly Val Gln Cys Gly Pro Gly His Gly Ile Ser Ile Gly
             20                  25                  30

Ser Leu Gly Lys Leu Arg Asn Glu Glu Asn Val Ala Gly Ile Leu Val
         35                  40                  45

Gln Asn Cys Val Phe Glu Gly Thr Thr Asn Gly Val Ser Ile Lys Thr
     50                  55                  60

Trp
 65
```

The second DNA molecule in the DNA construct of the present invention encodes a papaya ringspot virus coat protein (PRSV-CP). Preferably, this PRSV-CP is derived from a gene encoding a papaya ringspot virus coat protein from the papaya ringspot virus strains Thailand (TH), Keaau (KE), Kapoho (KA), Mexico (ME), Taiwan (YK), Brazil (BR), Jamaica (JA), Oahu (OA), and Venezuela (VE).

One suitable form of the nucleic acid of the present invention is the coat protein (CP) gene isolated from PRSV-Hawaii, strain Kapoho ("KA"), which has a nucleic acid sequence corresponding to SEQ ID NO: 11 as follows:

```
tccaagaatg aagctgtgga tgctggtttg aatgaaaaac tcaaagagaa agaaagacag  60
aaagaaaaag aaaaagaaaa acaaaaagaa aaaggaaaag acgatgctag tgacgaaaat 120
gatgtgtcaa ctagcacaaa aactggagag agagatagag atgtcaatgt tgggaccagt 180
ggaactttcg ctgttccgag aattaaatca tttactgata agttgattct accaagaatt 240
aagggaaaga ctgtccttaa tttaagtcat cttcttcagt ataatccgca acaaattgac 300
atttctaaca ctcgtgccac tcagtcacaa tttgagaagt ggtatgaggg agtgagggat 360
gattatggcc ttaatgataa tgaaatgcaa gttatgctaa atggtttgat ggtttggtgt 420
atcgagaatg gtacatctcc agacatatct ggtgtatggg ttatgatgga tggggaaacc 480
caagttgatt atccaaccaa gcctttaatt gagcatgata ctccgtcatt taggcaaatt 540
atggctcact ttagtaacgc ggcagaagca tacattgcga agagaaatgc tactgagagg 600
tacatgccgc ggtacggaat caagagaaat ttgactgaca ttagcctcgc tagatatgct 660
ttcgacttct atgaggtgaa ttcgaaaaca cctgataggg ctcgcgaagc ccacatgcag 720
atgaaggctg cagcgctgcg aaacactagt cgcagaatgt ttggtatgga cggcagtgtt 780
agtaacaagg aagaaaacac ggagagacac acagtggaag atgtcgatag agacatgcac 840
tctctcctgg gtatgcgcaa ctaa                                        864
```

The present invention also relates to the PRSV-KA coat protein, encoded by the nucleotide corresponding to SEQ ID NO: 11, where the protein encoded has an amino acid sequence corresponding to SEQ ID NO: 12, as follows:

```
Ser Lys Asn Glu Ala Val Asp Ala Gly Leu Asn Glu Lys Leu Lys Glu
 1               5                  10                  15

Lys Glu Arg Gln Lys Glu Lys Glu Lys Glu Lys Gln Lys Glu Lys Gly
            20                  25                  30

Lys Asp Asp Ala Ser Asp Glu Asn Asp Val Ser Thr Ser Thr Lys Thr
        35                  40                  45

Gly Glu Arg Asp Arg Asp Val Asn Val Gly Thr Ser Gly Thr Phe Ala
    50                  55                  60

Val Pro Arg Ile Lys Ser Phe Thr Asp Lys Leu Ile Leu Pro Arg Ile
65                  70                  75                  80

Lys Gly Lys Thr Val Leu Asn Leu Ser His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Asp Thr Pro Ser
                165                 170                 175
```

-continued

```
Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
            245                 250                 255

Asp Gly Ser Val Ser Asn Lys Glu Glu Asn Thr Glu Arg His Thr Val
            260                 265                 270

Glu Asp Val Asp Arg Asp Met His Ser Leu Leu Gly Met Arg Asn
        275                 280                 285
```

Another suitable viral CP gene of the present invention is an isolated nucleic acid molecule encoding a CP isolated from the Thailand ("TH") strain of PRSV, which has a nucleic acid sequence corresponding to SEQ ID NO: 13 as follows:

```
tccaagaatg aagctgtgga tgctggtctt aatgagaagt tcaaagataa agaaaaacag  60

aaagaagaaa aagataaaca aaaaggtaaa gaaaataatg aagctagtga cggaaatgat  120

gtgtcaacta gcacaaaaac tggagagaga gatagagatg tcaatgccgg aactagtggt  180

actttcactg ttccgagaat aaaattattt accgacaaga tgattttacc aagaattaag  240

ggaaaaactg tccttagttt aaatcatctt cttcagtata atccgcaaca aatagacatc  300

tcaaacactc gtgccactca atctcaattc gaaaagtggt atgagggagt gaggaatgat  360

tacggtctta atgataacga aatgcaagtg atgttaaatg gtttgatggt ttggtgcatc  420

gaaaatggaa catccccaga catatctggt gtctgggtga tgatggatgg ggaaacccaa  480

gtcgattatc ccatcaagcc tttgatcgaa catgcaactc cttcgttcag gcaaatcatg  540

gctcacttca gtaacgcggc agaggcatac atcgcaaaga ggaatgctac tgagaggtac  600

atgccgcggt atggaatcaa gaggaatctg actgacatta gtctcgctag atatgctttc  660

gacttctatg aggtgaactc aaaaacacct gatagggctc gtgaagctca tatgcagatg  720

aaggctgcag cgctgcgcaa cactgatcgc agaatgtttg gaatggacgg cagtgtcagt  780

aacaaggaag aaaacacgga gagacacaca gtggaagatg tcaacagaga catgcactct  840

ctcctaggta tgcgcaattg a                                            861
```

The present invention also relates to the viral coat protein of the TH strain of PRSV, which corresponds to amino acid SEQ ID NO: 14, as follows:

```
Ser Lys Asn Glu Ala Val Asp Ala Gly Leu Asn Glu Lys Phe Lys Asp
  1               5                  10                  15

Lys Glu Lys Gln Lys Glu Glu Lys Asp Lys Gln Lys Gly Lys Glu Asn
            20                  25                  30

Asn Glu Ala Ser Asp Gly Asn Asp Val Ser Thr Ser Thr Lys Thr Gly
        35                  40                  45

Glu Arg Asp Arg Asp Val Asn Ala Gly Thr Ser Gly Thr Phe Thr Val
    50                  55                  60
```

-continued

```
Pro Arg Ile Lys Leu Phe Thr Asp Lys Met Ile Leu Pro Arg Ile Lys
65                  70                  75                  80

Gly Lys Thr Val Leu Ser Leu Asn His Leu Leu Gln Tyr Asn Pro Gln
                85                  90                  95

Gln Ile Asp Ile Ser Asn Thr Arg Ala Thr Gln Ser Gln Phe Glu Lys
            100                 105                 110

Trp Tyr Glu Gly Val Arg Asn Asp Tyr Gly Leu Asn Asp Asn Glu Met
        115                 120                 125

Gln Val Met Leu Asn Gly Leu Met Val Trp Cys Ile Glu Asn Gly Thr
    130                 135                 140

Ser Pro Asp Ile Ser Gly Val Trp Val Met Met Asp Gly Glu Thr Gln
145                 150                 155                 160

Val Asp Tyr Pro Ile Lys Pro Leu Ile Glu His Ala Thr Pro Ser Phe
                165                 170                 175

Arg Gln Ile Met Ala His Phe Ser Asn Ala Ala Glu Ala Tyr Ile Ala
            180                 185                 190

Lys Arg Asn Ala Thr Glu Arg Tyr Met Pro Arg Tyr Gly Ile Lys Arg
        195                 200                 205

Asn Leu Thr Asp Ile Ser Leu Ala Arg Tyr Ala Phe Asp Phe Tyr Glu
    210                 215                 220

Val Asn Ser Lys Thr Pro Asp Arg Ala Arg Glu Ala His Met Gln Met
225                 230                 235                 240

Lys Ala Ala Ala Leu Arg Asn Thr Asp Arg Arg Met Phe Gly Met Asp
                245                 250                 255

Gly Ser Val Ser Asn Lys Glu Glu Asn Thr Glu Arg His Thr Val Glu
            260                 265                 270

Asp Val Asn Arg Asp Met His Ser Leu Leu Gly Met Arg Asn
        275                 280                 285
```

Also suitable as a nucleic acid for use in the present invention is the nucleic acid which encodes a CP isolated from the Keaau ("KE") strain of PRSV. PRSV-KE contains two "cut-sites," i.e., two potential cleavage sites for a coat protein. The first cleavage site sequence in the KE strain of PRSV, identified herein as KE-CP1, corresponds to SEQ ID NO: 15, as follows:

```
tcaaggagca ctgatgatta tcaacttgtt tggagtgaca atacacatgt gtttcatcag  60
tccaagaatg aagctgtgga tgctggtttg aatgaaaaac tcaaagagaa agaaaaacag  120
aaagaaaaag aaaaagaaaa acaaaaagaa aaaggaagag acgatgctag tgacgaaaat  180
gatgtgtcaa ctagcacaaa aactggagag agagatagag atgtcaatgt tgggaccagt  240
ggaactttcg ctgttccgag aattaaatca tttactgata agttgattct accaagaatt  300
aagggaaaga ctgtccttaa tttaagtcat cttcttcagt ataatccgca acaaattgac  360
atttctaaca ctcgtgccac tcagtcacaa tttgagaagt ggtatgaggg agtgagggat  420
gattatggcc ttaatgataa tgaaatgcaa gttatgctaa atggtttgat ggtttggtgt  480
atcgagaatg gtacatctcc agacatatct ggtgtatggg ttatgatgga tggggaaacc  540
caagttgatt atccaaccaa gcctttaatt gagcatgcta ctccgtcatt taggcaaatt  600
atggctcact ttagtaacgc ggcagaagca tacattgcga agagaaatgc tactgagagg  660
tacatgccgc ggtacggaat caagagaaat ttgactgacg ttagcctcgc tagatatgct  720
ttcgacttct atgaggtgaa ttcgaaaaca cctgataggg ctcgcgaagc ccacatgcag  780
atgaaggctg cagcgctgcg aaacactagt cgcagaatgt ttggtatgga cggcagtgtt  840
```

-continued

```
agtaacaagg aagaaaacac ggagagacac acagtggaag atgtcaatag agacatgcac  900

tctctcctgg gcatgcgcaa c                                            921
```

A second nucleotide sequence encoding a PRSV-KE coat protein sequence, which starts from the second KE-CP cleavage site, is identified as KE-CP2 herein, and corresponds to SEQ ID. No. 16, as follows:

```
tccaagaatg aagctgtgga tgctggtttg aatgaaaaac tcaaagagaa agaaaaacag   60

aaagaaaaag aaaaagaaaa acaaaaagaa aaaggaaaag acgatgctag tgacgaaaat  120

gatgtgtcaa ctagcacaaa aactggagag agagatagag atgtcaatgt tgggaccagt  180

ggaactttcg ctgttccgag aattaaatca tttactgata agttgattct accaagaatt  240

aagggaaaga ctgtccttaa tttaagtcat cttcttcagt ataatccgca acaaattgac  300

atttctaaca ctcgtgccac tcagtcacaa tttgagaagt ggtatgaggg agtgagggat  360

gattatggcc ttaatgataa tgaaatgcaa gttatgctaa atggtttgat ggtttggtgt  420

atcgagaatg gtacatctcc agacatatct ggtgtatggg ttatgatgga tggggaaacc  480

caagttgatt atccaaccaa gcctttaatt gagcatgcta ctccgtcatt taggcaaatt  540

atggctcact ttagtaacgc ggcagaagca tacattgcga agagaaatgc tactgagagg  600

tacatgccgc ggtacggaat caagagaaat ttgactgacg ttagcctcgc tagatatgct  660

ttcgacttct atgaggtgaa ttcgaaaaca cctgataggg ctcgcgaagc ccacatgcag  720

atgaaggctg cagcgctgcg aaacactagt cgcagaatgt ttggtatgga cggcagtgtt  780

agtaacaagg aagaaaacac ggagagacac acagtggaag atgtcaatag agacatgcac  840

tctctcctgg gcatgcgcaa ctaa                                         864
```

The nucleic acid sequence corresponding to SEQ ID NO: 15 encodes a PRSV coat protein identified herein as KE-CP1, which has an amino acid sequence corresponding to SEQ ID. No. 17, as follows:

```
Ser Arg Ser Thr Asp Asp Tyr Gln Leu Val Trp Ser Asp Asn Thr His
  1               5                  10                  15

Val Phe His Gln Ser Lys Asn Glu Ala Val Asp Ala Gly Leu Asn Glu
             20                  25                  30

Lys Leu Lys Glu Lys Glu Lys Gln Lys Glu Lys Glu Lys Glu Lys Gln
         35                  40                  45

Lys Glu Lys Gly Arg Asp Asp Ala Ser Asp Glu Asn Asp Val Ser Thr
     50                  55                  60

Ser Thr Lys Thr Gly Glu Arg Asp Arg Asp Val Asn Val Gly Thr Ser
 65                  70                  75                  80

Gly Thr Phe Ala Val Pro Arg Ile Lys Ser Phe Thr Asp Lys Leu Ile
                 85                  90                  95

Leu Pro Arg Ile Lys Gly Lys Thr Val Leu Asn Leu Ser His Leu Leu
            100                 105                 110

Gln Tyr Asn Pro Gln Gln Ile Asp Ile Ser Asn Thr Arg Ala Thr Gln
        115                 120                 125

Ser Gln Phe Glu Lys Trp Tyr Glu Gly Val Arg Asp Asp Tyr Gly Leu
    130                 135                 140

Asn Asp Asn Glu Met Gln Val Met Leu Asn Gly Leu Met Val Trp Cys
```

-continued

```
145                 150                 155                 160

Ile Glu Asn Gly Thr Ser Pro Asp Ile Ser Gly Val Trp Val Met Met
                165                 170                 175

Asp Gly Glu Thr Gln Val Asp Tyr Pro Thr Lys Pro Leu Ile Gln His
            180                 185                 190

Ala Thr Pro Ser Phe Arg Gln Ile Met Ala His Phe Ser Asn Ala Ala
        195                 200                 205

Glu Ala Tyr Ile Ala Lys Arg Asn Ala Thr Glu Arg Tyr Met Pro Arg
    210                 215                 220

Tyr Gly Ile Lys Arg Asn Leu Thr Asp Val Ser Leu Ala Arg Tyr Ala
225                 230                 235                 240

Phe Asp Phe Tyr Glu Val Asn Ser Lys Thr Pro Asp Arg Ala Arg Glu
                245                 250                 255

Ala His Met Gln Met Lys Ala Ala Ala Leu Arg Asn Thr Ser Arg Arg
            260                 265                 270

Met Phe Gly Met Asp Gly Ser Val Ser Asn Lys Glu Glu Asn Thr Glu
        275                 280                 285

Arg His Thr Val Glu Asp Val Asn Arg Asp Met His Ser Leu Leu Gly
    290                 295                 300

Met Arg Asn
305
```

SEQ ID NO: 16 encodes a CP of KE strain identified herein as KE-CP2, with an amino acid sequence which corresponds to SEQ ID NO: 18, as follows:

```
Ser Lys Asn Glu Ala Val Asp Ala Gly Leu Asn Glu Lys Leu Lys Glu
  1               5                  10                  15

Lys Glu Lys Gln Lys Glu Lys Glu Lys Glu Lys Gln Lys Glu Lys Gly
            20                  25                  30

Lys Asp Asp Ala Ser Asp Glu Asn Asp Val Ser Thr Ser Thr Lys Thr
        35                  40                  45

Gly Glu Arg Asp Arg Asp Val Asn Val Gly Thr Ser Gly Thr Phe Ala
     50                  55                  60

Val Pro Arg Ile Lys Ser Phe Thr Asp Lys Leu Ile Leu Pro Arg Ile
 65                  70                  75                  80

Lys Gly Lys Thr Val Leu Asn Leu Ser His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Val Ser Leu Ala Arg Tyr Ala Phe Asp Phe Tyr
```

-continued

```
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

Also suitable in the present invention is the nucleic acid which encodes a CP isolated from the Taiwan ("YK") strain of PRSV, and corresponds to SEQ ID NO: 19, as follows:

```
tctaaaaatg aagctgtgga taccggtctg aatgagaagc tcaaagaaaa agaaaagcag  60

aaagaaaaag aaaaagataa acaacaagat aaagacaatg atggagctag tgacggaaac  120

gatgtgtcaa ctagcacaaa aactggagag agagataggg atgtcaatgc cggaactagt  180

ggaaccttca ctgttccgag gataaagtca tttactgata agatgatctt accaagaatt  240

aagggaaaaa ctgtccttaa tttaaatcat cttcttcagt ataatccgaa acaagttgac  300

atctcaaaca ctcgcgccac tcaatctcaa tttgagaagt ggtatgaggg agtgagaaat  360

gattatggcc ttaatgataa cgaaatgcaa gtaatgttaa atggtttgat ggtttggtgt  420

atcgaaaatg gtacatctcc agatatatct ggtgtctggg ttatgatgga tggggaaacc  480

caagtcgatt atcccattaa acctttgatt gaacacgcaa ctccttcatt taggcaaatc  540

atggctcact tcagtaacgc ggcagaggca tacatcgcga agaggaatgc aactgagaag  600

tacatgccgc ggtatggaat caagagaaat ttgactgaca ttagtctcgc tagatatgct  660

ttcgatttct atgaggtgaa ttcgaaaaca cctgataggg ctcgtgaagc tcatatgcag  720

atgaaggctg cagcgctacg caatactaat cgcaaaatgt ttggaatgga cggcagtgtc  780

agtaacaagg aagaaaacac ggagagacac acagtggaag atgtcaacag agacatgcac  840

tctctcctgg gtatgcgcaa ttga                                         864
```

SEQ ID NO: 19 encodes the CP of the YK strain of PRSV which has an amino acid sequence corresponding to SEQ ID NO: 20, as follows:

```
Ser Lys Asn Glu Ala Val Asp Thr Gly Leu Asn Glu Lys Leu Lys Glu
  1               5                  10                  15

Lys Glu Lys Gln Lys Glu Lys Glu Lys Asp Lys Gln Gln Asp Lys Asp
            20                  25                  30

Asn Asp Gly Ala Ser Asp Gly Asn Asp Val Ser Thr Ser Thr Lys Thr
        35                  40                  45

Gly Glu Arg Asp Arg Asp Val Asn Ala Gly Thr Ser Gly Thr Phe Thr
    50                  55                  60

Val Pro Arg Ile Lys Ser Phe Thr Asp Lys Met Ile Leu Pro Arg Ile
 65                  70                  75                  80

Lys Gly Lys Thr Val Leu Asn Leu Asn His Leu Leu Gln Tyr Asn Pro
                85                  90                  95

Lys Gln Val Asp Ile Ser Asn Thr Arg Ala Thr Gln Ser Gln Phe Glu
            100                 105                 110
```

-continued

```
Lys Trp Tyr Glu Gly Val Arg Asn Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Lys Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Asn Arg Lys Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

Another nucleic acid suitable in the present invention is the nucleic acid which encodes a CP isolated from the Mexico ("ME") strain of PRSV and corresponds to SEQ ID NO: 21, as follows:

```
tccaagaatg aagctgtgga tgctggtttg aatgaaaaac tcaaagaaaa agaaaaacag  60

aaagaaaaag aaaaacaaaa agaaaaagaa aaagacaatg ctagtgacgg aaatgatgtg  120

tcgactagca caaaaactgg agagaaagat agagatgtca atgtcggaac tagtggaact  180

ttcactgttc cgagaattaa atcatttact gataagatga ttctaccgag aattaaggga  240

aagactgtcc ttaatttaaa tcatcttctt cagtataatc cgcaacaaat tgatatttct  300

aacactcgtg ccactcagtc acaatttgag aaatggtatg agggagtgag gaatgattat  360

ggtctgaatg ataatgaaat gcaagtgatg ctgaatggct tgatggtttg gtgtatcgag  420

aatggtacat ctccagacat atctggtgtt tgggttatga tggatgggga aattcaagtt  480

gactatccaa tcaagcctct aattgagcat gctacccogt catttaggca gattatggct  540

cactttagta acgcggcaga agcatatatt gcaaagagaa atgccactga gaggtacatg  600

ccgcggtatg gaatcaagag aaatttgact gacattagcc tcgctaggta cgctttcgat  660

ttctatgagg ttaattcgaa aacacctgat agggctcgcg aagctcacat gcagatgaaa  720

gctgcagcgc tgcgaaacac tagtcgcaga atgtttggta tgggcggcag tgttagtaac  780

aaggaagaaa acacggaaag acacacagtg gaagatgtca atagagacat gcactctctc  840

ctgggtatgc gcaac                                                    855
```

SEQ ID NO: 21 encodes the CP of the ME strain of PRSV which has an amino acid sequence corresponding to SEQ ID NO: 22, as follows:

```
Ser Lys Asn Glu Ala Val Asp Ala Gly Leu Asn Glu Lys Leu Lys Glu
  1               5                  10                  15

Lys Glu Lys Gln Lys Glu Lys Glu Lys Gln Lys Glu Lys Glu Lys Asp
             20                  25                  30

Asn Ala Ser Asp Gly Asn Asp Val Ser Thr Ser Thr Lys Thr Gly Glu
        35                  40                  40                  45

Lys Asp Arg Asp Val Asn Val Gly Thr Ser Gly Thr Phe Thr Val Pro
     50                  55                  60

Arg Ile Lys Ser Phe Thr Asp Lys Met Ile Leu Pro Arg Ile Lys Gly
 65                  70                  75                  80

Lys Thr Val Leu Asn Leu Asn His Leu Leu Gln Tyr Asn Pro Gln Gln
                 85                  90                  95

Ile Asp Ile Ser Asn Thr Arg Ala Thr Gln Ser Gln Phe Glu Lys Trp
            100                 105                 110

Tyr Glu Gly Val Arg Asn Asp Tyr Gly Leu Asn Asp Asn Glu Met Gln
        115                 120                 125

Val Met Leu Asn Gly Leu Met Val Trp Cys Ile Glu Asn Gly Thr Ser
    130                 135                 140

Pro Asp Ile Ser Gly Val Trp Val Met Met Asp Gly Glu Ile Gln Val
145                 150                 155                 160

Asp Tyr Pro Ile Lys Pro Leu Ile Glu His Ala Thr Pro Ser Phe Arg
                165                 170                 175

Gln Ile Met Ala His Phe Ser Asn Ala Ala Glu Ala Tyr Ile Ala Lys
            180                 185                 190

Arg Asn Ala Thr Glu Arg Tyr Met Pro Arg Tyr Gly Ile Lys Arg Asn
        195                 200                 205

Leu Thr Asp Ile Ser Leu Ala Arg Tyr Ala Phe Asp Phe Tyr Glu Val
    210                 215                 220

Asn Ser Lys Thr Pro Asp Arg Ala Arg Glu Ala His Met Gln Met Lys
225                 230                 235                 240

Ala Ala Ala Leu Arg Asn Thr Ser Arg Arg Met Phe Gly Met Gly Gly
              245                 250                 255

Ser Val Ser Asn Lys Glu Glu Asn Thr Glu Arg His Thr Val Glu Asp
            260                 265                 270

Val Asn Arg Asp Met His Ser Leu Leu Gly Met Arg Asn
        275                 280                 285
```

Another nucleic acid suitable in the present invention is the nucleic acid which encodes a CP isolated from the Brazil ("BR") strain of PRSV and corresponds to SEQ ID NO: 23, as follows:

```
tccaaaaatg aagctgtgga tgctggtttg aatgaaaagc gtaaagaaca agagaaacaa  60

gaagaaaaag aagaaaaaca aaaaaagaaa gaaaaagacg atgctagtta cggaaacgat  120

gtgtcaacta gcacaagaac tggagagaga gacagagatg tcaatgttgg gaccagtgga  180

actttcactg ttccgagaac aaaatcattt actgataaga tgattttacc tagaattaag  240

ggaaaaactg tccttaattt aaatcatctg attcagtata atccgcaaca aattgacatt  300

tctaacactc gtgctactca atcacaattt gagaagtggt acgagggagt gaggaatgat  360
```

-continued

```
tatggcctta atgataatga gatgcaaata gtgctaaatg gtttgatggt ttggtgtatc  420

gaaaacggta catctccaga catatctggt gcctgggtta tgatggatgg ggaaacccag  480

gttgactatc caatcaagcc tttaattgag catgctactc cgtcgtttag gcaaattatg  540

gctcatttca gtaacgcggc agaagcatac attacaaaga gaaatgctac tgagaggtac  600

atgccgcggt atgggatcaa gagaaatttg actyacatta gtcttgctag atatgctttc  660

gatttctatg aggtgaattc gaaaacacct gatagggctc gcgaagctca catgcagatg  720

aaagctgcag cgctgcgaaa cactaatcgc agaatgtttg gtatggacgg cagtgttagt  780

aacaaggaag aaaacacgga gagacacaca gtggaagatg tcaatagaga catgcactct  840

ctcctgggta tgcgcaactg a                                             861
```

SEQ ID NO: 23 encodes the CP of the BR strain of PRSV which has an amino acid sequence corresponding to SEQ ID NO: 24, as follows:

```
Ser Lys Asn Glu Ala Val Asp Ala Gly Leu Asn Glu Lys Arg Lys Glu
  1               5                  10                  15

Gln Glu Lys Gln Glu Glu Lys Glu Glu Lys Gln Lys Lys Lys Glu Lys
                 20                  25                  30

Asp Asp Ala Ser Tyr Gly Asn Asp Val Ser Thr Ser Thr Arg Thr Gly
         35                  40                  45

Glu Arg Asp Arg Asp Val Asn Val Gly Thr Ser Gly Thr Phe Thr Val
     50                  55                  60

Pro Arg Thr Lys Ser Phe Thr Asp Lys Met Ile Leu Pro Arg Ile Lys
 65                  70                  75                  80

Gly Lys Thr Val Leu Asn Leu Asn His Leu Ile Gln Tyr Asn Pro Gln
                 85                  90                  95

Gln Ile Asp Ile Ser Asn Thr Arg Ala Thr Gln Ser Gln Phe Glu Lys
            100                 105                 110

Trp Tyr Glu Gly Val Arg Asn Asp Tyr Gly Leu Asn Asp Asn Glu Met
        115                 120                 125

Gln Ile Val Leu Asn Gly Leu Met Val Trp Cys Ile Glu Asn Gly Thr
    130                 135                 140

Ser Pro Asp Ile Ser Gly Val Trp Val Met Met Asp Gly Glu Thr Gln
145                 150                 155                 160

Val Asp Tyr Pro Ile Lys Pro Leu Ile Glu His Ala Thr Pro Ser Phe
                165                 170                 175

Arg Gln Ile Met Ala His Phe Ser Asn Ala Ala Glu Ala Tyr Ile Thr
            180                 185                 190

Lys Arg Asn Ala Thr Glu Arg Tyr Met Pro Arg Tyr Gly Ile Lys Arg
        195                 200                 205

Asn Leu Thr Asp Ile Ser Leu Ala Arg Tyr Ala Phe Asp Phe Tyr Glu
    210                 215                 220

Val Asn Ser Lys Thr Pro Asp Arg Ala Arg Glu Ala His Met Gln Met
225                 230                 235                 240

Lys Ala Ala Ala Leu Arg Asn Thr Asn Arg Arg Met Phe Gly Met Asp
                245                 250                 255

Gly Ser Val Ser Asn Lys Glu Glu Asn Thr Glu Arg His Thr Val Glu
            260                 265                 270

Asp Val Asn Arg Asp Met His Ser Leu Leu Gly Met Arg Asn
        275                 280                 285
```

Another nucleic acid suitable in the present invention is the nucleic acid which encodes a CP isolated from the Jamaica ("JA") strain of PRSV and corresponds to SEQ ID NO: 25, as follows:

```
tctaaaaatg aagctgtgga tgctggttta aatgaaaagc tcaaagaaaa agaaaaacag  60

aaagataaag aaaaagaaaa acaaaaagat aaagaaaaag gagatgctag tgacggaaat  120

gatggttcga ctagcacaaa aactggagag agagatagag atgtcaatgt tgggaccagt  180

ggaacttcca ctgttccgag aattaaatca ttcactgata agatggttct accaagaatt  240

aagggaaaaa ctgtccttaa tttaaatcat cttcttcagt ataatccaca acaaattgac  300

atttctaaca ctcgtgccac tcagtcacaa tttgagaagt ggtacgaagg agtgaggagt  360

gattatggcc taaatgatag tgaaatgcaa gtgacgctaa atggcttgat ggtttggtgt  420

atcgagaatg gtacatctcc agacatatct ggtgtctggg ttatgatgga tggggaaacc  480

caagttgatt atccaatcaa gcctttaatt gagcacgcta ccccatcatt taggcagatt  540

atggctcact tcagtaacgc ggcagaagca tacactgcaa agagaaatgc tactgagagg  600

tacatgccgc ggtatggaat caagagaaat ttgactgaca ttagtctcgc tagatacgct  660

ttcgatttct atgaggtgaa ttcgaagaca cctgataggg ctcgtgaagc tcacatgcag  720

atgaaagctg cagcgctgcg aaacactaat cgcagaatgt ttggtatgga cggcagtgtt  780

agtaacaatg aagaaaacac ggagagacac acagtggaag atgtctatat agacatgcac  840

tctctcctgc gtttgcgcaa ctga                                        864
```

SEQ ID NO: 25 encodes the CP of the JA strain of PRSV which has an amino acid sequence corresponding to SEQ ID NO: 26, as follows:

```
Ser Lys Asn Glu Ala Val Asp Ala Gly Leu Asn Glu Lys Leu Lys Glu
 1               5                  10                  15

Lys Glu Lys Gln Lys Asp Lys Glu Lys Glu Lys Gln Lys Asp Lys Glu
            20                  25                  30

Lys Gly Asp Ala Ser Asp Gly Asn Asp Gly Ser Thr Ser Thr Lys Thr
        35                  40                  45

Gly Glu Arg Asp Arg Asp Val Asn Val Gly Thr Ser Gly Thr Ser Thr
    50                  55                  60

Val Pro Arg Ile Lys Ser Phe Thr Asp Lys Met Val Leu Pro Arg Ile
65                  70                  75                  80

Lys Gly Lys Thr Val Leu Asn Leu Asn His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Ser Asp Tyr Gly Leu Asn Asp Ser Glu
        115                 120                 125

Met Gln Val Thr Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Thr
            180                 185                 190

Ala Lys Arg Asn Ala Thr Glu Arg Tyr Met Pro Arg Tyr Gly Ile Lys
        195                 200                 205
```

-continued

Arg Asn Leu Thr Asp Ile Ser Leu Ala Arg Tyr Ala Phe Asp Phe Tyr
210 215 220

Glu Val Asn Ser Lys Thr Pro Asp Arg Ala Arg Glu Ala His Met Gln
225 230 235 240

Met Lys Ala Ala Ala Leu Arg Asn Thr Asn Arg Arg Met Phe Gly Met
245 250 255

Asp Gly Ser Val Ser Asn Asn Glu Glu Asn Thr Glu Arg His Thr Val
260 265 270

Glu Asp Val Tyr Ile Asp Met His Ser Leu Leu Arg Leu Arg Asn
275 280 285

Another nucleic acid suitable in the present invention is the nucleic acid which encodes a CP isolated from the Oahu ("OA") strain of PRSV and corresponds to SEQ ID NO: 27, as follows:

tccaagaatg aagctgtgga tgctggtttg aatgaaaaat tcaaagagaa ggaaaaacag 60
aaagaaaaag aaaaagaaaa acaaaaagag aaagaaaaag atggtgctag tgacgaaaat 120
gatgtgtcaa ctagcacaaa aactggagag agagatagag atgtcaatgt cgggaccagt 180
ggaactttca cagttccgag aattaaatca tttactgata agatgattct accgagaatt 240
aaggggaagg ctgtccttaa tttaaatcat cttcttcagt acaatccgca acaaatcgac 300
atttctaaca ctcgtgccgc tcattcacaa tttgaaaagt ggtatgaggg agtgaggaat 360
gattatgccc ttaatgataa tgaaatgcaa gtgatgctaa atggtttgat ggtttggtgt 420
atcgagaatg gtacatctcc agacatatct ggtgtctggg taatgatgga tggggaaacc 480
caagtcgatt atccaatcaa gcctttgatt gagcatgcta ctccgtcatt taggcaaatt 540
atggctcact ttagtaacgc ggcagaagca tacattgcga agagaaatgc tactgagagg 600
tacatgccgc ggtatggaat caagagaaat ttgactgaca ttagcctcgc tagatacgct 660
ttcgactttt atgaggtgaa ttcgaaaaca cctgatagag ctcgcgaagc tcacatgcag 720
atgaaggctg cagcgctgcg aaacaccagt cgcagaatgt ttggtatgga cggcagtgtt 780
agtaacaagg aagaaaacac ggagagacac acagtggaag atgtcaatag agacatgcac 840
tctctcctgg gtatgcgcaa ctaa 864

SEQ ID NO: 27 encodes the CP of the OA strain of PRSV which has an amino acid sequence corresponding to SEQ ID NO: 28, as follows:

Ser Lys Asn Glu Ala Val Asp Ala Gly Leu Asn Glu Lys Phe Lys Glu
1 5 10 15

Lys Glu Lys Gln Lys Glu Lys Glu Lys Glu Lys Gln Lys Glu Lys Glu
20 25 30

Lys Asp Gly Ala Ser Asp Glu Asn Asp Val Ser Thr Ser Thr Lys Thr
35 40 45

Gly Glu Arg Asp Arg Asp Val Asn Val Gly Thr Ser Gly Thr Phe Thr
50 55 60

Val Pro Arg Ile Lys Ser Phe Thr Asp Lys Met Ile Leu Pro Arg Ile
65 70 75 80

Lys Gly Lys Ala Val Leu Asn Leu Asn His Leu Leu Gln Tyr Asn Pro
85 90 95

-continued

```
Gln Gln Ile Asp Ile Ser Asn Thr Arg Ala Ala His Ser Gln Phe Glu
            100                 105                 110

Lys Trp Tyr Glu Gly Val Arg Asn Asp Tyr Ala Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

Another nucleic acid suitable in the present invention is the nucleic acid which encodes a CP isolated from the Venezuela ("VE") strain of PRSV and corresponds to SEQ ID NO: 29, as follows:

```
atggctgtgg atgctggttt gaatgggaag ctcaaagaaa aagagaaaaa agaaaaagaa  60

aaagaaaaac agaaagagaa agagaaagat gatgctagtg acggaaatga tgtgtcaact  120

agcacaaaaa ctggagagag agatagagat gtcaatattg ggaccagtgg aactttcact  180

gtccctagga ttaaatcatt tactgataag atgattttac cgagaattaa gggaaagact  240

gtccttaatt taaatcatct tcttcagtat aatccgaaac aaattgacat ttctaatact  300

cgtgccactc agtcgcaatt tgagaaatgg tatgagggag tgagggatga ttatggcctt  360

aatgataatg aaatgcaagt gatgctaaat ggcttgatgg tttggtgcat tgagaatggt  420

acatctccag acatatctgg tgtttgggtt atggtggatg gggaaaccca agttgattat  480

ccaatcaagc ctttaattga gcatgctaca ccgtcattta ggcaaattat ggctcatttt  540

agtaacgcgg cagaagcata cattgcgatg agaaatgcta ctgagaggta catgccgcgg  600

tatggaatca agagaaattt gactgacatc aacctagctc gatacgcttt tgatttctat  660

gaggtgaatt cgaaaacmcc tgatagggct cgtgaagctc acatgcagat gaaggctgca  720

gctttgcgaa acactaatcg cagaatgttt gytatcgacg gcagtgttag caacaaggaa  780

gaaaacacgg agagacacac agtggatgat gtcaatagag acatgcactc tctcctgggt  840

atgcgcaact aaatactcgc acttgtgtgt ttgtcgagcc tgact                   885
```

SEQ ID NO: 29 encodes the CP of the VE strain of PRSV which has an amino acid sequence corresponding to SEQ ID NO: 30, as follows:

```
Met Ala Val Asp Ala Gly Leu Asn Gly Lys Leu Lys Glu Lys Glu Lys
  1               5                  10                  15

Lys Glu Lys Glu Lys Glu Lys Gln Lys Glu Lys Glu Lys Asp Asp Ala
             20                  25                  30

Ser Asp Gly Asn Asp Val Ser Thr Ser Thr Lys Thr Gly Glu Arg Asp
         35                  40                  45

Arg Asp Val Asn Ile Thr Ser Gly Thr Phe Thr Val Pro Arg Ile Lys
     50                  55                  60

Ser Phe Thr Asp Lys Met Ile Leu Pro Arg Ile Lys Gly Lys Thr Val
 65                  70                  75                      80

Leu Asn Leu Asn His Leu Leu Gln Tyr Asn Pro Lys Gln Ile Asp Ile
                 85                  90                  95

Ser Asn Thr Arg Ala Thr Gln Ser Gln Phe Glu Lys Trp Tyr Glu Gly
            100                 105                 110

Val Arg Asp Asp Tyr Gly Leu Asn Asp Asn Glu Met Gln Val Met Leu
        115                 120                 125

Asn Gly Leu Met Val Trp Cys Ile Glu Asn Gly Thr Ser Pro Asp Ile
    130                 135                 140

Ser Gly Val Trp Val Met Val Asp Gly Glu Thr Gln Val Asp Tyr Pro
145                 150                 155                 160

Ile Lys Pro Leu Ile Glu His Ala Thr Pro Ser Phe Arg Gln Ile Met
                165                 170                 175

Ala His Phe Ser Asn Ala Ala Glu Ala Tyr Ile Ala Met Arg Asn Ala
            180                 185                 190

Thr Glu Arg Tyr Met Pro Arg Tyr Gly Ile Lys Arg Asn Leu Thr Asp
        195                 200                 205

Ile Asn Leu Ala Arg Tyr Ala Phe Asp Phe Tyr Glu Val Asn Ser Lys
    210                 215                 220

Xaa Pro Asp Arg Ala Arg Glu Ala His Met Gln Met Lys Ala Ala Ala
225                 230                 235                 240

Leu Arg Asn Thr Asn Arg Arg Met Phe Gly Ile Asp Gly Ser Val Ser
                245                 250                 255

Asn Lys Glu Glu Asn Thr Glu Arg His Thr Val Asp Asp Val Asn Arg
            260                 265                 270

Asp Met His Ser Leu Leu Gly Met Arg Asn
        275                 280
```

Also suitable in the present invention are other forms of the nucleic acid molecules shown above. An example of a nucleic acid suitable in the present invention is a nucleic acid molecule which has a nucleotide sequence that is at least 85% similar by basic BLAST using default parameters analysis to the nucleotide sequence of SEQ ID NOS: 1, 3, 5, 7, and 9, and which hybridizes to the nucleotide sequence of SEQ ID NOS: 1, 3, 5, 7, and 9, under stringent conditions characterized by a hybridization buffer comprising 5×SSC buffer at a temperature of about 42–56° C. A further example of nucleic acids suitable in the present invention is any nucleic acid which has a nucleotide sequence that is at least 85% similar by basic BLAST using default parameters analysis to the nucleotide sequence of SEQ ID NOS: 11, 13, 15, 16, 19, 21, 23, 25, 27, and 29 of the present invention and which hybridizes to the nucleotide sequence of SEQ ID NOS: 1, 3, 5, 7, 9, 11, 13, 15, 16, 19, 21, 23, 25, 27, and 29 of the present invention under stringent conditions characterized by a hybridization buffer comprising 5×SSC buffer at a temperature of about 42–65° C., preferably 45° C.

Fragments of both PRSV-CP encoding genes and papaya ripening genes are particularly useful in the present invention. Fragments capable of use in the present invention can be produced by several means. In one method, subclones of the gene encoding the CP or papaya ripening genes of choice are produced by conventional molecular genetic manipulation by subcloning gene fragments. In another approach, based on knowledge of the primary structure of the protein, fragments of a PRSV-CP encoding gene and papaya ripening gene of choice may be synthesized by using the PCR technique together with specific sets of primers chosen to represent particular portions of the protein. These, then, would be cloned into an appropriate vector in either the sense or antisense orientation.

Another example of suitable fragments of the nucleic acids of the present invention are fragments of the genes which have been identified as conserved ("con") regions of the CP and papaya ripening proteins, or alternatively, those portions of PRSV-CP nucleotide sequences and papaya ripening nucleotide sequences that have been identified as variable ("var") regions. Sequences identified by standard homology analysis as either variable or conserved in PRSV-CP and papaya ripening gene nucleotide sequences can be amplified using standard PCR methods using forward and reverse primers designed to amplify the region of choice and which include a restriction enzyme sequence included to allow ligation of the PCR product into a vector of choice. Combinations of amplified conserved and variable region sequences can be ligated into a single vector to create a "cassette" which contains a plurality of DNA molecules in one vector. The use of conserved and variable regions of PRSV-CP and papaya ripening genes is further detailed below in the Examples.

The present invention also relates to a DNA construct containing nucleic acids which encode for papaya ripening proteins or polypeptides together with nucleic acids encoding one or more types of PRSV-CP. This involves incorporating the nucleic acid molecules of the present invention into host cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system which includes the necessary elements for the transcription and translation of the inserted protein coding sequences.

The nucleic acid molecules of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley, et al., "Expression of Bacterial Genes in Plant Cells," *Proc. Nat'l Acad. Sci.* 80:4803–4807 (1983), which is hereby incorporated by reference in its entirety).

Further improvement of this technique led to the development of the binary vector system (Bevan, M., "Binary *Agrobacterium Vectors* for Plant Transformation," *Nucleic Acids Res.* 12:8711–8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch, et al., "Complete Sequence of the Binary Vector Bin19," *Plant Molec. Biol.* 27:405–409 (1995), which is hereby incorporated by reference in its entirety). Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase ("NOS") gene promoter, from *Agrobacterium tumefaciens* (U.S. Pat. No. 5,034,322 issued to Rogers et al., which is hereby incorporated by reference in its entirety), the cauliflower mosaic virus ("CaMV") 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter ("ubi"), which is the promoter of a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421–5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421–5 (1991); Aoyama et al., "A Glucocorticoid-Mediated Transcriptional Induction System in Transgenic Plants," *Plant J.* 11: 605–612 (1997), and McNellis et al., "Glucocorticoid-Inducible Expression of a Bacterial Avirulence Gene in Transgenic Arabidopsis Induces Hypersensitive Cell Death, *Plant J.* 14(2):247–57 (1998), which are hereby incorporated by reference in their entirety). In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 issued to Shewmaker et al., which is hereby incorporated by reference in its entirety). In the preferred embodiment of the present invention, a heterologous promoter is linked to the nucleic acid of the construct, where "heterologous promoter" is defined as a promoter to which the nucleic acid of the construct is not linked in nature.

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase ("nos") 3' regulatory region (Fraley, et al., "Expression of Bacterial Genes in Plant Cells," *Proc. Nat'l Acad. Sci. USA* 80:4803–4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus 35S Promoter," Nature 313 (6005):810–812 (1985), which is hereby incorporated by reference in its entirety). Virtually any 3' regulatory region known to be operable in plants would suffice for proper expression of the coding sequence of the nucleic acid of the present invention.

The vector of choice, suitable promoter, and an appropriate 3' regulatory region can be ligated together to produce the expression systems which contain the nucleic acids of the present invention, or suitable fragments thereof, using well known molecular cloning techniques as described in Sambrook et al., *Molecular Cloning: A Laboratory Manual*, Second Edition, Cold Spring Harbor Press, NY (1989), and Ausubel et al. (1989) *Current Protocols in Molecular Biology*, John Wiley & Sons, New York, N.Y., which are hereby incorporated by reference in their entirety.

Once the DNA construct of the present invention has been prepared, it is ready to be incorporated into a host cell. Accordingly, another aspect of the present invention relates to a recombinant host cell containing one or more of the DNA constructs of the present invention containing PRSV-CP-papaya ripening genes. Basically, this method is carried out by transforming a host cell with a DNA construct of the present invention under conditions effective to yield transcription of the DNA molecule in the host cell, using standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the DNA under control of the promoter. Preferably, the nucleic acid construct of the present invention is stably inserted into the genome of the recombinant plant cell as a result of the transformation, although transient expression can serve an important purpose, particularly when the plant under investigation is slow-growing. Plant tissue suitable for transformation include leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue is often achieved by particle bombardment (Klein et al., "High-Velocity Microprojectiles for Delivering Nucleic Acids Into Living Cells," *Nature* 327:70–73 (1987), which is hereby incorporated by reference in its entirety). In this method, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. For papaya, particle gun bombardment has been a particularly successful method (Fitch, M. M., "Stable Transformation of Papaya Via Micro-Projectile Bombardment," *Plant Cell Rep.* 9:189 (1990), and Fitch et al., "Somatic Embryogenesis and Plant Regeneration from Immature Zygotic Embryos of Papaya (*Carica papaya L.*)," *Plant Cell Rep.* 9:320 (1990), which are hereby incorporated by reference in its entirety.) Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign DNA into plant cells. Another approach to transforming plant cells with a gene which imparts resistance to pathogens is particle bombardment (also known as biolistic transformation) of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6–12 (1995), which are hereby incorporated by reference in their entirety. Yet another method of introduction is fusion of protoplasts with other entities, either minicells, cells, lysosomes or other fusible lipid-surfaced bodies (Fraley, et al., *Proc. Natl. Acad. Sci. USA* 79:1859–63 (1982), which is hereby incorporated by reference in its entirety). The DNA molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention. For papaya, see the procedure as described in Cai et al., "A Protocol for Efficient Transformation and Regeneration of *Carica papaya L.* In Vitro," *Cell Devel. Biol-Plant* 35:61–69 (1999), which is hereby incorporated by reference in its entirety.

After transformation, the transformed plant cells must be regenerated. Plant regeneration from cultured protoplasts is described in Evans et al., *Handbook of Plant Cell Cultures, Vol.* 1: (MacMillan Publishing Co., New York, 1983); Vasil I. R. (ed.), *Cell Culture and Somatic Cell Genetics of Plants,* Acad. Press, Orlando, Vol. 1, 1984, and Vol. III (1986), and Fitch et al., "Somatic Embryogenesis and Plant Regeneration from Immature Zygotic Embryos of Papaya (*Carica papaya L.*)," *Plant Cell Rep.* 9:320 (1990), which are hereby incorporated by reference in its entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley, et al., *Proc. Natl. Acad. Sci. USA* 80:4803–4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099–1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901–3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the viral gene by Southern blot hybridization analysis, using a probe specific to the viral genes contained in the given cassette used for transformation (Sambrook et al., "Molecular Cloning: A Laboratory Manual," Cold Spring Harbor, N.Y.: Cold Spring Harbor Press (1989), which is hereby incorporated by reference in its entirety).

The presence of a viral coat protein gene can also be detected by immunological assays, such as the double-antibody sandwich assays described by Namba et al., "Expression of the Gene Encoding the Coat Protein of Cucumber Mosaic Virus (CMV) Strain WL appears to Provide Protection to Tobacco Plants Against Infection by Several Different CMV Strains," *Gene* 107:181–188 (1991) as modified by Clark et al., "Characteristics Of the Microplate Method for Enzyme-Linked Immunosorbent Assay For the Detection of plant Viruses," *J. Gen. Virol.* 34, 475–83 (1977), which are hereby incorporated by reference in their entirety. Potyvirus resistance can also be assayed via infectivity studies as generally described by Namba et al., "Protection of Transgenic Plants Expressing the Coat Protein Gene of Watermelon Virus ii or Zucchini Yellow Mosaic Virus Against Potyviruses," *Phytopath.* 82:940946 (1992), which is hereby incorporated by reference in its entirety, wherein plants are scored as symptomatic when any inoculated leaf shows veinclearing, mosaic, or necrotic symptoms.

After the expression cassette is stably incorporated in transgenic plants, it can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds or propagules (e.g., cuttings) are recovered from the transgenic plants. These seeds can then be planted in the soil and cultivated using conventional procedures to produce transgenic plants.

In one aspect of the present invention, one or more of the nucleic acids of the present invention are inserted into a vector in the sense direction (5'→3'), such that the open reading frame is properly oriented for the expression of the encoded protein under the control of a promoter of choice. Single or multiple nucleic acids of the present invention may be ligated into an appropriate vector in this way under the control of the appropriate heterologous promoter and 3' regulatory region.

In another aspect of the present invention, individual or multiple nucleic acid molecules of the present invention are incorporated into an appropriate vector in either the sense (5'→3') or the antisense orientation (3'→5'), or any combination of the two. This involves inserting one or more of the nucleic acid sequences of the present invention into the restriction sites of a single vector, as described above, under the control of a single promoter with the DNA molecules operably linked 3' to the promoter. The use of antisense RNA to down-regulate the expression of specific plant genes is well known (van der Krol et al., *Nature,* 333:866–869 (1988) and Smith et al., *Nature,* 334:724–726 (1988), which are hereby incorporated by reference in their entirety). Antisense RNA technology involves the production of an RNA molecule that is complementary to the messenger RNA of a target gene; the antisense RNA can potentially block all expression of the targeted gene. Accordingly, both antisense and sense forms of the nucleic acids of the present invention are suitable for use in the DNA constructs of the invention. A single construct may contain both sense and antisense forms of one or more papaya ripening genes. Likewise, both sense and antisense variations of the nucleic acids encoding PRSV-CP and papaya ripening proteins are suitable in the construct of the present invention, as are combinations of one or more papaya ripening genes linked to one or more PRSV-CP genes in any orientation. These constructs generally contain a nucleotide that is translatable into either a sense or antisense mRNA molecule.

Alternatively, the DNA construct of the present invention may be configured so that the DNA molecule encodes a mRNA which is not translatable, i.e., does not result in the production of a protein or polypeptide. This is achieved, for example, by introducing into the desired nucleic acid sequence of the present invention one or more premature stop codons, adding one or more bases (except multiples of 3 bases) to displace the reading frame, and removing the translation initiation codon (U.S. Pat. No. 5,583,021 to Dougherty et al., which is hereby incorporated by reference in its entirety). This can involve the use of a primer to which a stop codon, such as TAATGA, is inserted into the sense (or "forward") PCR-primer for amplification of the full nucleic acid, between the 5' end of that primer, which corresponds to the appropriate restriction enzyme site of the vector into which the nucleic acid is to be inserted, and the 3' end of the primer, which corresponds to the 5' sequence of the enzyme-encoding nucleic acid. Combinations of sense, antisense, translatable and non-translatable variations of the nucleic acids encoding ripening genes and PRSV-CP are suitable for the present invention. Constructs containing nontranslatable versions of the nucleic acids of the present invention may be particularly useful for results which employ PDR as a mechanism to achieve viral resistance in plants transformed with the DNA constructs of the present invention.

Another aspect of the present invention relates to a method of controlling the ripening of fruit and conferring viral resistance to plants. This involves transforming a plant with a single DNA construct of the present invention which contains nucleotide sequences for proteins or polypeptides which controls papaya ripening, as well as nucleotide sequences from the coat protein of PRSV, and regenerating the transformed plant cell under conditions appropriate to control ripening and impart viral resistance. Preparation of the DNA construct can be carried out as described above. Depending on whether enhanced/early ripening, or delayed ripening is desired, different configurations of the nucleic acids of the present invention are suitable in the construct. For example, choices as to sense or antisense orientation, translatable and non-translatable nucleotides, as well as promoters, will vary depending on the effect on the transformed plant that is desired. While both the ripening-related nucleotides and the viral coat protein nucleotides can be placed under the control of a single promoter, different promoters may also be used 5' to each gene cassette if it is desirable to effect viral resistance and control of ripening at different times, in different tissues in the plant, and/or in differing intensities of expression.

EXAMPLES

Example 1

Preparation of β-Galactosidase Genes from Papaya Fruit

Three cDNA clones for three isoforms of the papaya cell-wall softening enzyme β-galactosidase (β-Gal.41, β-Gal.45, and β-Gal.64) were isolated by RT-PCR. Degenerate oligonucleotides were designed based on alignment of regions of high homology of amino acid sequences between known β-galactosidase from other plants, and were used to amplify partial-length cDNA from reverse-transcribed total RNA of mature ripe (>70% yellow) papaya fruit mesocarp. The amplified fragments were then used as specific sequences for the RACE 5'/3' technique to obtain full-length cDNAs. Amplification of the 5' and 3' ends was done using a RACE 5'/3' kit (Boehringer, Roche Molecular Biochemicals, Germany) following the manufacturer's protocol. The degenerate oligonucleotides used for initial amplification were as follows:

```
SEQ ID
NO: 31:
PR3     5' AGACITATCGTITTCTTGGAATG 3'

SEQ ID
NO: 32:
PR5     5' GAAGTGGAATCTTATCGGIGGITTCC 3'

SEQ ID
NO: 33:
PR11    5' CACAGTAAGAAACCATTGCAAG 3'

SEQ ID
NO: 34:
PR7C    5' CCAGAAAGTTIGTICCICCAGTG 3'
```

Specific primers used to obtain full-length cDNA by RACE 5'/3' were as follows:

```
For β-Gal.41:
SEQ ID NO:
35:
Mart541       5' TGGCTCCCTCCTTAGTCCATACTC 3'

SEQ ID NO:
36:
3CP3Bgal41    5' GCTTACTCCGTTGCAAGGTTCATT 3'

For β-Gal.45:
SEQ ID NO:    3CP3GAL45 5' AAGGGAGGGTCGTTCATTAAC-
37:           TAT
              3'
```

Example 2

Fruit Ripening Gene Cassettes Without Virus Gene

After cloning, the full-length β-Gal.41 (SEQ ID NO: 5) and β-Gal.45 (SEQ ID NO: 1) were used to construct the multiple fruit ripening gene cassettes. The pEPJ vector, shown in FIG. 1A, was designed specifically as a plant expression cassette As seen in FIG. 1, pEPJ consists of two 35S enhancer regions, a 35S CaMV promoter, followed by an α1 mosaic virus ("A1MV") leader sequence, and a multiple restriction enzyme site which is immediately 5' to a 35S termination region. The HindIII and KpnI restriction sites allow ligation into several other vectors, such as pUC18 and the transformation vector pGA482G, shown in FIG. 1B. As seen in FIG. 1B, pGA482G has a HindIII-KpnI cloning site and contains the commonly used plant transformation marker nptII. The pEPJ cassette was digested with HindIII-KpnI and ligated into the transformation vector pGA482G. ApaI-BamHI digested fragments of translatable (TL) and non-translatable (NTL) β-Gal.41 and β-Gal.45, and SmaI-ApaI digested fragments of each cDNA containing antisense fragments of TL ("ATL") β-Gal.41 and β-Gal.45 were ligated into the pEPJ vector. Restriction enzymes XhoI-KpnI (KpnI partial) digested fragments from the expression vector were then ligated into transformation vector pGA482G, resulting in Constructs 1–6 which contained individual ripening gene sequences. Primers used for preparation of Constructs 1–6 are given below. Italics indicate restriction site sequence added in the amplification step for cloning purposes.

<u>Construct1("C1")</u>: pTi-TL-Bgal41: Amplification of TL-Bgal41 (2.166 kb):
Gal41TL5 primer, SEQ ID NO: 38:
*GGGCCC*TCATGTTGAAGACAAACCTGGTCTTGTTC Gal41TLNTL3 primer, SEQ ID NO: 39:
*GGATCCCCCGGG*ATTAGGGTTAAACTATAAACCTTTACC <u>Construct2("C2")</u>: pTi-TL-Bgal45: Amplification of TL-Bgal45 (1.998 kb)
5 TL45 primer, SEQ ID NO: 40:
*GGGGGCCC*AAGGACCTTTCAAG GCATACATGCAAAGA 3 TLNT45 primer, SEQ ID NO: 41:
*CGGGATCCCCCGGG*CACTGGGGCAGGGATCTCCAC <u>Construct3("C3")</u>: pTi-NTL-Bgal41: Amplification ofNTL-Bgal41 (2.166 kb)
Gal41NTL5 primer, SEQ ID NO: 42:
*GGGCCC*TCATGTTGTAGACAAACCTGGTCTTGTTC Gal41TLNTL3 primer, SEQ ID NO: 43:
*GGATCCCCCGGG*ATTAGGGTTAAACTATAAACCTTTACC <u>Construct4("C4")</u>: pTi-NTL-Bgal45: Amplification of NTL-Bgal45 (1.998 kb)
3 TLNT45 primer, SEQ ID NO: 44:
*CGGGATCCCCCGGG*CACTGGGGCAGGGATCTCCAC 5NTL primer, SEQ ID NO: 45:
*GGGGGCCC*AAGGACCTTTC AAGGCATACATGCAATAGA Construct 5 ("C5"): pTi-ATL-Bgal41: Amplification of ATL-Bgal41 (2.166 kb)
Gal41TL5 primer, SEQ ID NO: 46:
*GGGCCC*TCATGTTGAAGACAAACCTGGTCTTGTTC Gal41TLNTL3 primer, SEQ ID NO:47:
*GGATCCCCCGGG*ATTAGGGTTAAACTATAAACCTTTACC Construct 6 ("C6"): pTi-ATL-Bgal45: Amplification of ATL-Bgal45 (1.998 kb)
5 TL45 primer, SEQ ID NO: 48:
*GGGGGCCC*AAGGACCTTTCAAG GCATACATGCAAAGA 3 TLNT45 primer, SEQ ID NO: 49:
*CGGGATCCCCCGGG*CACTGGGGCAGGGATCTCCAC

Example 3

Amplification and Cloning of Viral Coat Protein Gene

Total RNA was extracted from papaya infected with the KE strain of PRSV. Reverse transcription and standard PCR were used to amply the coat protein region of KE using the following two primers, for 5' and 3' amplification, respectively. Italics indicate restriction site sequence added in the amplification step for cloning purposes.

5'KECP Apa/Nco, SEQ ID NO: 50:
GATT*GGGCCCATGG*TTTGATAGTCCAAAGTGAAGCTGTGGATGCTGG

3'KECPXba/Bam, SEQ.ID. No. 51:
GAAC*GGATCCTCTAGA*TTAGTTGCGCATGCCCAGGAGAGAGTGCATG

The PCR fragment digested with NcoI/XbaI was ligated into pEPJ and/or pGA482G with the same restriction enzyme sites, or digested with ApaI/BamHI and ligated into the pEPJ vector.

Example 4

Construction of Fruit Ripening Gene Cassettes With Virus Gene

The pEPJ86 cassette digested with HindIII-KpnI was ligated into transformation vector pGA482G. ApaI-BamHI digested fragments of non-translatable (NTL) were ligated into pEPJ-Kenco/xba vector and XhoI-KpnI (KpnI partial) digested fragments from the expression vector were then ligated into transformation vector pGA482G-KEnco/xba. XhoI-SmaI digested fragments of non-translatable (NTL) were ligated into pEPJ-KEapa/bam and XhoI-KpnI (KpnI partial) digested fragments from the expression vector were then ligated into transformation vector pGA482G, resulting in Constructs 7–10, as shown in FIGS. 2A–D. Primers used for preparation of Constructs 7–10 are given below. Italics indicate restriction site sequences added in amplification step for cloning purposes.

Construct7("C7"): pTi-KE-NTL-Bgal41: Amplification of NTL-Bgal41 (2.216 kb)
Gal41NTL5' primer, SEQ ID NO: 52:
*GGGCCC*TCATGTTGTAGACAAACCTGGTCTTGTTC Gal41TLNTL3' primer, SEQ ID NO: 53:
*GGATCCCCCGGG*ATTAGGGTTAAACTATAAACCTTTACC Construct8("C8"): pTi-KE-NTL-Bgal45: Amplification of NTL-Bgal45 (2.120 kb)
3'TLNT45 primer, SEQ ID NO: 54:
*CGGGATCCCCCGGG*CACTGGGGCAGGGATCTCCAC 5'NTL45 primer, SEQ ID NO: 55
*GGGGGCCC*AAGGACCTTTC AAGGCATACATGCAATAGA Construct9("C9"): pTi-NTL-Bgal41-KE: Amplification of NTL-Bgal41 (2.216 kb)
Gal41NTL5' primer, SEQ ID NO: 56:
*GGGCCC*TCATGTTGTAGACAAACCTGGTCTTGTTC Gal41TLNTL3' primer, SEQ ID NO: 57:
*GGATCCCCCGGG*ATTAGGGTTAAACTATAAACCTTTACC Construct10("C10"): pTi-NTL-Bgal45-KE
3'TLNT45 primer, SEQ ID NO: 58:
*CGGGATCCCCCGGG*CACTGGGGCAGGGATCTCCAC 5'NTL45 primer, SEQ ID NO: 59:
*GGGGGCCC*AAGGACCTTTCAAGGCATACATGCAATAGA

Example 5

Figure 3:
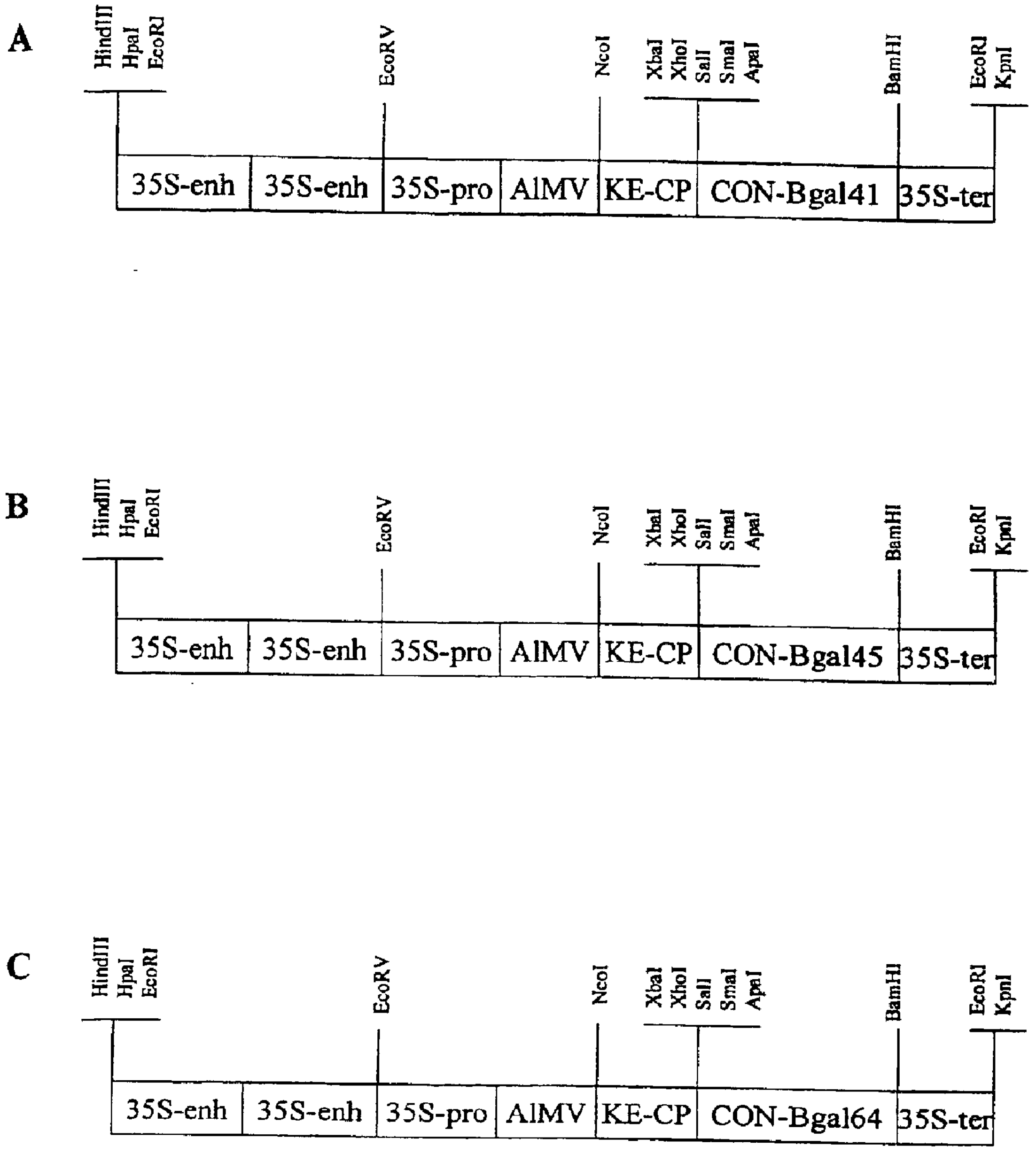
FIGS. 3A–C show the configuration of Constructs 11–13, each containing both a PRSV-CP nucleotide sequence derived from the KE strain of PRSV and a papaya fruit ripening isozyme nucleotide sequence.

Construction of Fruit Conserved Ripening Gene Cassettes With Virus Coat Protein Gene The pEPJ86 cassette digested with HindIII-KpnI was ligated into transformation vector pGA482G. ApaI-BamHI digested fragments of each conserved region of β-galactosidase isoenzymes β-Gal.41, β-Gal.45 and β-Gal.64 were ligated individually into pEPJ-KEnco/xba vector. XhoI-KpnI digested fragments from the expression vector were then ligated into transformation vector pGA482G-KEnco/xba, resulting in Constructs 11–13, as shown in FIGS. 3A–C, containing KE-CP and β-Gal.41, β-Gal.45 and β-Gal.64 conserved region DNA, respectively. Primers used for amplification are given below. Italics indicate restriction site sequences added in amplification step for cloning purposes.

Construct11("C11"): pTi-KE-CON-Bgal41
5gal41apa primer, SEQ ID NO: 60:
*GGGGGCCC*AGACGTACGTGTTTTGGAATGGGCAT 3gal41bamh primer, SEQ ID NO: 61:
*CGGGATCC*CCGAAATTGGTGCCGCCGTG Construct12("C12"): pTi-KE-CON-Bgal45
5gal45apa primer, SEQ ID NO: 62:
*GGGGGCCC*AGACGTACGTGTTTTGGAATGGGCAT 3gal45bamh primer, SEQ ID NO: 63:
*CGGGATCC*CCGAAATTGGTGCCGCCATG Construct13("C13"): pTi-KE-CON-βgal64
5gal64apa primer, SEQ ID NO: 64:
*GGGGGCCC*GAATGGAATTATGGGGGGGTTCC 3gal64bamh primer, SEQ ID NO: 65:
*CGGGATCC*CCAAAGTTGGTGCCGCCATG

Example 6

Figure 4:
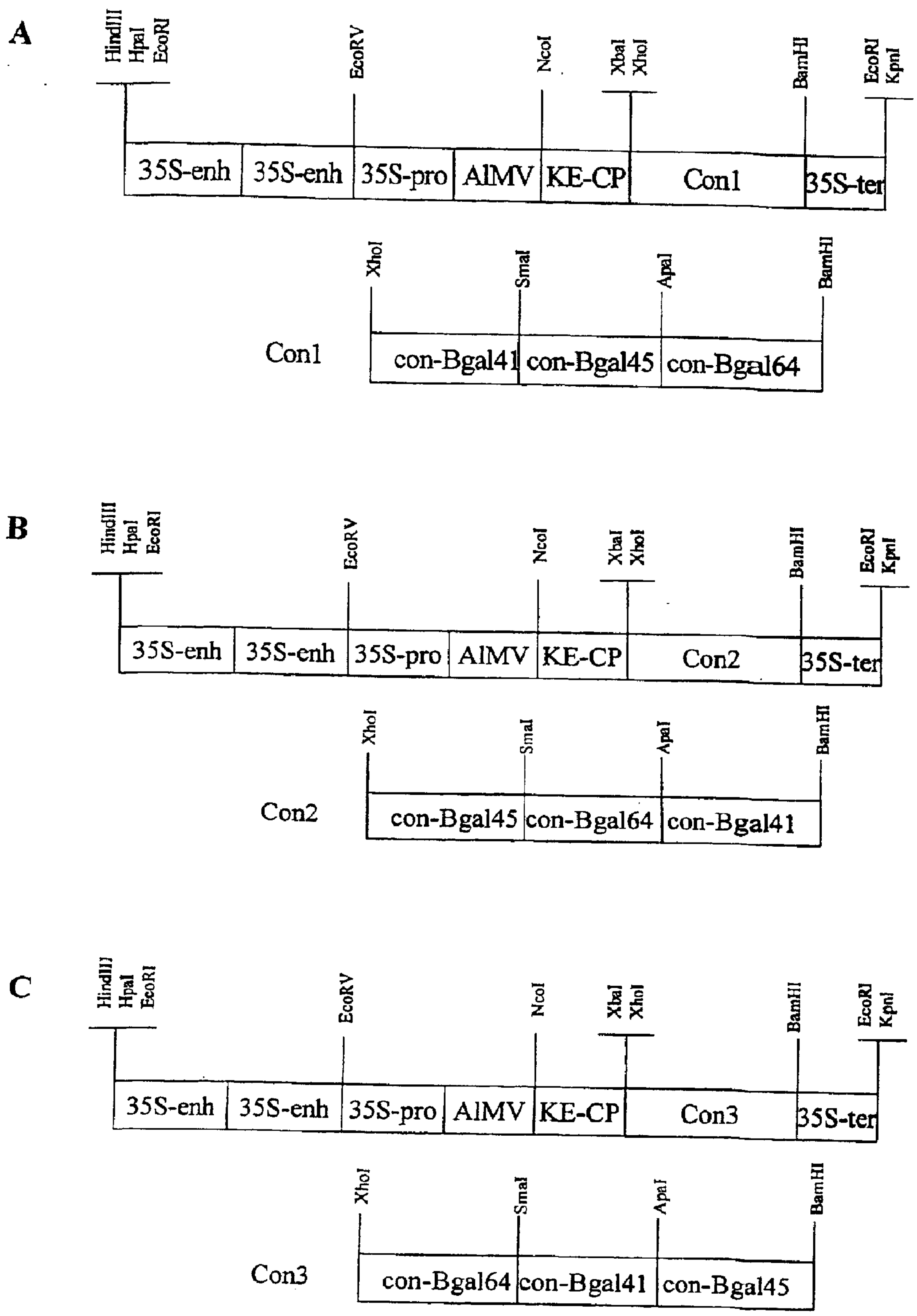
FIGS. 4A–C show the configuration of Constructs 14–16, each containing a PRSV-CP nucleotide sequence derived from the KE strain of PRSV inserted upstream of a DNA cassette containing multiple papaya fruit ripening isozyme nucleotide sequences.
Figure 5:
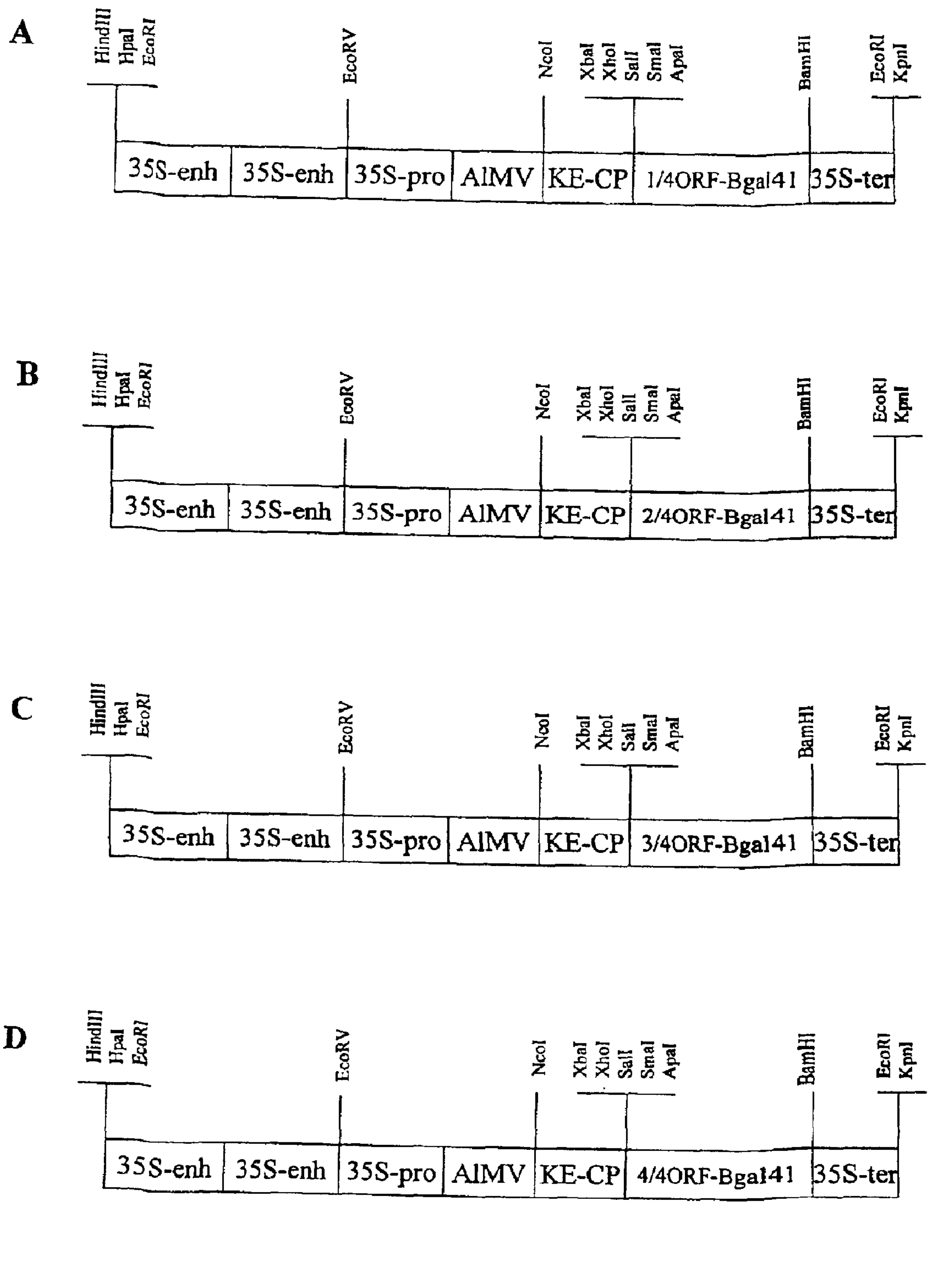
FIGS. 5A–D show the configuration of Constructs 17–20, each containing a PRSV-CP nucleotide sequence derived from the KE strain of PRSV inserted upstream of a nucleotide sequence derived from the ORF of the β-Gal.41 papaya fruit ripening isozyme.

Construction of Multiple Gene Cassettes Containing Conserved Fruit Ripening Genes and Virus Coat Protein Gene The pEPJ86 cassette digested with HindIII-KpnI was ligated into transformation vector pGA482G. XhoI-SmaI, SmaI-ApaI and ApaI-BamHI digested fragments of each conserved region of β-Gal.41, β-Gal.45, and β-Gal.64 were ligated together downstream of KE-CP into pEPJ-Kenco/xba vector. XhoI-KpnI digested fragments from the expression vector were then ligated into transformation vector pGA482G-KEnco/xba, resulting in Constructs 14–16, containing KE-CP and all conserved DNA sequences from all three β-Gal genes, as shown in FIGS. 4A–C. Primers used for amplification are given below.

Construct14("C14"): pTi-KE-CON-Bgal41-45-64
5gal4145xho primer SEQ ID NO: 66:
*CCGCTCGAG*AGACGTATGTGTTTTGGAATGGACAT 3galsma primer, SEQ ID NO: 67:
*TCCCCCGGG*CCAAAATTGGTGCCGCCGTG 3gal45sma primer, SEQ ID NO: 68:
*TCCCCCGGG*AGACGTACGTGTTTTGGAATGGGCAT 3gal45apa primer, SEQ ID NO: 69:
*GGGGGCCC*CCGAAATTGGTGCCGCCATG 5gal64apa primer, SEQ ID NO: 70:
*GGGGGCCC*GAATGGAATTATGGGGGGGTTCC 3gal64bamh primer, SEQ ID NO: 71
*CGGGATCC*CCAAAGTTGGTGCCGCCATG Construct15("C15"): pTi-KE-CON-Bgal45-64-41
5gal45xho primer, SEQ ID NO: 72:
*CCGCTCGAG*AGACGTATGTGTTTTGGAATGGACAT 3gal45sma primer, SEQ ID NO: 73:
*TCCCCCGGG*CCGAAATTGGTGCCGCCATG 5gal64sma, SEQ ID NO: 74:
*TCCCCCGGG*GAATGGAATTATGGGGGGGTTCC 3gal45apa primer, SEQ ID NO: 75:
*GGGGGCCC*CCAAAGTTGGTGCCGCCATG 5gal45apa primer, SEQ ID NO: 76:
*GGGGGCCC*AGACGTACGTGTTTTGGAATGGGCAT -continued 3gal45bamh primer, SEQ ID NO: 77:
*CGGGATCC*CCGAAATTGGTGCCGCCATG Construct16("C16"): pTi-KE-CON-Bgal64-41-45
5gal64xho primer, SEQ ID NO: 78:
*CCGCTCGAG*GAATGGAATTATGGGGGGTTCCG 3gal64sma primer, SEQ ID NO: 79:
*TCCCCCGGG*CCAAAGTTGGTGCCGCCATG

Example 7

Construction of Gene Cassettes Containing Fragments of Fruit Ripening β-GAl.41 Gene With Virus Coat Protein Gene Constructs were prepared which contained a KE-CP nucleotide and varying lengths of the open reading frame (ORF) of the β-Gal.41 gene. The pEPJ86 cassette digested with HindIII-KpnI was ligated into transformation vector pGA482G. ApaI-BamHI digested fragments amplified from the ORF of β-Gal.41 were ligated into pEPJ-KEnco/xba vector. XhoI-KpnI digested fragments from the expression vector were then ligated into transformation vector pGA482G-KEnco/xba resulting in Constructs 17–20, as shown in FIGS. 5A–D. Primers used for amplification as given below. Italics indicate restriction site sequences added in amplification step for cloning purposes.

Construct 17 ("C17"): pTi-KE-14TL-Bgal41
145TL41apa primer, SEQ ID NO: 80:
*GGGGGCCC*ATGTTGAAGACAAACCTGGTCTTGTTC 143TL41bamh prime, SEQ ID NO: 81:
*CGGGATCC*CATTTGTGCCTTGAAAGGTCCATT Construct 18 ("C18"): pTi-KE-24TL-Bgal41
245TL41apa primer, SEQ ID NO: 82:
*GGGGGCCC*TGAACCTCAAGGGGGTCCAAT 243TL41bamh primer, SEQ ID NO: 83:
*CGGGATCC*TGCCCCCATTTTGGCTCC Construct 19 ("C19"): pTi-KIE-34TL-Bgal41
345TL41apa primer, SEQ ID NO: 84:
*GGGGGCCC*TTGAGGGATTTGCATAAAACCATCA 343TL41bamh primer, SEQ ID NO: 85:
*CGGGATCC*CTGATAGTTGACCATTCACAAAAACATG Construct 20 ("C20"): pTi-KE-44TL-Bgal41
445TL41apa primer, SEQ ID NO: 86:
*GGGGGCCC*CTGTATATGGACAATTGGAAAATCCCA 443TL41bamh primer, SEQ ID NO: 87:
*CGGGATCC*TACCATCTCTGAGAAGCCTTTCCAC Although the invention has been described in detail for the purpose of illustration, it is understood that such detail is solely for that purpose, and variations can be made therein by those skilled in the art without departing from the spirit and scope of the invention which is defined by the following claims.

---

What is claimed:

1. A DNA construct comprising:

a first DNA molecule encoding a protein or polypeptide which controls papaya fruit ripening, wherein the protein or polypeptide has the amino acid sequence selected from the group consisting of SEQ ID NO: 2, SEQ ID NO: 4, SEQ ID NO: 6, SEQ ID NO: 8, and SEQ ID NO: 10, and a second DNA molecule encoding a papaya ringspot virus coat protein, wherein the first and second DNA molecules may be inserted in the DNA construct in a sense (5'→3') or an antisense (3'→5') orientation.

2. A DNA construct according to claim 1 further comprising:

a heterologous DNA promoter and a 3' regulatory region, wherein the promoter and the 3' regulatory region are operably linked to the first and the second DNA molecules.

3. The DNA construct according to claim 1, wherein one or more of the DNA molecules are in the sense (5'→3') orientation.

4. The DNA construct according to claim 1, wherein one or more of the DNA molecules are inserted in the antisense (3'→5') orientation.

5. The DNA construct according to claim 1, wherein the DNA molecules encode a nontranslatable RNA.

6. A DNA construct according to claim 1, wherein the DNA molecule which encodes a protein or polypeptide which controls papaya fruit ripening is selected from a group consisting of a β-galactosidase, a pectinmethylesterase, and a polygalacturonase.

7. A DNA construct according to claim 1, wherein the papaya ringspot virus coat protein DNA molecule is derived from a gene encoding a papaya ringspot virus coat protein in a papaya ringspot virus strain selected from the group consisting of TB, KA, ME, YK, BR, JA, OA, and VE.

8. An expression vector comprising:

the DNA construct according to claim 1.

9. A host cell transduced with the DNA construct according to claim 1, wherein the cell is selected from the group consisting of a bacterial cell and a plant cell.

10. A host cell according to claim 9, wherein the cell is a plant cell.

11. A plant cell according to claim 10, wherein the plant is papaya.

12. A transgenic plant transformed with the DNA construct according to claim 1.

13. A transgenic plant according to claim 12, wherein the plant is papaya.

14. A method for controlling the ripening of papaya fruit and conferring papaya ringspot virus disease resistance to a papaya plant comprising:

transforming a papaya plant cell with the DNA construct according to claim 1 and regenerating a papaya plant from the transformed cell under conditions effective to control ripening and confer papaya ringspot virus disease resistance to the papaya plant.

15. A method according to claim 14, wherein the DNA construct promotes ripening of papaya fruit.

16. A method according to claim 14, wherein the DNA construct delays ripening of papaya fruit.

17. A method according to claim 14, wherein resistance is conferred to a papaya ringspot virus strain selected from the group consisting of TH, KA, ME, YK, BR, JA, OA, and VE.

18. The DNA construct according to claim 1, wherein the first DNA molecule encodes a protein or polypeptide having the amino acid sequence of SEQ ID NO: 2.

19. The DNA construct according to claim 1, wherein the first DNA molecule encodes a protein or polypeptide having the amino acid sequence of SEQ ID NO: 4.

20. The DNA construct according to claim 1, wherein the first DNA molecule encodes a protein or polypeptide having the amino acid sequence of SEQ ID NO: 6.

21. The DNA construct according to claim 1, wherein the first DNA molecule encodes a protein or polypeptide having the amino acid sequence of SEQ ID NO: 8.

22. The DNA construct according to claim 1, wherein the first DNA molecule encodes a protein or polypeptide having the amino acid sequence of SEQ ID NO: 10.

* * * * *

SEQUENCE LISTING

<160> NUMBER OF SEQ ID NOS: 90

<210> SEQ ID NO 1
<211> LENGTH: 2827
<212> TYPE: DNA
<213> ORGANISM: Carica papaya
<220> FEATURE:
<221> NAME/KEY: unsure
<222> LOCATION: (659)
<223> OTHER INFORMATION: N at position 659 in this sequence is either a, c, g or t

<400> SEQUENCE: 1

```
agacgtacgt gttttggaat gggcatgagc cttcacctgg caaatactac tttggaggaa     60

actatgatct ggttagattc attaagctgg tgaagcaagc aggcctctat gttcatctca    120

ggattggtcc atatgtttgt gccgagtgga actttggggg ttttcctgcc cggcttaagt    180

acattccagg catcgctttc agaacgaaca atggaccttt caaggcatac atgcaaagat    240

ttacaaagaa aattgttgat atgatgaaag ctgaagggtt gtttgaatct cagggtggtc    300

caataatttt atcccagatt gaaaatgaat atggacccat ggagtacgaa cttggtgcag    360

ccgggcgtgc ttacgctcaa tgggcagctc agatggctgt gggattcggt actggtgtcc    420

cgtgggtcat gtgcaagcaa gatgatgcac ctgatcctat tattaacact tgcaatggtt    480

tctactgtga ttacttttct ccaaacaaag catacaagcc caagatgtgg actgaagctt    540

ggactggttg gtttactgga tttggaggtg cagttcctta ccgaccagtg gaagacttgg    600

cattttcagt tgcaaggttt atacagaatg gagggtcgtt cattaactat tatatgtgnc    660

atggaggaac aaattttggc cgcactgctg gtggcccctt cattgccact agctatgatt    720
```

-continued

```
atgatgctcc tcttgatgaa tatggactgg tgaggcaacc taaatggggt catttgaaag    780
atttacatcg agcaataaaa ctgtgtgaac cagcactggt gtctggtgat ccttctgtca    840
tgccacttgg acgctttcaa gaggctcatg tcttcaaatc aaaatatggg cattgtgctg    900
cattccttgc aaattacaat ccaagatctt ttgctaaagt tgcctttggg aatatgcatt    960
acaacctgcc tccttggtct atcagcattc ttcccgactg taaaaacact gtttataaca   1020
ctgcaagggt tggtgctcaa agtgctagga tgaagatggt tcctgttcct attcatggag   1080
cattctcttg gcaggcttat aatgaagagg caccttcctc aaatggtgaa aggtcattca   1140
cgacggtagg attggtggaa cagataaata caactagaga tgtctctgac tatttatggt   1200
actcaacgga tgttaagatt gatcctgatg aaggattctt gaagactgga aagtacccca   1260
cactcactgt tttatctgct ggtcatgctt tacatgtatt tgtcaacgac caactatcag   1320
gaactgccta tggaagctta gaatttccaa agataacttt cagtaaaggt gtaaatctga   1380
gagctggcat caacaagatt tcaattctaa gcattgctgt tggtcttccg aacgtcggtc   1440
ctcattttga gacatggaat gctggagttc ttggtcctgt aacattgaat ggtcttaacg   1500
agggaagaag ggacttatca tggcagaaat ggtcttacaa ggttggtgtt gaaggagaag   1560
caatgagtct tcattcactc agtgggagtt cctcagttga gtggactgca gggtcttttg   1620
tagcaagaag gcagcccctt acttggttca aaactacttt caatgctccg gctggaaatt   1680
ctccattggc tctggatatg aatagtatgg gtaaaggaca aatatggata aatggaaaga   1740
gtatcgggcg gcactggcct gcatataaag catctggttc ttgtggttgg tgtgattatg   1800
ctggaacatt taatgagaag aagtgcttaa gtaattgtgg agaggcttct caaagatggt   1860
atcacgttcc tcgctcatgg ctcaacccaa cagggaattt gttggttgtt tttgaagaat   1920
ggggtggaga tcctaatgga atatccttgg ttagaagaga agtagacagt gtttgtgctg   1980
atatttatga gtggcaacca actctgatga attatcaaat gcaagcatct ggaaaggtaa   2040
acaaaccact gcggcctaat aaagctcatt tacagtgtgg ccctgggcag aagttctcat   2100
cagtcaagtt tgccagtttt ggcactccag aaggggcttg tggaagctac cggagggaag   2160
ctgccatgca catcattctt atgatgcttt tgagaggctc tgtgttgggc agaactggtg   2220
ctcagtaaca gtagcacccg aaatgttcgg tggagatccc tgccccagtg tcatgaagaa   2280
actcgcggtg gaggttgttt gcagctgaag aactgtaaca tcagaaaagt gatggaagtg   2340
aaggaaattg tggactgatt ctttttttta caagtcatca gttatattat ttcttggata   2400
aattaagtct acacatcgaa gtttgcagcc attctgttcc agctttcaaa tggtgaagtt   2460
gtacaaatat acagcacaca ccatggatgg ctggcatctc ttacaagcat tgtcaaagtg   2520
tttgtccatt ggaaaaatgt acataaagca atgattcgtt gcctgcatgt tatatggaag   2580
tttaaggatg gaatctgtcg aagcacagtg agacggcggt aacccagtcc atgtgccaga   2640
tattttagct tttatagggt atggaaatcc tctgatttct agtcatttta agtggtacat   2700
tctctttcaa gtttcttgag aagcaaaatt gtttacactg ctttgttctt gcaagaaaaa   2760
aggaacaaag gcctcaaatg gccataatat atttactctt tttagttcaa agaaaaaaaa   2820
aaaaaaa                                                             2827
```

<210> SEQ ID NO 2
<211> LENGTH: 665
<212> TYPE: PRT
<213> ORGANISM: Carica papaya
<220> FEATURE:
<221> NAME/KEY: UNSURE -continued

```
<222> LOCATION: (143)
<223> OTHER INFORMATION: Xaa at position 143 in this sequence is any
      amino acid

<400> SEQUENCE: 2

Met Gln Arg Phe Thr Lys Lys Ile Val Asp Met Met Lys Ala Glu Gly
  1               5                  10                  15

Leu Phe Glu Ser Gln Gly Gly Pro Ile Ile Leu Ser Gln Ile Glu Asn
             20                  25                  30

Glu Tyr Gly Pro Met Glu Tyr Glu Leu Gly Ala Ala Gly Arg Ala Tyr
         35                  40                  45

Ala Gln Trp Ala Ala Gln Met Ala Val Gly Phe Gly Thr Gly Val Pro
     50                  55                  60

Trp Val Met Cys Lys Gln Asp Asp Ala Pro Asp Pro Ile Ile Asn Thr
 65                  70                  75                  80

Cys Asn Gly Phe Tyr Cys Asp Tyr Phe Ser Pro Asn Lys Ala Tyr Lys
                 85                  90                  95

Pro Lys Met Trp Thr Glu Ala Trp Thr Gly Trp Phe Thr Gly Phe Gly
            100                 105                 110

Gly Ala Val Pro Tyr Arg Pro Val Glu Asp Leu Ala Phe Ser Val Ala
        115                 120                 125

Arg Phe Ile Gln Asn Gly Gly Ser Phe Ile Asn Tyr Tyr Met Xaa His
    130                 135                 140

Gly Gly Thr Asn Phe Gly Arg Thr Ala Gly Gly Pro Phe Ile Ala Thr
145                 150                 155                 160

Ser Tyr Asp Tyr Asp Ala Pro Leu Asp Glu Tyr Gly Leu Val Arg Gln
                165                 170                 175

Pro Lys Trp Gly His Leu Lys Asp Leu His Arg Ala Ile Lys Leu Cys
            180                 185                 190

Glu Pro Ala Leu Val Ser Gly Asp Pro Ser Val Met Pro Leu Gly Arg
        195                 200                 205

Phe Gln Glu Ala His Val Phe Lys Ser Lys Tyr Gly His Cys Ala Ala
    210                 215                 220

Phe Leu Ala Asn Tyr Asn Pro Arg Ser Phe Ala Lys Val Ala Phe Gly
225                 230                 235                 240

Asn Met His Tyr Asn Leu Pro Pro Trp Ser Ile Ser Ile Leu Pro Asp
                245                 250                 255

Cys Lys Asn Thr Val Tyr Asn Thr Ala Arg Val Gly Ala Gln Ser Ala
            260                 265                 270

Arg Met Lys Met Val Pro Val Pro Ile His Gly Ala Phe Ser Trp Gln
        275                 280                 285

Ala Tyr Asn Glu Glu Ala Pro Ser Ser Asn Gly Glu Arg Ser Phe Thr
    290                 295                 300

Thr Val Gly Leu Val Glu Gln Ile Asn Thr Thr Arg Asp Val Ser Asp
305                 310                 315                 320

Tyr Leu Trp Tyr Ser Thr Asp Val Lys Ile Asp Pro Asp Glu Gly Phe
                325                 330                 335

Leu Lys Thr Gly Lys Tyr Pro Thr Leu Thr Val Leu Ser Ala Gly His
            340                 345                 350

Ala Leu His Val Phe Val Asn Asp Gln Leu Ser Gly Thr Ala Tyr Gly
        355                 360                 365

Ser Leu Glu Phe Pro Lys Ile Thr Phe Ser Lys Gly Val Asn Leu Arg
    370                 375                 380

Ala Gly Ile Asn Lys Ile Ser Ile Leu Ser Ile Ala Val Gly Leu Pro
```

-continued

```
385                 390                 395                 400

Asn Val Gly Pro His Phe Glu Thr Trp Asn Ala Gly Val Leu Gly Pro
                405                 410                 415

Val Thr Leu Asn Gly Leu Asn Glu Gly Arg Arg Asp Leu Ser Trp Gln
            420                 425                 430

Lys Trp Ser Tyr Lys Val Gly Val Glu Gly Glu Ala Met Ser Leu His
        435                 440                 445

Ser Leu Ser Gly Ser Ser Ser Val Glu Trp Thr Ala Gly Ser Phe Val
    450                 455                 460

Ala Arg Arg Gln Pro Leu Thr Trp Phe Lys Thr Thr Phe Asn Ala Pro
465                 470                 475                 480

Ala Gly Asn Ser Pro Leu Ala Leu Asp Met Asn Ser Met Gly Lys Gly
                485                 490                 495

Gln Ile Trp Ile Asn Gly Lys Ser Ile Gly Arg His Trp Pro Ala Tyr
            500                 505                 510

Lys Ala Ser Gly Ser Cys Gly Trp Cys Asp Tyr Ala Gly Thr Phe Asn
        515                 520                 525

Glu Lys Lys Cys Leu Ser Asn Cys Gly Glu Ala Ser Gln Arg Trp Tyr
    530                 535                 540

His Val Pro Arg Ser Trp Leu Asn Pro Thr Gly Asn Leu Leu Val Val
545                 550                 555                 560

Phe Glu Glu Trp Gly Gly Asp Pro Asn Gly Ile Ser Leu Val Arg Arg
                565                 570                 575

Glu Val Asp Ser Val Cys Ala Asp Ile Tyr Glu Trp Gln Pro Thr Leu
            580                 585                 590

Met Asn Tyr Gln Met Gln Ala Ser Gly Lys Val Asn Lys Pro Leu Arg
        595                 600                 605

Pro Asn Lys Ala His Leu Gln Cys Gly Pro Gly Gln Lys Phe Ser Ser
    610                 615                 620

Val Lys Phe Ala Ser Phe Gly Thr Pro Glu Gly Ala Cys Gly Ser Tyr
625                 630                 635                 640

Arg Arg Glu Ala Ala Met His Ile Ile Leu Met Met Leu Leu Arg Gly
                645                 650                 655

Ser Val Leu Gly Arg Thr Gly Ala Gln
            660                 665


<210> SEQ ID NO 3
<211> LENGTH: 534
<212> TYPE: DNA
<213> ORGANISM: Carica papaya
<220> FEATURE:
<221> NAME/KEY: unsure
<222> LOCATION: (1)..(534)
<223> OTHER INFORMATION: N at any position in this sequence is either
      a, c, g or t

<400> SEQUENCE: 3

gaatggaatt atggggggtt ccggtttggc tgaagtatgt ccctggaatc agctttagaa     60

cagacaatga gcctttcaag agagctatgc aagggttcac agagaagatt gtgggactat    120

naagagtgaa aacttgtttg agtcccaggg tggccccatt atcctctctc agattgagaa    180

tgagtacggg aaacagagca agttattngg cgccgatgga tataattata tnagttgggc    240

agcaaaaatg gctgttgaaa caggaacagg tgtcccctgg gtcatgtgca aagaagacga    300

tgcaccagat ccggtnatan acacgtgcaa atggttttac tgtgaagcat tctctcctaa    360

caaaccttac aagcccaaga tctggacgga ggcatggagt ggctggttca cagactttgg    420
```

-continued tggccccatc caccagcggc cagttcagga tcttgcattt gcagttgcta agttcataca 480
aaaaggaggg tcctttgtca actattacat gtatcatggc ggcaccaact ttgg 534

<210> SEQ ID NO 4
<211> LENGTH: 177
<212> TYPE: PRT
<213> ORGANISM: Carica papaya
<220> FEATURE:
<221> NAME/KEY: UNSURE
<222> LOCATION: (1)..(177)
<223> OTHER INFORMATION: Xaa at any position in this sequence is any amino acid

<400> SEQUENCE: 4

Met Glu Leu Trp Gly Val Pro Val Trp Leu Lys Tyr Val Pro Gly Ile
1 5 10 15

Ser Phe Arg Thr Asp Asn Glu Pro Phe Lys Arg Ala Met Gln Gly Phe
20 25 30

Thr Glu Lys Ile Val Gly Leu Xaa Arg Val Lys Thr Cys Leu Ser Pro
35 40 45

Arg Val Ala Pro Leu Ser Ser Leu Arg Leu Arg Met Ser Thr Gly Asn
50 55 60

Arg Ala Ser Tyr Xaa Ala Pro Met Asp Ile Ile Ile Xaa Val Gly Gln
65 70 75 80

Gln Lys Trp Leu Leu Lys Gln Glu Gln Val Ser Pro Gly Ser Cys Ala
85 90 95

Lys Lys Thr Met His Gln Ile Arg Xaa Xaa Thr Arg Ala Asn Gly Phe
100 105 110

Thr Val Lys His Ser Leu Leu Thr Asn Leu Thr Ser Pro Arg Ser Gly
115 120 125

Arg Arg His Gly Val Ala Gly Ser Gln Thr Leu Val Ala Pro Ser Thr
130 135 140

Ser Gly Gln Phe Arg Ile Leu His Leu Gln Leu Leu Ser Ser Tyr Lys
145 150 155 160

Lys Glu Gly Pro Leu Ser Thr Ile Thr Cys Ile Met Ala Ala Pro Thr
165 170 175

Leu

<210> SEQ ID NO 5
<211> LENGTH: 2746
<212> TYPE: DNA
<213> ORGANISM: Carica papaya

<400> SEQUENCE: 5
ggcacgagaa acacactcaa ctcctccatt aatgtcctct ttaacaaaaa tctaaatttc 60
cttccttctc ttctactaaa cagcattgaa ggagtaaaca attatttgat attttcattt 120
gctatcatgt tgaagacaaa cctggtcttg ttcttgttgt tttgttcatg gctttggtct 180
gttgaagcta ctgtgtctta cgaccataaa gctataatca ttaatggccg cagaaggatt 240
cttatttctg gctccattca ttatcccaga agcactcctc agatgtggcc tgatcttata 300
caaaatgcta aagaaggagg gttagatgtc atacagactt atgtttttg gaacggacat 360 gagccctctc ctggaaatta ttattttgaa gacaggtatg atcttgtaaa gttcatcaag 420
ttggtgcatc aagctggtct gtatgttcat ctcagaataa gtccttatat ttgtggtgaa 480
tggaattttg gggttttcc tgtttggctc aaatacgttc ctggtattca attcagaaca 540

-continued

```
gacaatggac ctttcaaggc acaaatgcaa aaatttacag agaaaatagt caacatgatg    600

aaggcagaaa agttatttga acctcaaggg ggtccaataa ttatgtcaca gatagagaat    660

gagtatggac ctattgagtg ggaaattgga gcaccgggga aagcttatac aaaatgggca    720

gcacaaatgg cagtgggtct tggcactgga gtcccatgga ttatgtgcaa gcaagaggat    780

gctcctgacc caattattga cacttgcaat ggtttctatt gtgaaaattt catgccaaac    840

gccaactaca aaccaaaaat gtttacagag gcctggactg gctggtacac ggaatttggc    900

ggtccagttc cttatagacc tgcagaagac atggcttact ccgttgcaag gttcattcag    960

aataggggat cattcattaa ttattatatg taccatggag gaacaaattt tggcagaact   1020

gctggaggtc ctttcattgc tactagctat gattacgatg cccctcttga tgagtatgga   1080

ctaaggaggg agccaaaatg gggcacttg agggatttgc ataaaaccat caaattatgt   1140

gaaccatctt tagtttctgt tgatcctaaa gtgacatcgt taggaagtaa ccaagaggct   1200

catgtgtttt ggacaaaaac ctcttgtgct gcattccttg ctaactacga tctgaagtac   1260

tcagttagag tcacctttca aaacctgcct tatgacctac ctccttggtc tgtcagcatt   1320

cttcctgact gcaaaactgt agttttcaac actgcaaagg ttgtttcaca aggctcgcta   1380

gcaaagatga ttgctgtcaa cagtgcattc tcttggcagt cgtacaacga agaaacacct   1440

tccgcaaatt atgatgctgt atttaccaaa gatgggctgt gggaacagat aagtgtcacc   1500

agagatgcta cagattactt gtggtatatg acagatgtga caataggtcc tgatgaagca   1560

ttcttgaaga atgggcaaga tcccattttg acagtcatgt cagcaggcca tgctttgcat   1620

gtttttgtga atggtcaact atcaggaact gtatatggac aattggaaaa tcccaaacta   1680

gcctttagtg gcaaggtgaa actgagagca ggagtcaaca aggtttcttt actaagtatc   1740

gctgttggcc ttccgaatgt tggcttacac tttgaaacat ggaatgctgg ggttctgggt   1800

ccagtgacat tgaaaggggt gaattcagga acatgggata tgtcaaaatg gaaatggtct   1860

tacaagattg gtctgaaagg cgaagccttg agccttcata cagttagtgg cagttcgtct   1920

gttgagtggg ttgaaggatc attactagct caaagacaac ccctcatttg gtacaagact   1980

acttttaacg caccagtagg taatgatcca ttagctttag atatgaacag tatgggaaaa   2040

ggtcagatat ggataaatgg tcaaagtatt ggacgccact ggcctggata taaagctcgt   2100

ggaagttgtg gtgcttgcaa ctatgctgga atatatgatg agaaaaaatg tcatagtaac   2160

tgtggaaagg cttctcagag atggtaccat gttcctcgct cgtggctcaa cccaactgcg   2220

aacctattag ttgtttttga agaatggggt ggtgatccaa caaagatttc tttggtgaaa   2280

agagttgtgt agttagtttt cagaaagcta aaatgggtaa aggtttatag tttaacccta   2340

ataaatgaag tccccagtta ggtcaaattt agcacagaaa atagtttgga agaatccaag   2400

tgactttttg tccttagggg tgatacaagc ttaaacgaag cagattgccc agaattgcca   2460

aagggaatgg atatggtaga atatcacaac atttttatgt gcagagacaa gctattgcta   2520

cacctccata cctcatacat taggccaact agaagagtat agttttaata tatatacaca   2580

cgcacacaca cacacacagt atatcttgat aattattaag gatatacata cctctagcta   2640

gctggggttc caatctaagt attcagggaa aataaacctc atgccttctt atttgtaaga   2700

acaaatcagg aagtattatt aataaaaaaa aaaaaaaaaa aaaaaa                 2746
```

<210> SEQ ID NO 6
<211> LENGTH: 721
<212> TYPE: PRT
<213> ORGANISM: Carica papaya -continued

<400> SEQUENCE: 6

Met Leu Lys Thr Asn Leu Val Leu Phe Leu Leu Phe Cys Ser Trp Leu
1 5 10 15

Trp Ser Val Glu Ala Thr Val Ser Tyr Asp His Lys Ala Ile Ile Ile
20 25 30

Asn Gly Arg Arg Arg Ile Leu Ile Ser Gly Ser Ile His Tyr Pro Arg
35 40 45

Ser Thr Pro Gln Met Trp Pro Asp Leu Ile Gln Asn Ala Lys Glu Gly
50 55 60

Gly Leu Asp Val Ile Gln Thr Tyr Val Phe Trp Asn Gly His Glu Pro
65 70 75 80

Ser Pro Gly Asn Tyr Tyr Phe Glu Asp Arg Tyr Asp Leu Val Lys Phe
85 90 95

Ile Lys Leu Val His Gln Ala Gly Leu Tyr Val His Leu Arg Ile Ser
100 105 110

Pro Tyr Ile Cys Gly Glu Trp Asn Phe Gly Gly Phe Pro Val Trp Leu
115 120 125

Lys Tyr Val Pro Gly Ile Gln Phe Arg Thr Asp Asn Gly Pro Phe Lys
130 135 140

Ala Gln Met Gln Lys Phe Thr Glu Lys Ile Val Asn Met Met Lys Ala
145 150 155 160

Glu Lys Leu Phe Glu Pro Gln Gly Gly Pro Ile Ile Met Ser Gln Ile
165 170 175

Glu Asn Glu Tyr Gly Pro Ile Glu Trp Glu Ile Gly Ala Pro Gly Lys
180 185 190

Ala Tyr Thr Lys Trp Ala Ala Gln Met Ala Val Gly Leu Gly Thr Gly
195 200 205

Val Pro Trp Ile Met Cys Lys Gln Glu Asp Ala Pro Asp Pro Ile Ile
210 215 220

Asp Thr Cys Asn Gly Phe Tyr Cys Glu Asn Phe Met Pro Asn Ala Asn
225 230 235 240

Tyr Lys Pro Lys Met Phe Thr Glu Ala Trp Thr Gly Trp Tyr Thr Glu
245 250 255

Phe Gly Gly Pro Val Pro Tyr Arg Pro Ala Glu Asp Met Ala Tyr Ser
260 265 270

Val Ala Arg Phe Ile Gln Asn Arg Gly Ser Phe Ile Asn Tyr Tyr Met
275 280 285

Tyr His Gly Gly Thr Asn Phe Gly Arg Thr Ala Gly Gly Pro Phe Ile
290 295 300

Ala Thr Ser Tyr Asp Tyr Asp Ala Pro Leu Asp Glu Tyr Gly Leu Arg
305 310 315 320

Arg Glu Pro Lys Trp Gly His Leu Arg Asp Leu His Lys Thr Ile Lys
325 330 335

Leu Cys Glu Pro Ser Leu Val Ser Val Asp Pro Lys Val Thr Ser Leu
340 345 350

Gly Ser Asn Gln Glu Ala His Val Phe Trp Thr Lys Thr Ser Cys Ala
355 360 365

Ala Phe Leu Ala Asn Tyr Asp Leu Lys Tyr Ser Val Arg Val Thr Phe
370 375 380

Gln Asn Leu Pro Tyr Asp Leu Pro Pro Trp Ser Val Ser Ile Leu Pro
385 390 395 400

Asp Cys Lys Thr Val Val Phe Asn Thr Ala Lys Val Val Ser Gln Gly

-continued

```
                405                 410                 415

Ser Leu Ala Lys Met Ile Ala Val Asn Ser Ala Phe Ser Trp Gln Ser
            420                 425                 430

Tyr Asn Glu Glu Thr Pro Ser Ala Asn Tyr Asp Ala Val Phe Thr Lys
        435                 440                 445

Asp Gly Leu Trp Glu Gln Ile Ser Val Thr Arg Asp Ala Thr Asp Tyr
    450                 455                 460

Leu Trp Tyr Met Thr Asp Val Thr Ile Gly Pro Asp Glu Ala Phe Leu
465                 470                 475                 480

Lys Asn Gly Gln Asp Pro Ile Leu Thr Val Met Ser Ala Gly His Ala
                485                 490                 495

Leu His Val Phe Val Asn Gly Gln Leu Ser Gly Thr Val Tyr Gly Gln
            500                 505                 510

Leu Glu Asn Pro Lys Leu Ala Phe Ser Gly Lys Val Lys Leu Arg Ala
        515                 520                 525

Gly Val Asn Lys Val Ser Leu Leu Ser Ile Ala Val Gly Leu Pro Asn
    530                 535                 540

Val Gly Leu His Phe Glu Thr Trp Asn Ala Gly Val Leu Gly Pro Val
545                 550                 555                 560

Thr Leu Lys Gly Val Asn Ser Gly Thr Trp Asp Met Ser Lys Trp Lys
                565                 570                 575

Trp Ser Tyr Lys Ile Gly Leu Lys Gly Glu Ala Leu Ser Leu His Thr
            580                 585                 590

Val Ser Gly Ser Ser Ser Val Glu Trp Val Glu Gly Ser Leu Leu Ala
        595                 600                 605

Gln Arg Gln Pro Leu Ile Trp Tyr Lys Thr Thr Phe Asn Ala Pro Val
    610                 615                 620

Gly Asn Asp Pro Leu Ala Leu Asp Met Asn Ser Met Gly Lys Gly Gln
625                 630                 635                 640

Ile Trp Ile Asn Gly Gln Ser Ile Gly Arg His Trp Pro Gly Tyr Lys
                645                 650                 655

Ala Arg Gly Ser Cys Gly Ala Cys Asn Tyr Ala Gly Ile Tyr Asp Glu
            660                 665                 670

Lys Lys Cys His Ser Asn Cys Gly Lys Ala Ser Gln Arg Trp Tyr His
        675                 680                 685

Val Pro Arg Ser Trp Leu Asn Pro Thr Ala Asn Leu Leu Val Val Phe
    690                 695                 700

Glu Glu Trp Gly Gly Asp Pro Thr Lys Ile Ser Leu Val Lys Arg Val
705                 710                 715                 720

Val


<210> SEQ ID NO 7
<211> LENGTH: 649
<212> TYPE: DNA
<213> ORGANISM: Carica papaya

<400> SEQUENCE: 7

gcagtggtgg caaaagatgg aacgggaaac tttcagacgg tgaaagaggc catggatgcg      60

gctgatggga aaaaaaggtt tgtgatttac gtgaaagcag gagtttataa ggagaaaatt     120

cacagtaata aagacgggat tactttgatc ggagatggta aatattccac catcattgtc     180

ggtgatgata gtgttgctgg aggttccacc atgccaggct ctgcaactat tacaatgaca     240

ggggatggat tcatagcccg cgacattggg tttcagaaca cagcagggcc acaaggagag     300
```

-continued

```
caagctttag ctctaaacat agcttctgat cactctgttc tttacaggtg cagcattgcg    360

ggttaccagg atactctcta cgcacacgct ctccgtcaat tctacagaga atgcgacatc    420

tacggcaccg tcgatttcat tttcggaaac gccgccgcgg ttttccaaaa ctgctacttg    480

gttcttcgtc ttcctcggaa aaaaggctac aacgttattc tagcaaacgg aagatccgac    540

ccgggacaga acacgggttt ctctgttcac aactgcagaa tcgtacccag ctccgaattt    600

tctccggtaa aacataaata cgaatcgtat cttggtaggc catggaaaa                649
```

<210> SEQ ID NO 8
<211> LENGTH: 216
<212> TYPE: PRT
<213> ORGANISM: Carica papaya

<400> SEQUENCE: 8

```
Ala Val Val Ala Lys Asp Gly Thr Gly Asn Phe Gln Thr Val Lys Glu
  1               5                  10                  15
Ala Met Asp Ala Ala Asp Gly Lys Lys Arg Phe Val Ile Tyr Val Lys
             20                  25                  30
Ala Gly Val Tyr Lys Glu Lys Ile His Ser Asn Lys Asp Gly Ile Thr
         35                  40                  45
Leu Ile Gly Asp Gly Lys Tyr Ser Thr Ile Ile Val Gly Asp Asp Ser
     50                  55                  60

Val Ala Gly Gly Ser Thr Met Pro Gly Ser Ala Thr Ile Thr Met Thr
 65                  70                  75                  80

Gly Asp Gly Phe Ile Ala Arg Asp Ile Gly Phe Gln Asn Thr Ala Gly
                 85                  90                  95

Pro Gln Gly Glu Gln Ala Leu Ala Leu Asn Ile Ala Ser Asp His Ser
            100                 105                 110

Val Leu Tyr Arg Cys Ser Ile Ala Gly Tyr Gln Asp Thr Leu Tyr Ala
        115                 120                 125

His Ala Leu Arg Gln Phe Tyr Arg Glu Cys Asp Ile Tyr Gly Thr Val
    130                 135                 140

Asp Phe Ile Phe Gly Asn Ala Ala Ala Val Phe Gln Asn Cys Tyr Leu
145                 150                 155                 160

Val Leu Arg Leu Pro Arg Lys Lys Gly Tyr Asn Val Ile Leu Ala Asn
                165                 170                 175

Gly Arg Ser Asp Pro Gly Gln Asn Thr Gly Phe Ser Val His Asn Cys
            180                 185                 190

Arg Ile Val Pro Ser Ser Glu Phe Ser Pro Val Lys His Lys Tyr Glu
        195                 200                 205

Ser Tyr Leu Gly Arg Pro Trp Lys
    210                 215
```

<210> SEQ ID NO 9
<211> LENGTH: 195
<212> TYPE: DNA
<213> ORGANISM: Carica papaya

<400> SEQUENCE: 9

```
gggacggggg atgattgtat ctcgttgagt ggtggctctg gaaatatcaa tgtcacaggt     60

gtccagtgtg gccccggtca cggcattagt atcggtagtc ttggaaagtt gaggaatgag    120

gaaaatgtgg ctgggatttt ggtccaaaat tgcgtgtttg aaggtaccac taacggcgtc    180

agcatcaaaa cctgg                                                     195
```

<210> SEQ ID NO 10
<211> LENGTH: 65
<212> TYPE: PRT

-continued

<213> ORGANISM: Carica papaya

<400> SEQUENCE: 10

```
Gly Thr Gly Asp Asp Cys Ile Ser Leu Ser Gly Gly Ser Gly Asn Ile
  1               5                  10                  15

Asn Val Thr Gly Val Gln Cys Gly Pro Gly His Gly Ile Ser Ile Gly
             20                  25                  30

Ser Leu Gly Lys Leu Arg Asn Glu Glu Asn Val Ala Gly Ile Leu Val
         35                  40                  45

Gln Asn Cys Val Phe Glu Gly Thr Thr Asn Gly Val Ser Ile Lys Thr
     50                  55                  60

Trp
 65
```

<210> SEQ ID NO 11
<211> LENGTH: 864
<212> TYPE: DNA
<213> ORGANISM: PRSV-KA-CP

<400> SEQUENCE: 11

```
tccaagaatg aagctgtgga tgctggtttg aatgaaaaac tcaaagagaa agaaagacag      60

aaagaaaaag aaaaagaaaa acaaaaagaa aaaggaaaag acgatgctag tgacgaaaat     120

gatgtgtcaa ctagcacaaa aactggagag agagatagag atgtcaatgt tgggaccagt     180

ggaactttcg ctgttccgag aattaaatca tttactgata agttgattct accaagaatt     240

aagggaaaga ctgtccttaa tttaagtcat cttcttcagt ataatccgca acaaattgac     300

atttctaaca ctcgtgccac tcagtcacaa tttgagaagt ggtatgaggg agtgagggat     360

gattatggcc ttaatgataa tgaaatgcaa gttatgctaa atggtttgat ggtttggtgt     420

atcgagaatg gtacatctcc agacatatct ggtgtatggg ttatgatgga tggggaaacc     480

caagttgatt atccaaccaa gcctttaatt gagcatgata ctccgtcatt taggcaaatt     540

atggctcact ttagtaacgc ggcagaagca tacattgcga agagaaatgc tactgagagg     600

tacatgccgc ggtacggaat caagagaaat ttgactgaca ttagcctcgc tagatatgct     660

ttcgacttct atgaggtgaa ttcgaaaaca cctgataggg ctcgcgaagc ccacatgcag     720

atgaaggctg cagcgctgcg aaacactagt cgcagaatgt ttggtatgga cggcagtgtt     780

agtaacaagg aagaaaacac ggagagacac acagtggaag atgtcgatag agacatgcac     840

tctctcctgg gtatgcgcaa ctaa                                            864
```

<210> SEQ ID NO 12
<211> LENGTH: 287
<212> TYPE: PRT
<213> ORGANISM: PRSV-KA-CP

<400> SEQUENCE: 12

```
Ser Lys Asn Glu Ala Val Asp Ala Gly Leu Asn Glu Lys Leu Lys Glu
  1               5                  10                  15

Lys Glu Arg Gln Lys Glu Lys Glu Lys Glu Lys Gln Lys Glu Lys Gly
             20                  25                  30

Lys Asp Asp Ala Ser Asp Glu Asn Asp Val Ser Thr Ser Thr Lys Thr
         35                  40                  45

Gly Glu Arg Asp Arg Asp Val Asn Val Gly Thr Ser Gly Thr Phe Ala
     50                  55                  60

Val Pro Arg Ile Lys Ser Phe Thr Asp Lys Leu Ile Leu Pro Arg Ile
 65                  70                  75                  80
```

-continued

```
Lys Gly Lys Thr Val Leu Asn Leu Ser His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Asp Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asp Arg Asp Met His Ser Leu Leu Gly Met Arg Asn
        275                 280                 285


<210> SEQ ID NO 13
<211> LENGTH: 861
<212> TYPE: DNA
<213> ORGANISM: PRSV-TH-CP

<400> SEQUENCE: 13

tccaagaatg aagctgtgga tgctggtctt aatgagaagt tcaaagataa agaaaaacag      60

aaagaagaaa aagataaaca aaaaggtaaa gaaaataatg aagctagtga cggaaatgat     120

gtgtcaacta gcacaaaaac tggagagaga gatagagatg tcaatgccgg aactagtggt     180

actttcactg ttccgagaat aaaattattt accgacaaga tgattttacc aagaattaag     240

ggaaaaactg tccttagttt aaatcatctt cttcagtata atccgcaaca aatagacatc     300

tcaaacactc gtgccactca atctcaattc gaaaagtggt atgagggagt gaggaatgat     360

tacggtctta atgataacga aatgcaagtg atgttaaatg gtttgatggt ttggtgcatc     420

gaaaatggaa catccccaga catatctggt gtctgggtga tgatggatgg ggaaacccaa     480

gtcgattatc ccatcaagcc tttgatcgaa catgcaactc cttcgttcag gcaaatcatg     540

gctcacttca gtaacgcggc agaggcatac atcgcaaaga ggaatgctac tgagaggtac     600

atgccgcggt atggaatcaa gaggaatctg actgacatta gtctcgctag atatgctttc     660

gacttctatg aggtgaactc aaaaacacct gatagggctc gtgaagctca tatgcagatg     720

aaggctgcag cgctgcgcaa cactgatcgc agaatgtttg gaatggacgg cagtgtcagt     780

aacaaggaag aaaacacgga gagacacaca gtggaagatg tcaacagaga catgcactct     840

ctcctaggta tgcgcaattg a                                               861
```

-continued

<210> SEQ ID NO 14
<211> LENGTH: 286
<212> TYPE: PRT
<213> ORGANISM: PRSV-TH-CP

<400> SEQUENCE: 14

```
Ser Lys Asn Glu Ala Val Asp Ala Gly Leu Asn Glu Lys Phe Lys Asp
  1               5                  10                  15

Lys Glu Lys Gln Lys Glu Glu Lys Asp Lys Gln Lys Gly Lys Glu Asn
             20                  25                  30

Asn Glu Ala Ser Asp Gly Asn Asp Val Ser Thr Ser Thr Lys Thr Gly
         35                  40                  45

Glu Arg Asp Arg Asp Val Asn Ala Gly Thr Ser Gly Thr Phe Thr Val
     50                  55                  60

Pro Arg Ile Lys Leu Phe Thr Asp Lys Met Ile Leu Pro Arg Ile Lys
 65                  70                  75                  80

Gly Lys Thr Val Leu Ser Leu Asn His Leu Leu Gln Tyr Asn Pro Gln
                 85                  90                  95

Gln Ile Asp Ile Ser Asn Thr Arg Ala Thr Gln Ser Gln Phe Glu Lys
            100                 105                 110

Trp Tyr Glu Gly Val Arg Asn Asp Tyr Gly Leu Asn Asp Asn Glu Met
        115                 120                 125

Gln Val Met Leu Asn Gly Leu Met Val Trp Cys Ile Glu Asn Gly Thr
    130                 135                 140

Ser Pro Asp Ile Ser Gly Val Trp Val Met Met Asp Gly Glu Thr Gln
145                 150                 155                 160

Val Asp Tyr Pro Ile Lys Pro Leu Ile Glu His Ala Thr Pro Ser Phe
                165                 170                 175

Arg Gln Ile Met Ala His Phe Ser Asn Ala Ala Glu Ala Tyr Ile Ala
            180                 185                 190

Lys Arg Asn Ala Thr Glu Arg Tyr Met Pro Arg Tyr Gly Ile Lys Arg
        195                 200                 205

Asn Leu Thr Asp Ile Ser Leu Ala Arg Tyr Ala Phe Asp Phe Tyr Glu
    210                 215                 220

Val Asn Ser Lys Thr Pro Asp Arg Ala Arg Glu Ala His Met Gln Met
225                 230                 235                 240

Lys Ala Ala Ala Leu Arg Asn Thr Asp Arg Arg Met Phe Gly Met Asp
                245                 250                 255

Gly Ser Val Ser Asn Lys Glu Glu Asn Thr Glu Arg His Thr Val Glu
            260                 265                 270

Asp Val Asn Arg Asp Met His Ser Leu Leu Gly Met Arg Asn
        275                 280                 285
```

<210> SEQ ID NO 15
<211> LENGTH: 921
<212> TYPE: DNA
<213> ORGANISM: PRSV-KE-CP1

<400> SEQUENCE: 15

```
tcaaggagca ctgatgatta tcaacttgtt tggagtgaca atacacatgt gtttcatcag      60

tccaagaatg aagctgtgga tgctggtttg aatgaaaaac tcaaagagaa agaaaaacag     120

aaagaaaaag aaaaagaaaa acaaaaagaa aaaggaagag acgatgctag tgacgaaaat     180

gatgtgtcaa ctagcacaaa aactggagag agagatagag atgtcaatgt tgggaccagt     240

ggaactttcg ctgttccgag aattaaatca tttactgata agttgattct accaagaatt     300
```

-continued

```
aagggaaaga ctgtccttaa tttaagtcat cttcttcagt ataatccgca acaaattgac    360

atttctaaca ctcgtgccac tcagtcacaa tttgagaagt ggtatgaggg agtgagggat    420

gattatggcc ttaatgataa tgaaatgcaa gttatgctaa atggtttgat ggtttggtgt    480

atcgagaatg gtacatctcc agacatatct ggtgtatggg ttatgatgga tggggaaacc    540

caagttgatt atccaaccaa gcctttaatt gagcatgcta ctccgtcatt taggcaaatt    600

atggctcact ttagtaacgc ggcagaagca tacattgcga agagaaatgc tactgagagg    660

tacatgccgc ggtacggaat caagagaaat ttgactgacg ttagcctcgc tagatatgct    720

ttcgacttct atgaggtgaa ttcgaaaaca cctgataggg ctcgcgaagc ccacatgcag    780

atgaaggctg cagcgctgcg aaacactagt cgcagaatgt ttggtatgga cggcagtgtt    840

agtaacaagg aagaaaacac ggagagacac acagtggaag atgtcaatag agacatgcac    900

tctctcctgg gcatgcgcaa c                                              921
```

<210> SEQ ID NO 16
<211> LENGTH: 864
<212> TYPE: DNA
<213> ORGANISM: PRSV-KE-CP2

<400> SEQUENCE: 16

```
tccaagaatg aagctgtgga tgctggtttg aatgaaaaac tcaaagagaa agaaaaacag     60

aaagaaaaag aaaaagaaaa acaaaaagaa aaaggaaaag acgatgctag tgacgaaaat    120

gatgtgtcaa ctagcacaaa aactggagag agagatagag atgtcaatgt tgggaccagt    180

ggaactttcg ctgttccgag aattaaatca tttactgata agttgattct accaagaatt    240

aagggaaaga ctgtccttaa tttaagtcat cttcttcagt ataatccgca acaaattgac    300

atttctaaca ctcgtgccac tcagtcacaa tttgagaagt ggtatgaggg agtgagggat    360

gattatggcc ttaatgataa tgaaatgcaa gttatgctaa atggtttgat ggtttggtgt    420

atcgagaatg gtacatctcc agacatatct ggtgtatggg ttatgatgga tggggaaacc    480

caagttgatt atccaaccaa gcctttaatt gagcatgcta ctccgtcatt taggcaaatt    540

atggctcact ttagtaacgc ggcagaagca tacattgcga agagaaatgc tactgagagg    600

tacatgccgc ggtacggaat caagagaaat ttgactgacg ttagcctcgc tagatatgct    660

ttcgacttct atgaggtgaa ttcgaaaaca cctgataggg ctcgcgaagc ccacatgcag    720

atgaaggctg cagcgctgcg aaacactagt cgcagaatgt ttggtatgga cggcagtgtt    780

agtaacaagg aagaaaacac ggagagacac acagtggaag atgtcaatag agacatgcac    840

tctctcctgg gcatgcgcaa ctaa                                           864
```

<210> SEQ ID NO 17
<211> LENGTH: 307
<212> TYPE: PRT
<213> ORGANISM: PRSV-KE-CP1

<400> SEQUENCE: 17

```
Ser Arg Ser Thr Asp Asp Tyr Gln Leu Val Trp Ser Asp Asn Thr His
  1               5                  10                  15

Val Phe His Gln Ser Lys Asn Glu Ala Val Asp Ala Gly Leu Asn Glu
             20                  25                  30

Lys Leu Lys Glu Lys Glu Lys Gln Lys Glu Lys Glu Lys Glu Lys Gln
         35                  40                  45

Lys Glu Lys Gly Arg Asp Asp Ala Ser Asp Glu Asn Asp Val Ser Thr
     50                  55                  60
```

-continued

```
Ser Thr Lys Thr Gly Glu Arg Asp Arg Asp Val Asn Val Gly Thr Ser
 65                  70                  75                  80

Gly Thr Phe Ala Val Pro Arg Ile Lys Ser Phe Thr Asp Lys Leu Ile
                85                  90                  95

Leu Pro Arg Ile Lys Gly Lys Thr Val Leu Asn Leu Ser His Leu Leu
            100                 105                 110

Gln Tyr Asn Pro Gln Gln Ile Asp Ile Ser Asn Thr Arg Ala Thr Gln
        115                 120                 125

Ser Gln Phe Glu Lys Trp Tyr Glu Gly Val Arg Asp Asp Tyr Gly Leu
    130                 135                 140

Asn Asp Asn Glu Met Gln Val Met Leu Asn Gly Leu Met Val Trp Cys
145                 150                 155                 160

Ile Glu Asn Gly Thr Ser Pro Asp Ile Ser Gly Val Trp Val Met Met
                165                 170                 175

Asp Gly Glu Thr Gln Val Asp Tyr Pro Thr Lys Pro Leu Ile Glu His
            180                 185                 190

Ala Thr Pro Ser Phe Arg Gln Ile Met Ala His Phe Ser Asn Ala Ala
        195                 200                 205

Glu Ala Tyr Ile Ala Lys Arg Asn Ala Thr Glu Arg Tyr Met Pro Arg
    210                 215                 220

Tyr Gly Ile Lys Arg Asn Leu Thr Asp Val Ser Leu Ala Arg Tyr Ala
225                 230                 235                 240

Phe Asp Phe Tyr Glu Val Asn Ser Lys Thr Pro Asp Arg Ala Arg Glu
                245                 250                 255

Ala His Met Gln Met Lys Ala Ala Ala Leu Arg Asn Thr Ser Arg Arg
            260                 265                 270

Met Phe Gly Met Asp Gly Ser Val Ser Asn Lys Glu Glu Asn Thr Glu
        275                 280                 285

Arg His Thr Val Glu Asp Val Asn Arg Asp Met His Ser Leu Leu Gly
    290                 295                 300

Met Arg Asn
305


<210> SEQ ID NO 18
<211> LENGTH: 287
<212> TYPE: PRT
<213> ORGANISM: PRSV-KE-CP2

<400> SEQUENCE: 18

Ser Lys Asn Glu Ala Val Asp Ala Gly Leu Asn Glu Lys Leu Lys Glu
  1               5                  10                  15

Lys Glu Lys Gln Lys Glu Lys Glu Lys Glu Lys Gln Lys Glu Lys Gly
            20                  25                  30

Lys Asp Asp Ala Ser Asp Glu Asn Asp Val Ser Thr Ser Thr Lys Thr
        35                  40                  45

Gly Glu Arg Asp Arg Asp Val Asn Val Gly Thr Ser Gly Thr Phe Ala
    50                  55                  60

Val Pro Arg Ile Lys Ser Phe Thr Asp Lys Leu Ile Leu Pro Arg Ile
 65                  70                  75                  80

Lys Gly Lys Thr Val Leu Asn Leu Ser His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
```

-continued

```
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Val Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285


<210> SEQ ID NO 19
<211> LENGTH: 864
<212> TYPE: DNA
<213> ORGANISM: PRSV-YK-CP

<400> SEQUENCE: 19

tctaaaaatg aagctgtgga taccggtctg aatgagaagc tcaaagaaaa agaaaagcag      60

aaagaaaaag aaaaagataa acaacaagat aaagacaatg atggagctag tgacggaaac     120

gatgtgtcaa ctagcacaaa aactggagag agagataggg atgtcaatgc cggaactagt     180

ggaaccttca ctgttccgag gataaagtca tttactgata agatgatctt accaagaatt     240

aagggaaaaa ctgtccttaa tttaaatcat cttcttcagt ataatccgaa acaagttgac     300

atctcaaaca ctcgcgccac tcaatctcaa tttgagaagt ggtatgaggg agtgagaaat     360

gattatggcc ttaatgataa cgaaatgcaa gtaatgttaa atggtttgat ggtttggtgt     420

atcgaaaatg gtacatctcc agatatatct ggtgtctggg ttatgatgga tggggaaacc     480

caagtcgatt atcccattaa acctttgatt gaacacgcaa ctccttcatt taggcaaatc     540

atggctcact tcagtaacgc ggcagaggca tacatcgcga agaggaatgc aactgagaag     600

tacatgccgc ggtatggaat caagagaaat ttgactgaca ttagtctcgc tagatatgct     660

ttcgatttct atgaggtgaa ttcgaaaaca cctgataggg ctcgtgaagc tcatatgcag     720

atgaaggctg cagcgctacg caatactaat cgcaaaatgt ttggaatgga cggcagtgtc     780

agtaacaagg aagaaaacac ggagagacac acagtggaag atgtcaacag agacatgcac     840

tctctcctgg gtatgcgcaa ttga                                            864


<210> SEQ ID NO 20
<211> LENGTH: 287
<212> TYPE: PRT
<213> ORGANISM: PRSV-YK-CP

<400> SEQUENCE: 20

Ser Lys Asn Glu Ala Val Asp Thr Gly Leu Asn Glu Lys Leu Lys Glu
```

-continued

```
 1               5                   10                  15

Lys Glu Lys Gln Lys Glu Lys Glu Lys Asp Lys Gln Gln Asp Lys Asp
            20                  25                  30

Asn Asp Gly Ala Ser Asp Gly Asn Asp Val Ser Thr Ser Thr Lys Thr
        35                  40                  45

Gly Glu Arg Asp Arg Asp Val Asn Ala Gly Thr Ser Gly Thr Phe Thr
    50                  55                  60

Val Pro Arg Ile Lys Ser Phe Thr Asp Lys Met Ile Leu Pro Arg Ile
65                  70                  75                  80

Lys Gly Lys Thr Val Leu Asn Leu Asn His Leu Leu Gln Tyr Asn Pro
                85                  90                  95

Lys Gln Val Asp Ile Ser Asn Thr Arg Ala Thr Gln Ser Gln Phe Glu
            100                 105                 110

Lys Trp Tyr Glu Gly Val Arg Asn Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Lys Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Asn Arg Lys Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

<210> SEQ ID NO 21
<211> LENGTH: 855
<212> TYPE: DNA
<213> ORGANISM: PRSV-ME-CP

<400> SEQUENCE: 21

```
tccaagaatg aagctgtgga tgctggtttg aatgaaaaac tcaaagaaaa agaaaaacag     60

aaagaaaaag aaaaacaaaa agaaaaagaa aaagacaatg ctagtgacgg aaatgatgtg    120

tcgactagca caaaaactgg agagaaagat agagatgtca atgtcggaac tagtggaact    180

ttcactgttc cgagaattaa atcatttact gataagatga ttctaccgag aattaaggga    240

aagactgtcc ttaatttaaa tcatcttctt cagtataatc cgcaacaaat tgatatttct    300

aacactcgtg ccactcagtc acaatttgag aaatggtatg agggagtgag gaatgattat    360

ggtctgaatg ataatgaaat gcaagtgatg ctgaatggct tgatggtttg gtgtatcgag    420

aatggtacat ctccagacat atctggtgtt tgggttatga tggatgggga aattcaagtt    480

gactatccaa tcaagcctct aattgagcat gctaccccgt catttaggca gattatggct    540
```

-continued

```
cactttagta acgcggcaga agcatatatt gcaaagagaa atgccactga gaggtacatg    600

ccgcggtatg gaatcaagag aaatttgact gacattagcc tcgctaggta cgctttcgat    660

ttctatgagg ttaattcgaa aacacctgat agggctcgcg aagctcacat gcagatgaaa    720

gctgcagcgc tgcgaaacac tagtcgcaga atgtttggta tgggcggcag tgttagtaac    780

aaggaagaaa acacggaaag acacacagtg gaagatgtca atagagacat gcactctctc    840

ctgggtatgc gcaac                                                     855
```

<210> SEQ ID NO 22
<211> LENGTH: 285
<212> TYPE: PRT
<213> ORGANISM: PRSV-ME-CP

<400> SEQUENCE: 22

```
Ser Lys Asn Glu Ala Val Asp Ala Gly Leu Asn Glu Lys Leu Lys Glu
  1               5                  10                  15

Lys Glu Lys Gln Lys Glu Lys Glu Lys Gln Lys Glu Lys Glu Lys Asp
             20                  25                  30

Asn Ala Ser Asp Gly Asn Asp Val Ser Thr Ser Thr Lys Thr Gly Glu
         35                  40                  45

Lys Asp Arg Asp Val Asn Val Gly Thr Ser Gly Thr Phe Thr Val Pro
     50                  55                  60

Arg Ile Lys Ser Phe Thr Asp Lys Met Ile Leu Pro Arg Ile Lys Gly
 65                  70                  75                  80

Lys Thr Val Leu Asn Leu Asn His Leu Leu Gln Tyr Asn Pro Gln Gln
                 85                  90                  95

Ile Asp Ile Ser Asn Thr Arg Ala Thr Gln Ser Gln Phe Glu Lys Trp
            100                 105                 110

Tyr Glu Gly Val Arg Asn Asp Tyr Gly Leu Asn Asp Asn Glu Met Gln
        115                 120                 125

Val Met Leu Asn Gly Leu Met Val Trp Cys Ile Glu Asn Gly Thr Ser
    130                 135                 140

Pro Asp Ile Ser Gly Val Trp Val Met Met Asp Gly Glu Ile Gln Val
145                 150                 155                 160

Asp Tyr Pro Ile Lys Pro Leu Ile Glu His Ala Thr Pro Ser Phe Arg
                165                 170                 175

Gln Ile Met Ala His Phe Ser Asn Ala Ala Glu Ala Tyr Ile Ala Lys
            180                 185                 190

Arg Asn Ala Thr Glu Arg Tyr Met Pro Arg Tyr Gly Ile Lys Arg Asn
        195                 200                 205

Leu Thr Asp Ile Ser Leu Ala Arg Tyr Ala Phe Asp Phe Tyr Glu Val
    210                 215                 220

Asn Ser Lys Thr Pro Asp Arg Ala Arg Glu Ala His Met Gln Met Lys
225                 230                 235                 240

Ala Ala Ala Leu Arg Asn Thr Ser Arg Arg Met Phe Gly Met Gly Gly
                245                 250                 255

Ser Val Ser Asn Lys Glu Glu Asn Thr Glu Arg His Thr Val Glu Asp
            260                 265                 270

Val Asn Arg Asp Met His Ser Leu Leu Gly Met Arg Asn
        275                 280                 285
```

<210> SEQ ID NO 23
<211> LENGTH: 861
<212> TYPE: DNA
<213> ORGANISM: PRSV-BR-CP

-continued

<400> SEQUENCE: 23

```
tccaaaaatg aagctgtgga tgctggtttg aatgaaaagc gtaaagaaca agagaaacaa      60
gaagaaaaag aagaaaaaca aaaaaagaaa gaaaaagacg atgctagtta cggaaacgat     120
gtgtcaacta gcacaagaac tggagagaga gacagagatg tcaatgttgg gaccagtgga     180
actttcactg ttccgagaac aaaatcattt actgataaga tgattttacc tagaattaag     240
ggaaaaactg tccttaattt aaatcatctg attcagtata atccgcaaca aattgacatt     300
tctaacactc gtgctactca atcacaattt gagaagtggt acgagggagt gaggaatgat     360
tatggcctta atgataatga gatgcaaata gtgctaaatg gtttgatggt ttggtgtatc     420
gaaaacggta catctccaga catatctggt gtctgggtta tgatggatgg ggaaacccag     480
gttgactatc caatcaagcc tttaattgag catgctactc cgtcgtttag gcaaattatg     540
gctcatttca gtaacgcggc agaagcatac attacaaaga gaaatgctac tgagaggtac     600
atgccgcggt atgggatcaa gagaaatttg actgacatta gtcttgctag atatgctttc     660
gatttctatg aggtgaattc gaaaacacct gatagggctc gcgaagctca catgcagatg     720
aaagctgcag cgctgcgaaa cactaatcgc agaatgtttg gtatggacgg cagtgttagt     780
aacaaggaag aaaacacgga gagacacaca gtggaagatg tcaatagaga catgcactct     840
ctcctgggta tgcgcaactg a                                                861
```

<210> SEQ ID NO 24
<211> LENGTH: 286
<212> TYPE: PRT
<213> ORGANISM: PRSV-BR-CP

<400> SEQUENCE: 24

```
Ser Lys Asn Glu Ala Val Asp Ala Gly Leu Asn Glu Lys Arg Lys Glu
  1               5                  10                  15

Gln Glu Lys Gln Glu Glu Lys Glu Glu Lys Gln Lys Lys Lys Glu Lys
             20                  25                  30

Asp Asp Ala Ser Tyr Gly Asn Asp Val Ser Thr Ser Thr Arg Thr Gly
         35                  40                  45

Glu Arg Asp Arg Asp Val Asn Val Gly Thr Ser Gly Thr Phe Thr Val
     50                  55                  60

Pro Arg Thr Lys Ser Phe Thr Asp Lys Met Ile Leu Pro Arg Ile Lys
 65                  70                  75                  80

Gly Lys Thr Val Leu Asn Leu Asn His Leu Ile Gln Tyr Asn Pro Gln
                 85                  90                  95

Gln Ile Asp Ile Ser Asn Thr Arg Ala Thr Gln Ser Gln Phe Glu Lys
            100                 105                 110

Trp Tyr Glu Gly Val Arg Asn Asp Tyr Gly Leu Asn Asp Asn Glu Met
        115                 120                 125

Gln Ile Val Leu Asn Gly Leu Met Val Trp Cys Ile Glu Asn Gly Thr
    130                 135                 140

Ser Pro Asp Ile Ser Gly Val Trp Val Met Met Asp Gly Glu Thr Gln
145                 150                 155                 160

Val Asp Tyr Pro Ile Lys Pro Leu Ile Glu His Ala Thr Pro Ser Phe
                165                 170                 175

Arg Gln Ile Met Ala His Phe Ser Asn Ala Ala Glu Ala Tyr Ile Thr
            180                 185                 190

Lys Arg Asn Ala Thr Glu Arg Tyr Met Pro Arg Tyr Gly Ile Lys Arg
        195                 200                 205
```

-continued

```
Asn Leu Thr Asp Ile Ser Leu Ala Arg Tyr Ala Phe Asp Phe Tyr Glu
    210                 215                 220

Val Asn Ser Lys Thr Pro Asp Arg Ala Arg Glu Ala His Met Gln Met
225                 230                 235                 240

Lys Ala Ala Ala Leu Arg Asn Thr Asn Arg Arg Met Phe Gly Met Asp
                245                 250                 255

Gly Ser Val Ser Asn Lys Glu Glu Asn Thr Glu Arg His Thr Val Glu
            260                 265                 270

Asp Val Asn Arg Asp Met His Ser Leu Leu Gly Met Arg Asn
        275                 280                 285


<210> SEQ ID NO 25
<211> LENGTH: 864
<212> TYPE: DNA
<213> ORGANISM: PRSV-JA-CP

<400> SEQUENCE: 25

tctaaaaatg aagctgtgga tgctggttta aatgaaaagc tcaaagaaaa agaaaaacag      60

aaagataaag aaaaagaaaa acaaaaagat aaagaaaaag gagatgctag tgacggaaat     120

gatggttcga ctagcacaaa aactggagag agagatagag atgtcaatgt tgggaccagt     180

ggaacttcca ctgttccgag aattaaatca ttcactgata agatggttct accaagaatt     240

aagggaaaaa ctgtccttaa tttaaatcat cttcttcagt ataatccaca acaaattgac     300

atttctaaca ctcgtgccac tcagtcacaa tttgagaagt ggtacgaagg agtgaggagt     360

gattatggcc taaatgatag tgaaatgcaa gtgacgctaa atggcttgat ggtttggtgt     420

atcgagaatg gtacatctcc agacatatct ggtgtctggg ttatgatgga tggggaaacc     480

caagttgatt atccaatcaa gcctttaatt gagcacgcta ccccatcatt taggcagatt     540

atggctcact tcagtaacgc ggcagaagca tacactgcaa agagaaatgc tactgagagg     600

tacatgccgc ggtatggaat caagagaaat ttgactgaca ttagtctcgc tagatacgct     660

ttcgatttct atgaggtgaa ttcgaagaca cctgataggg ctcgtgaagc tcacatgcag     720

atgaaagctg cagcgctgcg aaacactaat cgcagaatgt ttggtatgga cggcagtgtt     780

agtaacaatg aagaaaacac ggagagacac acagtggaag atgtctatat agacatgcac     840

tctctcctgc gtttgcgcaa ctga                                            864


<210> SEQ ID NO 26
<211> LENGTH: 287
<212> TYPE: PRT
<213> ORGANISM: PRSV-JA-CP

<400> SEQUENCE: 26

Ser Lys Asn Glu Ala Val Asp Ala Gly Leu Asn Glu Lys Leu Lys Glu
  1               5                  10                  15

Lys Glu Lys Gln Lys Asp Lys Glu Lys Glu Lys Gln Lys Asp Lys Glu
            20                  25                  30

Lys Gly Asp Ala Ser Asp Gly Asn Asp Gly Ser Thr Ser Thr Lys Thr
        35                  40                  45

Gly Glu Arg Asp Arg Asp Val Asn Val Gly Thr Ser Gly Thr Ser Thr
     50                  55                  60

Val Pro Arg Ile Lys Ser Phe Thr Asp Lys Met Val Leu Pro Arg Ile
 65                  70                  75                  80

Lys Gly Lys Thr Val Leu Asn Leu Asn His Leu Leu Gln Tyr Asn Pro
                85                  90                  95
```

-continued

```
Gln Gln Ile Asp Ile Ser Asn Thr Arg Ala Thr Gln Ser Gln Phe Glu
            100                 105                 110

Lys Trp Tyr Glu Gly Val Arg Ser Asp Tyr Gly Leu Asn Asp Ser Glu
        115                 120                 125

Met Gln Val Thr Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Thr
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Asn Arg Arg Met Phe Gly Met
                245                 250                 255

Asp Gly Ser Val Ser Asn Asn Glu Glu Asn Thr Glu Arg His Thr Val
            260                 265                 270

Glu Asp Val Tyr Ile Asp Met His Ser Leu Leu Arg Leu Arg Asn
        275                 280                 285
```

<210> SEQ ID NO 27
<211> LENGTH: 864
<212> TYPE: DNA
<213> ORGANISM: PRSV-OA-CP

<400> SEQUENCE: 27

```
tccaagaatg aagctgtgga tgctggtttg aatgaaaaat tcaaagagaa ggaaaaacag      60

aaagaaaaag aaaaagaaaa acaaaaagag aaagaaaaag atggtgctag tgacgaaaat     120

gatgtgtcaa ctagcacaaa aactggagag agagatagag atgtcaatgt cgggaccagt     180

ggaactttca cagttccgag aattaaatca tttactgata agatgattct accgagaatt     240

aaggggaagg ctgtccttaa tttaaatcat cttcttcagt acaatccgca acaaatcgac     300

atttctaaca ctcgtgccgc tcattcacaa tttgaaaagt ggtatgaggg agtgaggaat     360

gattatgccc ttaatgataa tgaaatgcaa gtgatgctaa atggtttgat ggtttggtgt     420

atcgagaatg gtacatctcc agacatatct ggtgtctggg taatgatgga tggggaaacc     480

caagtcgatt atccaatcaa gcctttgatt gagcatgcta ctccgtcatt taggcaaatt     540

atggctcact ttagtaacgc ggcagaagca tacattgcga agagaaatgc tactgagagg     600

tacatgccgc ggtatggaat caagagaaat ttgactgaca ttagcctcgc tagatacgct     660

ttcgactttt atgaggtgaa ttcgaaaaca cctgatagag ctcgcgaagc tcacatgcag     720

atgaaggctg cagcgctgcg aaacaccagt cgcagaatgt ttggtatgga cggcagtgtt     780

agtaacaagg aagaaaacac ggagagacac acagtggaag atgtcaatag agacatgcac     840

tctctcctgg gtatgcgcaa ctaa                                            864
```

<210> SEQ ID NO 28
<211> LENGTH: 287
<212> TYPE: PRT

-continued

<213> ORGANISM: PRSV-OA-CP

<400> SEQUENCE: 28

```
Ser Lys Asn Glu Ala Val Asp Ala Gly Leu Asn Glu Lys Phe Lys Glu
  1               5                  10                  15

Lys Glu Lys Gln Lys Glu Lys Glu Lys Glu Lys Gln Lys Glu Lys Glu
             20                  25                  30

Lys Asp Gly Ala Ser Asp Glu Asn Asp Val Ser Thr Ser Thr Lys Thr
         35                  40                  45

Gly Glu Arg Asp Arg Asp Val Asn Val Gly Thr Ser Gly Thr Phe Thr
     50                  55                  60

Val Pro Arg Ile Lys Ser Phe Thr Asp Lys Met Ile Leu Pro Arg Ile
 65                  70                  75                  80

Lys Gly Lys Ala Val Leu Asn Leu Asn His Leu Leu Gln Tyr Asn Pro
                 85                  90                  95

Gln Gln Ile Asp Ile Ser Asn Thr Arg Ala Ala His Ser Gln Phe Glu
            100                 105                 110

Lys Trp Tyr Glu Gly Val Arg Asn Asp Tyr Ala Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

<210> SEQ ID NO 29
<211> LENGTH: 885
<212> TYPE: DNA
<213> ORGANISM: PRSV-VE-CP
<220> FEATURE:
<221> NAME/KEY: unsure
<222> LOCATION: (678)
<223> OTHER INFORMATION: M at position 678 in this sequence is either a or c

<400> SEQUENCE: 29

```
atggctgtgg atgctggttt gaatgggaag ctcaaagaaa aagagaaaaa agaaaaagaa      60

aaagaaaaac agaaagagaa agagaaagat gatgctagtg acggaaatga tgtgtcaact     120

agcacaaaaa ctggagagag agatagagat gtcaatattg ggaccagtgg aactttcact     180

gtccctagga ttaaatcatt tactgataag atgattttac cgagaattaa gggaaagact     240
```

-continued

```
gtccttaatt taaatcatct tcttcagtat aatccgaaac aaattgacat ttctaatact    300

cgtgccactc agtcgcaatt tgagaaatgg tatgagggag tgagggatga ttatggcctt    360

aatgataatg aaatgcaagt gatgctaaat ggcttgatgg tttggtgcat tgagaatggt    420

acatctccag acatatctgg tgtttgggtt atggtggatg gggaaaccca agttgattat    480

ccaatcaagc ctttaattga gcatgctaca ccgtcattta ggcaaattat ggctcatttt    540

agtaacgcgg cagaagcata cattgcgatg agaaatgcta ctgagaggta catgccgcgg    600

tatggaatca agagaaattt gactgacatc aacctagctc gatacgcttt tgatttctat    660

gaggtgaatt cgaaaacmcc tgatagggct cgtgaagctc acatgcagat gaaggctgca    720

gctttgcgaa acactaatcg cagaatgttt ggtatcgacg gcagtgttag caacaaggaa    780

gaaaacacgg agagacacac agtggatgat gtcaatagag acatgcactc tctcctgggt    840

atgcgcaact aaatactcgc acttgtgtgt ttgtcgagcc tgact                    885
```

<210> SEQ ID NO 30
<211> LENGTH: 282
<212> TYPE: PRT
<213> ORGANISM: PRSV-VE-CP
<220> FEATURE:
<221> NAME/KEY: UNSURE
<222> LOCATION: (225)
<223> OTHER INFORMATION: Xaa at position 225 in this sequence is any amino acid

<400> SEQUENCE: 30

```
Met Ala Val Asp Ala Gly Leu Asn Gly Lys Leu Lys Glu Lys Glu Lys
  1               5                  10                  15

Lys Glu Lys Glu Lys Glu Lys Gln Lys Glu Lys Glu Lys Asp Asp Ala
             20                  25                  30

Ser Asp Gly Asn Asp Val Ser Thr Ser Thr Lys Thr Gly Glu Arg Asp
         35                  40                  45

Arg Asp Val Asn Ile Thr Ser Gly Thr Phe Thr Val Pro Arg Ile Lys
     50                  55                  60

Ser Phe Thr Asp Lys Met Ile Leu Pro Arg Ile Lys Gly Lys Thr Val
 65                  70                  75                  80

Leu Asn Leu Asn His Leu Leu Gln Tyr Asn Pro Lys Gln Ile Asp Ile
                 85                  90                  95

Ser Asn Thr Arg Ala Thr Gln Ser Gln Phe Glu Lys Trp Tyr Glu Gly
            100                 105                 110

Val Arg Asp Asp Tyr Gly Leu Asn Asp Asn Glu Met Gln Val Met Leu
        115                 120                 125

Asn Gly Leu Met Val Trp Cys Ile Glu Asn Gly Thr Ser Pro Asp Ile
    130                 135                 140

Ser Gly Val Trp Val Met Val Asp Gly Glu Thr Gln Val Asp Tyr Pro
145                 150                 155                 160

Ile Lys Pro Leu Ile Glu His Ala Thr Pro Ser Phe Arg Gln Ile Met
                165                 170                 175

Ala His Phe Ser Asn Ala Ala Glu Ala Tyr Ile Ala Met Arg Asn Ala
            180                 185                 190

Thr Glu Arg Tyr Met Pro Arg Tyr Gly Ile Lys Arg Asn Leu Thr Asp
        195                 200                 205

Ile Asn Leu Ala Arg Tyr Ala Phe Asp Phe Tyr Glu Val Asn Ser Lys
    210                 215                 220

Xaa Pro Asp Arg Ala Arg Glu Ala His Met Gln Met Lys Ala Ala Ala
225                 230                 235                 240
```

-continued

```
Leu Arg Asn Thr Asn Arg Arg Met Phe Gly Ile Asp Gly Ser Val Ser
            245                 250                 255

Asn Lys Glu Glu Asn Thr Glu Arg His Thr Val Asp Asp Val Asn Arg
        260                 265                 270

Asp Met His Ser Leu Leu Gly Met Arg Asn
    275                 280
```

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Amplification Oligos
<220> FEATURE:
<221> NAME/KEY: unsure
<222> LOCATION: (5)
<223> OTHER INFORMATION: N at position 5 in this sequence is Inosine
<220> FEATURE:
<221> NAME/KEY: unsure
<222> LOCATION: (12)
<223> OTHER INFORMATION: N at position 12 in this sequence is Inosine

<400> SEQUENCE: 31
agactatcgt ttcttggaat g 21

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Amplification Oligos
<220> FEATURE:
<221> NAME/KEY: unsure
<222> LOCATION: (19)
<223> OTHER INFORMATION: N at position 19 in this sequence is Inosine
<220> FEATURE:
<221> NAME/KEY: unsure
<222> LOCATION: (22)
<223> OTHER INFORMATION: N at position 22 in this sequence is Inosine

<400> SEQUENCE: 32
gaagtggaat cttatcgggg ttcc 24

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Amplification Oligos

<400> SEQUENCE: 33
cacagtaaga aaccattgca ag 22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Amplification Oligos
<220> FEATURE:
<221> NAME/KEY: unsure
<222> LOCATION: (11)
<223> OTHER INFORMATION: N at position 11 in this sequence is Inosine
<220> FEATURE:
<221> NAME/KEY: unsure -continued
<222> LOCATION: (14)
<223> OTHER INFORMATION: N at position 14 in this sequence is Inosine
<220> FEATURE:
<221> NAME/KEY: unsure
<222> LOCATION: (17)
<223> OTHER INFORMATION: N at position 17 in this sequence is Inosine

<400> SEQUENCE: 34
ccagaaagtt gtccccagtg 20

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Amplification Oligos

<400> SEQUENCE: 35
tggctccctc cttagtccat actc 24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Amplification Oligos

<400> SEQUENCE: 36
gcttactccg ttgcaaggtt catt 24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Amplification Oligos

<400> SEQUENCE: 37
aagggagggt cgttcattaa ctat 24

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Amplification Oligos

<400> SEQUENCE: 38
gggccctcat gttgaagaca aacctggtct tgttc 35

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Amplification Oligos

<400> SEQUENCE: 39
ggatcccccg ggattagggt taaactataa acctttacc 39

<210> SEQ ID NO 40
<211> LENGTH: 37

-continued

<212> TYPE: DNA
<213> ORGANISM: Artificial Sequence
<220> FEATURE:
<223> OTHER INFORMATION: Description of Artificial Sequence:
Amplification Oligos

<400> SEQUENCE: 40
gggggcccaa ggacctttca aggcatacat gcaaaga 37

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 41
cgggatcccc cgggcactgg ggcagggatc tccac 35

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 42
gggccctcat gttgtagaca aacctggtct tgttc 35

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 43 ggatccccg ggattagggt taaactataa acctttacc 39

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 44
cgggatcccc cgggcactgg ggcagggatc tccac 35

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 45
gggggcccaa ggacctttca aggcatacat gcaataga 38

<210> SEQ ID NO 46
<211> LENGTH: 35
<212> TYPE: DNA

-continued

<213> ORGANISM: Artificial Sequence
<220> FEATURE:
<223> OTHER INFORMATION: Description of Artificial Sequence:
Amplification Oligos

<400> SEQUENCE: 46
gggccctcat gttgaagaca aacctggtct tgttc 35

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 47
ggatcccccg ggattagggt taaactataa acctttacc 39

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 48
gggggcccaa ggacctttca aggcatacat gcaaaga 37

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 49
cgggatcccc cgggcactgg ggcagggatc tccac 35

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 50
gattgggccc atggtttgat agtccaaagt gaagctgtgg atgctgg 47

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 51
gaacggatcc tctagattag ttgcgcatgc ccaggagaga gtgcatg 47

<210> SEQ ID NO 52
<211> LENGTH: 35
<212> TYPE: DNA
<213> ORGANISM: Artificial Sequence -continued

```
<220> FEATURE:
<223> OTHER INFORMATION: Description of Artificial Sequence:
      Amplification Oligos

<400> SEQUENCE: 52

gggccctcat gttgtagaca aacctggtct tgttc                               35


<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 53

ggatcccccg ggattagggt taaactataa acctttacc                           39


<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 54

cgggatcccc cgggcactgg ggcagggatc tccac                               35


<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 55

gggggcccaa ggacctttca aggcatacat gcaataga                            38


<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 56

gggccctcat gttgtagaca aacctggtct tgttc                               35


<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 57

ggatcccccg ggattagggt taaactataa acctttacc                           39


<210> SEQ ID NO 58
<211> LENGTH: 35
<212> TYPE: DNA
<213> ORGANISM: Artificial Sequence
<220> FEATURE:
```

-continued

<223> OTHER INFORMATION: Description of Artificial Sequence:
Amplification Oligos

<400> SEQUENCE: 58
cgggatcccc cgggcactgg ggcagggatc tccac 35

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 59
gggggcccaa ggacctttca aggcatacat gcaataga 38

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 60
gggggcccag acgtacgtgt tttggaatgg gcat 34

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 61
cgggatcccc gaaattggtg ccgccgtg 28

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 62
gggggcccag acgtacgtgt tttggaatgg gcat 34

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 63
cgggatcccc gaaattggtg ccgccatg 28

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence:

```
                          Amplification Oligos

<400> SEQUENCE: 64

gggggcccga atggaattat gggggggttc c                                    31

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 65

cgggatcccc aaagttggtg ccgccatg                                        28

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 66

ccgctcgaga gacgtatgtg ttttggaatg gacat                                35

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 67

tcccccgggc caaaattggt gccgccgtg                                       29

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 68

tcccccggga gacgtacgtg ttttggaatg ggcat                                35

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 69

gggggccccc gaaattggtg ccgccatg                                        28

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence:
      Amplification Oligos
```

-continued

<400> SEQUENCE: 70
gggggcccga atggaattat gggggggttc c 31

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Amplification Oligos

<400> SEQUENCE: 71
cgggatcccc aaagttggtg ccgccatg 28

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence: Amplification Oligos

<400> SEQUENCE: 72
ccgctcgaga gacgtatgtg ttttggaatg gacat 35

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Amplification Oligos

<400> SEQUENCE: 73
tcccccgggc cgaaattggt gccgccatg 29

<210> SEQ ID NO 74
<211> LENGTH: 32
<212> TYPE: DNA
<213> ORGANISM: Artificial Sequence
<220> FEATURE:
<223> OTHER INFORMATION: Description of Artificial Sequence: Amplification Oligos

<400> SEQUENCE: 74
tcccccgggg aatggaatta tgggggggtt cc 32

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Amplification Oligos

<400> SEQUENCE: 75
gggggccccc aaagttggtg ccgccatg 28

<210> SEQ ID NO 76
<211> LENGTH: 34
<212> TYPE: DNA
<213> ORGANISM: Artificial Sequence
<220> FEATURE:
<223> OTHER INFORMATION: Description of Artificial Sequence: Amplification Oligos -continued

<400> SEQUENCE: 76
gggggcccag acgtacgtgt tttggaatgg gcat 34

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Amplification Oligos

<400> SEQUENCE: 77
cgggatcccc gaaattggtg ccgccatg 28

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: Amplification Oligos

<400> SEQUENCE: 78
ccgctcgagg aatggaatta tggggggttc cg 32

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Amplification Oligos

<400> SEQUENCE: 79
tcccccgggc caaagttggt gccgccatg 29

<210> SEQ ID NO 80
<211> LENGTH: 35
<212> TYPE: DNA
<213> ORGANISM: Artificial Sequence
<220> FEATURE:
<223> OTHER INFORMATION: Description of Artificial Sequence: Amplification Oligos

<400> SEQUENCE: 80
gggggcccat gttgaagaca aacctggtct tgttc 35

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Amplification Oligos

<400> SEQUENCE: 81
cgggatccca tttgtgcctt gaaaggtcca tt 32

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Amplification Oligos

<400> SEQUENCE: 82

-continued gggggccctg aacctcaagg gggtccaat 29

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 83
cgggatcctg cccccatttt ggctcc 26

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 84
gggggccctt gagggatttg cataaaacca tca 33

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 85
cgggatccct gatagttgac cattcacaaa aacatg 36

<210> SEQ ID NO 86
<211> LENGTH: 35
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 86
gggggcccct gtatatggac aattggaaaa tccca 35

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 87
cgggatccta ccatctctga gaagcctttc cac 33

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 88

-continued

```
agacntatcg tnttcttgga atg                                         23


<210> SEQ ID NO 89
<211> LENGTH: 26
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 89

gaagtggaat cttatcggng gnttcc                                      26


<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 90

ccagaaagtt ngtnccncca gtg                                         23
```